(12) United States Patent
Filiano et al.

(10) Patent No.: US 11,389,509 B1
(45) Date of Patent: Jul. 19, 2022

(54) METHODS FOR TREATMENT OF SOCIAL DYSFUNCTION NEUROLOGICAL DISORDERS AND SEIZURES

(71) Applicant: University of Virginia Patent Foundation, Charlottesville, VA (US)

(72) Inventors: Anthony J. Filiano, Charlottesville, VA (US); Jonathan Kipnis, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/033,160

(22) Filed: Jul. 11, 2018

Related U.S. Application Data

(60) Provisional application No. 62/531,543, filed on Jul. 12, 2017.

(51) Int. Cl.
  *A61K 38/21*     (2006.01)
  *A61K 38/17*     (2006.01)
  *A61K 31/5513*   (2006.01)
  *A61P 25/08*     (2006.01)
  *A61K 9/00*      (2006.01)
  *A61P 25/28*     (2006.01)

(52) U.S. Cl.
  CPC .......... *A61K 38/217* (2013.01); *A61K 9/0014* (2013.01); *A61K 9/0019* (2013.01); *A61K 31/5513* (2013.01); *A61K 38/17* (2013.01); *A61P 25/08* (2018.01); *A61P 25/28* (2018.01)

(58) Field of Classification Search
  CPC .. A61K 38/217; A61K 9/0014; A61K 9/0019; A61K 9/0085; A61K 9/7023; A61P 25/28; A61P 25/18; A61P 25/08; A61P 25/22; A61P 25/24
  See application file for complete search history.

(56) References Cited

U.S. PATENT DOCUMENTS

| | | | |
|---|---|---|---|
| 2006/0193860 A1* | 8/2006 | Skurkovich | C07K 16/241 424/145.1 |
| 2009/0010873 A1* | 1/2009 | Eisenbach-Schwartz | A61K 38/2026 514/1.1 |
| 2014/0294761 A1* | 10/2014 | Kraig | A61P 25/06 424/85.2 |
| 2017/0326356 A1* | 11/2017 | Huh | A61N 1/0531 |

FOREIGN PATENT DOCUMENTS

| | | | | |
|---|---|---|---|---|
| DE | 102012011839 A1 | * | 12/2013 | ......... A61K 31/5415 |
| JP | 2002087951 A | * | 3/2002 | |

OTHER PUBLICATIONS

Grüber et al. J. Clin. Psychiatry, 2014, 75(11), 1266-1267. (Year: 2014).*
English language machine translation for DE 102012011839 A1, from EPO Patent Translate; worldwide.espacenet.com; obtained Jan. 3, 2020. (Year: 2020).*
English language machine translation of JP 2002087951A, from EPO Patent Translate; worldwide.espacenet.com; obtained Jan. 3, 2020. (Year: 2020).*
Pereira L et al. IFN gamma regulates proliferation and neuronal differentiation by STAT1 in adult SVZ niche. Front. Cellular Neuroscience, Jul. 13, 2015, vol. 9, Article 270, pp. 1-10. (Year: 2015).*
Teoh HJ et al. A comparison of headache and non-headache sufferers on measures of social support and mental health problems. Malaysian Family Physician, 2008, 3(2):82-86. (Year: 2008).*
"More than "just a headache"" by The Migraine Trust, www.migrainetrust.org/about-migraine/migraine-what-is-it/more-than-just-a-headache/, retrieved from internet May 8, 2020. (Year: 2020).*
Wang J et al. Headache disorder and the risk of dementia: a systematic review and meta-analysis of cohort studies. J. Headache Pain, 2018, 19(1):95. (Year: 2018).*
Goines PE and Ashwood P. Neurotoxicol. Teratol. 36, 67-81. (Year: 2013).*
Lee J et al. Biotechnol. Appl. Biochem. 42, 169-173. (Year: 2005).*
Monteiro S et al. Prog. Neurobiol. 156, 149-163. (Year: 2017).*
Taipa R et al. Neurobiol. Aging, 76, 125-132. (Year: 2019).*
Zhang J et al. Priming of microglia with IFN-gamma impairs adult hippocampal neurogenesis and leads to depression-like behaviors and cognitive defects. Glia, 68, 2674-2692. (Year: 2020).*

* cited by examiner

*Primary Examiner* — Kimberly Ballard
(74) *Attorney, Agent, or Firm* — McCarter & English, LLP; Marcie B. Clarke

(57) ABSTRACT

The present disclosure relates to methods of treating social dysfunction neurological disorders in an animal subject, comprising administering to the subject a therapeutically effective amount of a compound that increases STAT1 activity, and to a method of treating seizures in an animal subject, comprising administering to the subject a therapeutically effective amount of a compound that increases STAT1 activity. In some embodiments, the compound is IFN-γ.

3 Claims, 50 Drawing Sheets

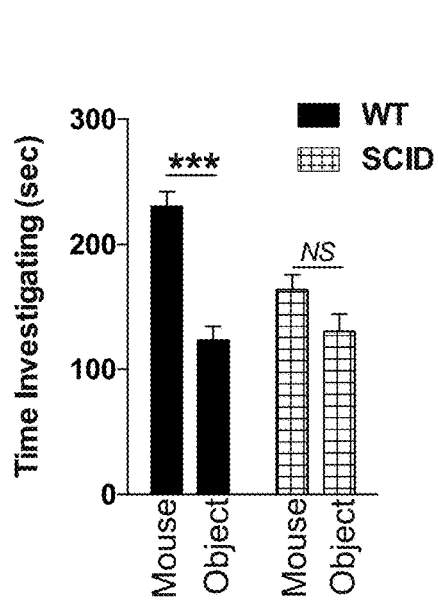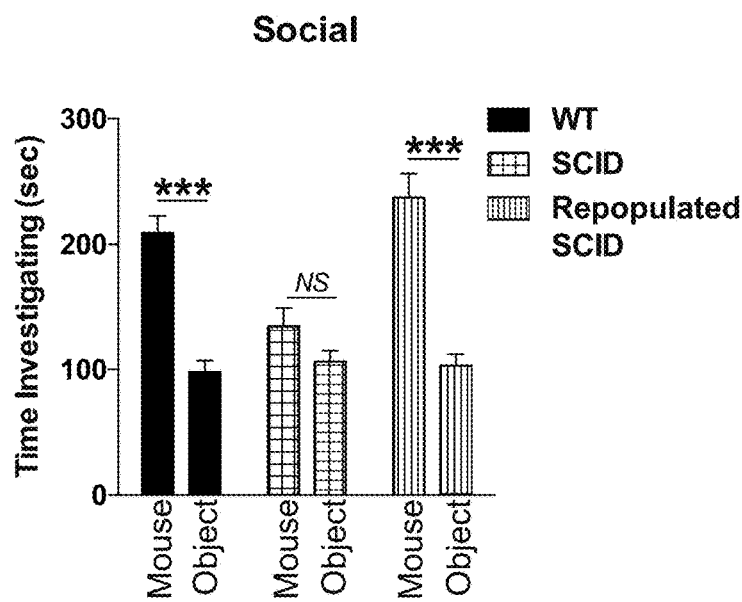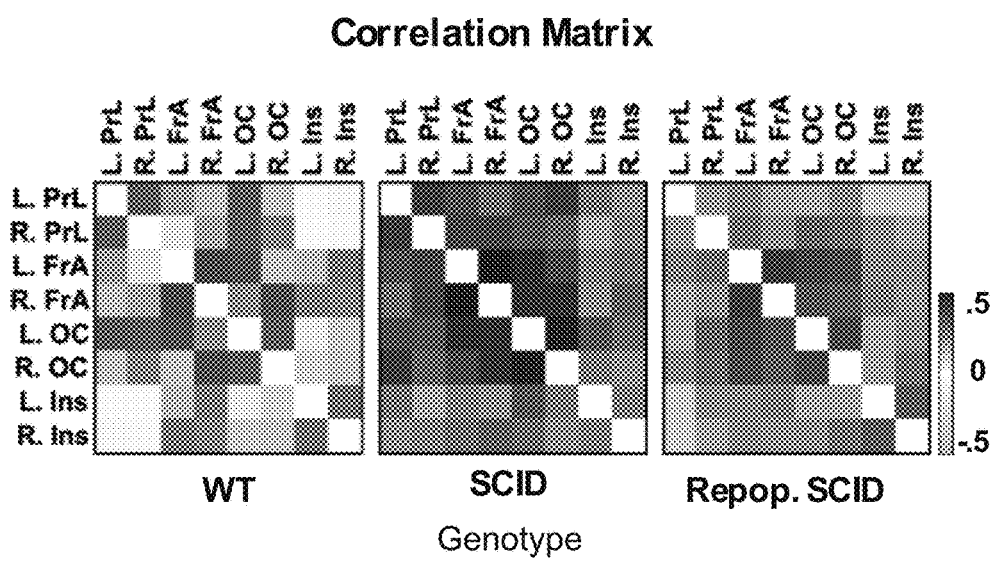
FIG. 1A
FIG. 1B
FIG. 1C

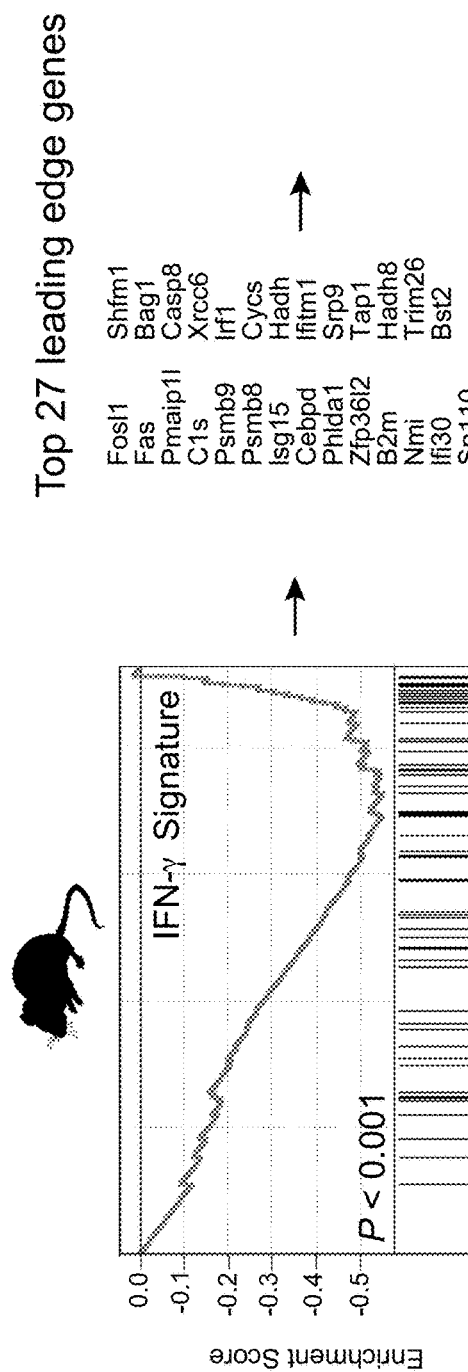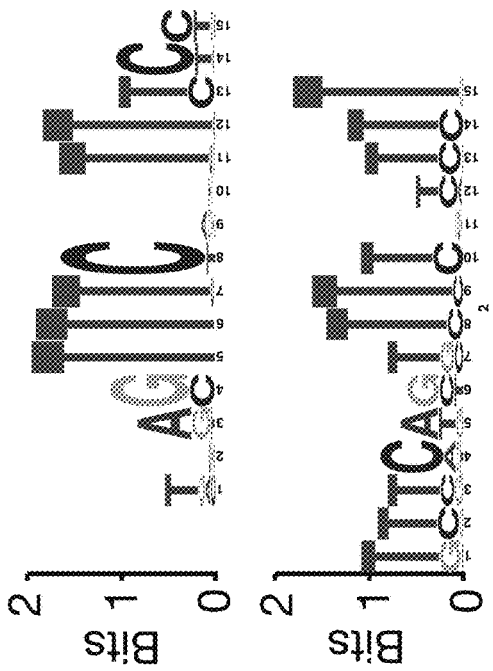
FIG. 3A
FIG. 3B
FIG. 3C

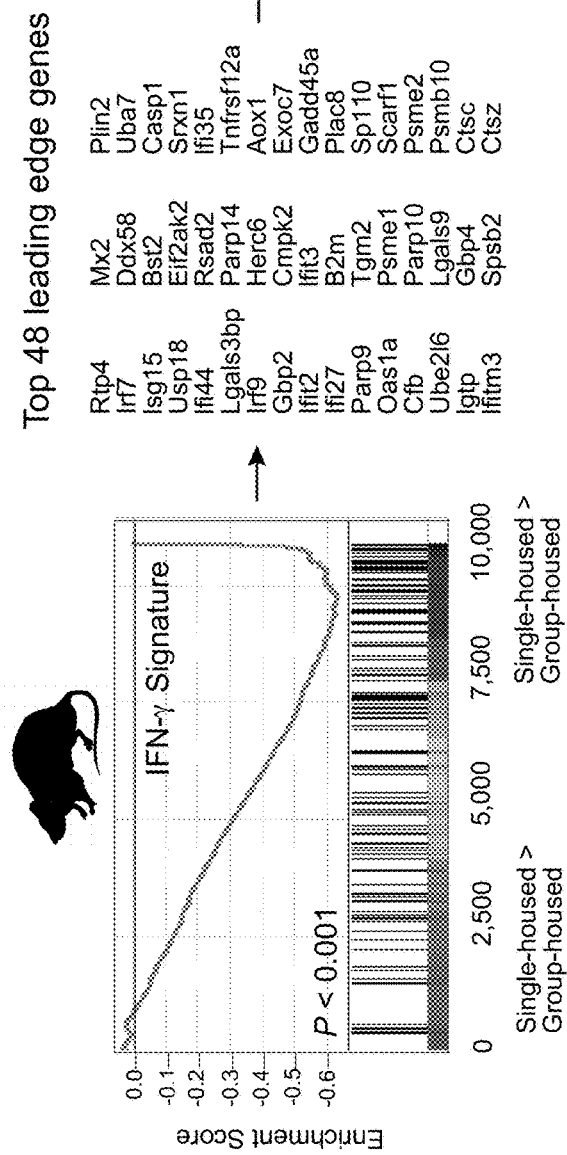
FIG. 3D
FIG. 3E
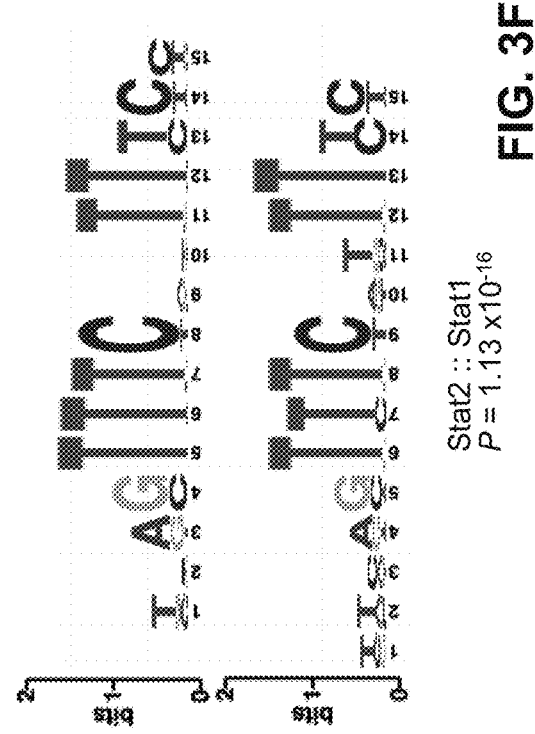
FIG. 3F

Stat2 :: Stat1 $P = 4.43 \times 10^{-5}$

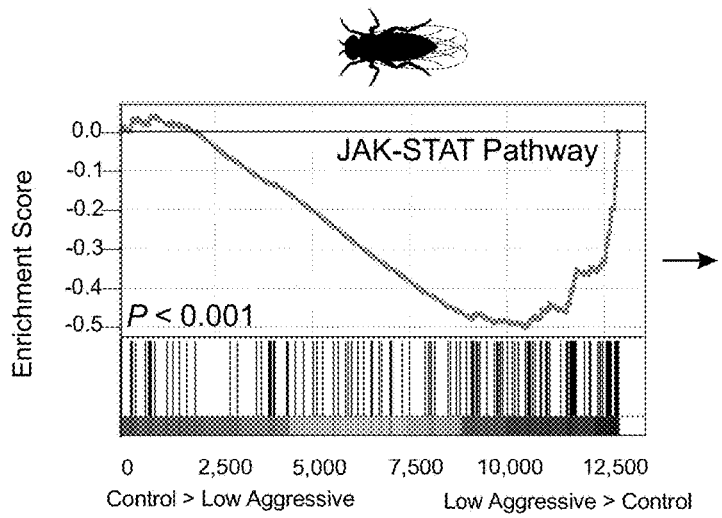
FIG. 3J
Top 53 leading-edge genes
| | | |
|---|---|---|
| CG4362 | CG14205 | CG33631 |
| DptB | ex | Ets21C |
| PgRP-SA | Listericin | CG32150 |
| AttB | CG6639 | rho |
| CecC | Gr28a | CG12688 |
| Mec2 | rt | CG14957 |
| Spn88Eb | os | Obp99b |
| AttB | CG12898 | CG4199 |
| CG42232 | CG12490 | shakB |
| CG12780 | CG32302 | Tep5 |
| AttA | jeb | CG9989 |
| CG17816 | CG31324 | SK |
| CG13640 | CG2963 | CG14720 |
| CG30031 | CG14837 | CG5756 |
| CecB | CG6739 | Spt |
| CG13641 | CG32354 | mei-9 |
| Socs36E | CG16643 | scb |
| | b6 | |
FIG. 3K
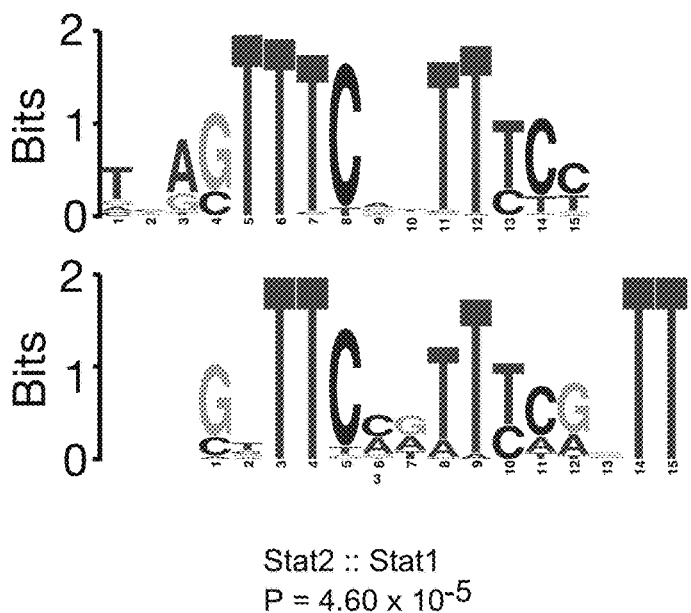
Stat2 :: Stat1
$P = 4.60 \times 10^{-5}$
FIG. 3L

Anxiety

METHODS FOR TREATMENT OF SOCIAL DYSFUNCTION NEUROLOGICAL DISORDERS AND SEIZURES

INCORPORATION BY REFERENCE TO ANY PRIORITY APPLICATIONS

Provisional Appln. No. 62/531,543, filed Jul. 12, 2017 is hereby incorporated by reference in its entirety including the drawings under 37 CFR 1.57. Any and all applications for which a foreign or domestic priority claim is identified in the Application Data Sheet as filed with the present application are hereby incorporated by reference under 37 CFR 1.57.

STATEMENT REGARDING FEDERALLY SPONSORED R&D

This invention was made with government support under Grant Nos. AG034113 and NS081026 awarded by the National Institutes of Health. The government has certain rights in the invention.

BACKGROUND OF THE INVENTION

Field of the Invention

Immune dysfunction is commonly associated with several neurological and mental disorders. Although the mechanisms by which peripheral immunity may influence neuronal function are largely unknown, recent findings implicate meningeal immunity influencing behavior, such as spatial learning and memory[1].

SUMMARY OF THE INVENTION

Applicants show that meningeal immunity is also critical for social behavior; mice deficient in adaptive immunity exhibit social deficits and hyper-connectivity of frontocortical brain regions. Associations between rodent transcriptomes from brain and cellular transcriptomes in response to T cell-derived cytokines suggest a strong interaction between social behavior and interferon-gamma (IFN-γ) driven responses. Concordantly, Applicants demonstrate that inhibitory neurons respond to IFN-γ and increase GABAergic currents in projection neurons, indicating that IFN-γ is a molecular link between meningeal immunity and neural circuits recruited for social behavior. Meta-analysis on the transcriptomes of a range of organisms revealed that rodents, fish, and flies elevate IFN-γ/JAK-STAT-dependent gene signatures in a social context, indicating that the IFN-γ signaling pathway mediates a coevolutionary link between social/aggregation behavior and an efficient antipathogen response. The studies provided herein implicate adaptive immune dysfunction, in particular IFN-γ, in disorders characterized by social dysfunction and suggest a coevolutionary link between social behavior and an anti-pathogen immune response driven by IFN-γ signaling.

The present disclosure provides method of treating social dysfunction neurological disorders in an animal subject comprising administering to the subject a therapeutically effective amount of a compound that increases STAT1 activity. The present disclosure further provides methods of treating seizures in an animal subject, comprising administering to the subject a therapeutically effective amount of a compound that increases STAT1 activity. In some embodiments the animal subject is a human. In some embodiments the compound comprises IFN-γ. In some embodiments the compound comprises STAT1. In some embodiments the compound increases STAT1 activity in GABAergic inhibitory neurons. In some embodiments the compound increases GABAergic transmission. In some embodiments the compound is a GABA receptor agonist and/or a positive allosteric modulator. In some embodiments the compound is a benzodiazepine compound. In some embodiments the compound is diazepam. Some embodiments further comprise identifying a subject in need of said treatment. In some embodiments the subject in need of said treatment is susceptible to or suffering from a social dysfunction neurological disorder selected from the group consisting of autism spectrum disorder (ASD), frontotemporal dementia, and schizophrenia. Some embodiments further comprise identifying a subject in need of said treatment, wherein said subject is susceptible to or suffering from seizures. In some embodiments the administration of the compound is into the cerebrospinal fluid (CSF) of said subject. In some embodiments an ointment comprises the compound and the administration is via application of the ointment to the head of said subject.

BRIEF DESCRIPTION OF THE DRAWINGS

FIGS. 1A-1H show that meningeal T cell compartment is necessary for supporting neuronal connectivity and social behavior. FIG. 1A shows that wild-type mice exhibit social preference that is absent in SCID mice (ANOVA for genotype (F (1, 26))=6.370, P=0.0181; n=14 mice per group; P<0.01 Sidak's posthoc; pooled 2 independent experiments). FIG. 1B shows that repopulating the adaptive immune system in SCID mice restored normal social behavior (n=17;16;15 mice per group; ANOVA for genotype (F (2, 45))=8.282, P=0.0009 and interaction (F (2, 45))=9.146, P=0.0005; *P<0.001; **P<0.01 Sidak's post-hoc; pooled 3 independent experiments). FIG. 1C, shows correlation matrices from wild-type, SCID, and repopulated (Repop.) SCID mice were generated by rsfMRI. Abbrev.: L=left; R=right; FrA=frontal association area; PrL=prelimbic cortex; Ins=insula; OrbC=orbital cortex. FIG. 1D shows correlation values from rsfMRI. The box and whisker plots extend to the 25th and 75th percentiles with the centerline showing the mean. The whiskers represent the min and max data points. (n=8;9;4 mice per group; ANOVA<0.05; *P<0.05 Sidak's post-hoc; pooled 2 independent experiments). FIG. 1E shows immunohistochemistry of c-fos in the PFC. FIG. 1F shows elevated c-fos+ cells in the prefrontal and orbital cortices of SCID compared to wild-type mice (n=9; 10 mice per group; **P<0.01; *P<0.05 t-test; single experiment). FIG. 1G shows acute partial depletion of meningeal T cells caused social deficits (n=12;13 mice per group; ANOVA for interaction (F (1, 23))=7.900, P<0.01; ***P<0.001 Sidak's post-hoc; pooled 2 independent experiments). FIG. 1H, shows a circos plot showing the connectivity map derived from the pairwise comparison of transcriptome datasets. IFN-γ signature genes are over represented in cortex of animals exposed to social aggregation and psychostimulants. The representations of IFN-γ, IL-4/IL-13, IL-17, and IL-10/TGF-β dataset connectivity are shown in orange, green, blue, and purple, respectively. Each line represents a pairwise dataset overlap, which was determined using GSEA analysis and filtered by P<0.05 and NES>1.5. See FIG. 8 for labels. Data from the 3-chamber test (a, b, g) were analyzed by applying a 2-way ANOVA for social behavior and genotype/treatment, followed by a post-hoc Sidak's test. Bars represent average mean times investigating±s.e.m.

FIG. 2A shows that Ifng−/−mice exhibit social deficits (n=16;12 mice per group; ANOVA for genotype (F (1, 52))=8.327, P<0.01; **P<0.01 Sidak's post-hoc; pooled 2 independent experiments). FIG. 2B shows a correlation matrix from Ifng+/+ and Ifng−/− mice. FIG. 2C shows box and whisker plots of correlation values (n=8 mice per group; *P<0.05; #P=0.06 t-test; repeated 2 times). FIG. 2D shows that a single CSF injection of IFN-γ (20 ng) was sufficient to rescue social deficits in Ifng−/− mice 24 hours post-injection (n=14;11 mice per group; ANOVA for interaction (F (1, 46))=10.22 P<0.01; ***P<0.001 Sidak's post-hoc; pooled 2 independent experiments). FIG. 2E shows expression of IFN-γ receptor subunit mRNA by fluorescent in situ hybridization in slices from mouse PFC. RNA probes and corresponding colors: left: psd95-blue (neurons); right: CD11B-blue (microglia); top: IFNGR 1-red; bottom: IFGR2-red. Yellow arrowheads denote co-localization. FIGS. 2F and 2M show expression of IFN-γ receptor subunit protein by flow cytometry. Cells were gated on Hoechst+/live/single then neurons and microglia were gated on NeuN and CD11B, respectively. Ifngr1−/− mice and no primary antibody for IFNGR2 were included as negative controls. FIG. 2G shows that deleting Ifngr 1 from neurons in the PFC caused social deficits. Ifngr1 fl/fl mice were injected with AAV-Syn-CRE-GFP into the PFC and tested for social behavior 3 weeks post injection (n=11;12 mice per group; ANOVA for genotype (F (1, 21))=10.62, P<0.01; *P<0.05 Sidak's post-hoc; pooled 3 independent experiments). FIG. 2H shows that VgatCre::STAT1 fl/fl mice exhibit social deficits (n=10;11 mice per group; ANOVA for interaction (F (1, 19))=10.30<0.01; *P<0.001 Sidak's post-hoc; pooled 3 independent experiments). FIG. 2I shows that layer 2/3 neurons in slices from wild-type mice are held under tonic GABAergic inhibition (top), which is blocked by the GABA-A receptor antagonist bicuculline. IFN-γ increases tonic GABAergic inhibitory current (n=11 cells from 4 mice; bottom). FIG. 2J shows that holding current pre and during IFN-γ (P=0.01 t-test). FIG. 2K, IFN-γ increased latency to reach each seizure stage (n=6 mice per group; ANOVA with repeated measures <0.001; *P<0.001 Sidak post-hoc) and (inset) reduced the maximum severity of seizures (*P<0.001 t-test; repeated 2 times). FIG. 2L shows that diazepam rescued social deficits in Ifng−/− mice (n=12 mice per group; ANOVA for interaction (F (1, 22))=9.204<0.01; P<0.01 Sidak's post-hoc; repeated 2 times). Data from the 3-chamber test (FIGS. 2A, 2D, 2G, 2H, and 2L) were analyzed by applying a 2-way ANOVA for social behavior and genotype/treatment, followed by a Sidak's posthoc test. Bars represent average mean times investigating±s.e.m. All experiments were repeated at least once.

FIGS. 3A-3L show over-representation of IFN-γ transcriptional signature genes in social behavior-associated brain transcriptomes of rat, mouse, zebrafish, and *drosophila*. GSEA plots demonstrate the over-representation of IFN-γ transcriptional signatures (derived from Molecular Signature Database C2, GSE33057, or Lopez-Munoz, A. et al 30) in brain transcriptomes of (FIGS. 3A-C) mice and (FIGS. 3D-3F) rats subjected to social or isolated housing and in brain transcriptomes of (FIGS. 3G-3I) domesticated zebrafish compared to a wild zebrafish strain. FIGS. 3J-3L shows over-representation of JAK/STAT pathway transcriptional signature genes (derived from GSE2828) in head transcriptomes of flies selected for low-aggressive behavior (behavioral readout for social behavior in flies (see methods section "Meta-data analysis" for more details)). Genes are ranked into an ordered list according to their differential expression. The middle part of the plot is a bar code demonstrating the distribution of genes in the IFN-γ transcriptional signature gene set against the ranked list of genes. The list on the right shows the top genes in the leading edge subset. Promoter regions of these genes were scanned for transcription factor binding site (TFBS) using MEME suite. MEME output demonstrates significant STAT TFBS enrichment in cis regulatory regions of leading edge genes up-regulated in a social context.

In FIG. 4A the 3-chamber sociability assay was used to test social behavior. FIG. 4B shows that neither wild-type nor SCID mice had a side bias in the habituation phase (empty cups) of the 3-chamber assay (n=6). FIG. 4C, There was no effect of genotype on distance traveled in the 3-chamber assay during the habituation phase (n=6). FIG. 4D shows that both wild-type and SCID mice had an olfactory preference to urine, suggesting normal olfactory behavior (n=8 mice per group; ANOVA for urine preference F (1, 28)=31.01; P<0.0001; * P<0.001,  P<0.01 Sidak's post-hoc). FIG. 4E shows percent time spent in the open arms of plus-maze (n=22 mice per group). FIG. 4F shows the number of entries into the open arms of the plus-maze (n=22 mice per group). FIG. 4G shows the total arm entries of plus-maze (n=22 mice per group). FIG. 4H shows the percent time spent in the center of the open field (n=22 mice per group). FIG. 4I shows the total ambulatory distance in the open field (n=22 mice per group). FIG. 4J shows the latency to fall off the accelerating rotarod (n=8 mice per group). FIG. 4K shows that SCID mice spent less time investigating each other than wildtype mice spent investigating each other when placed into a novel social environment (n=5 mice per group; repeated-measures ANOVA for genotype F (1, 21)=5.708* P<0.05). FIGS. 4L-4O show that repopulated SCID mice have similar numbers (FIG. 4P) and percentage (FIG. 4Q) of meningeal T cells as wild-type mice (n=4-5 mice per group). Cells were gated on singlets, live, CD45+, and TCR.

In FIGS. 5A-5F regions of interests (ROIs) were generated using "The Mouse Brain" by Paxinos and Franklin as a reference. Abbreviations are as follows: FrA=frontal association cortex; PrL=prelimbic cortex; OrbC=orbital cortex; OB=olfactory bulb; MC=motor cortex; SocC=somatosensory cortex; Ins=insula; PirF=piriform cortex; CpU=caudate putamen; Acb=accumbens; ACC=anterior cingulate cortex; dHip=dorsal hippocampus; T=thalamus; Amyg=amygdala; EntC=entorhinal cortex; Hyp=hypothalamus; VisC=visual cortex; SupC=superior colliculus; PAG=periductal grey; DpMe=deep mesencephalic nucleus; vHip=ventral hippocampus; SNR=substantia nigra; VTA=ventral tegmental area; CB=cerebellum; BS=brain stem. FIGS. 5G-5I show the connectivity of local PFC/Insular nodes. Correlation thresholds were applied to visualize the strength of the connection. Connections that pass a high threshold are shown in red; connections that pass a lower threshold are shown in dashed grey. SCID mice have aberrant hyper-connectivity in the PFC (n=8-9 mice per group; P<0.05 Jennrich test). FIG. 5J shows c-fos+ cells in the hippocampus (n=9-10 mice per group).

FIGS. 6A-6B show that anti-VLA4 depletes meningeal T cells. Meninges were dissected and single cell suspensions were immune-stained. T cells were gated on live, single, CD45+, TCR+ events and counted by flow cytometry. FIG. 6C shows that acute injection of anti-VLA4 reduced the amount of TCR+ T cells in the meninges (n=4 mice per group; * P<0.01).

FIGS. 8A-8C show that a substantial percentage of meningeal T cells produce IFN-γ. Cells were gated for live, singlets, CD45+, and TCR+. Ifng−/− mice were used to gate for IFN-γ staining. FIG. 8D shows the percent time spent in open arms of the plus-maze (n=20 mice per group). FIG. 8E shows entries into the open arms of plus-maze (n=20 mice per group). FIG. 8F shows total entries into all arms of the plus-maze (n=20 mice per group). FIG. 8G shows the percent time spent in the center of the open field (n=20 mice per group). FIG. 8H shows the total ambulatory distance in the open field (n=20 mice per group). FIG. 8I shows the latency to fall off the accelerating rotarod (n=8 mice per group).

FIG. 9A shows that repopulating SCID mice with wild-type lymphocytes rescued a social preference; repopulating with Ifng−/− lymphocytes did not rescue a social preference; AVONA for Social behavior $F (1, 14)=11.99$; $P=0.0038$ ( $P<0.01$; n=8 mice per group). FIGS. 9B-9D shows the connectivity of local PFC/Insular nodes. Correlation thresholds were applied to visualize the strength of the connection. Connections that pass a high threshold are shown in red; connections that pass a lower threshold are shown in dashed grey. Ifng−/− mice have more connections than wild-type mice (Jennerich test; $P=0.0006$). These connections were reduced by IFN-γ (Jennerich test; $P=0.02$). FIG. 9E shows that Ifngr1 −/− mice have social deficits (n=6 mice per group; ANOVA for interaction $P=0.01$;  $P<0.01$ Sidak's post-hoc) that were not rescued by injecting IFN-γ into the CSF (FIG. 9F; n=5-6 mice per group; ANOVA for interaction $P=0.01$; ** $P<0.01$ Sidak's post-hoc). FIG. 9G, Il4−/−mice spend more time than wild-type mice investigating a novel mice; ANOVA for genotype $F (1, 32)=5.397$; $P=0.0267$ (* $P<0.05$ Sidak's posthoc; n=16-18 mice per group).

FIGS. 12A-12B, GFP fluorescence in the PFC. FIG. 12C, GFP fluorescence is only observed in Neu N+ neurons, not Iba+ microglia (top=20×; bottom 63× Objective).

In FIGS. 13A-13C IFN-γ was injected into the CSF (i.c.m.) 2 hours prior to sacrificing and processing brains for immunohistochemistry. Slices were stained for c-fos. FIG. 13D shows the total c-fos+ cells in layer I of the PFC (n=3 mice per group; * $P<0.05$). Holding current pre and post IFN-y application on acute slices from the PFC (FIG. 13E) and somatosensory cortex (FIG. 13F; n=6 neurons from 3 mice). c, VgatCre::Ifngr1fl/fl mice. IFN-γ increased tonic inhibition in Cre− mice (n=6-7 cells from 4 mice per group; ** $P<0.01$ Sidak's post-hoc test).

DEFINITIONS

Figure 1D:
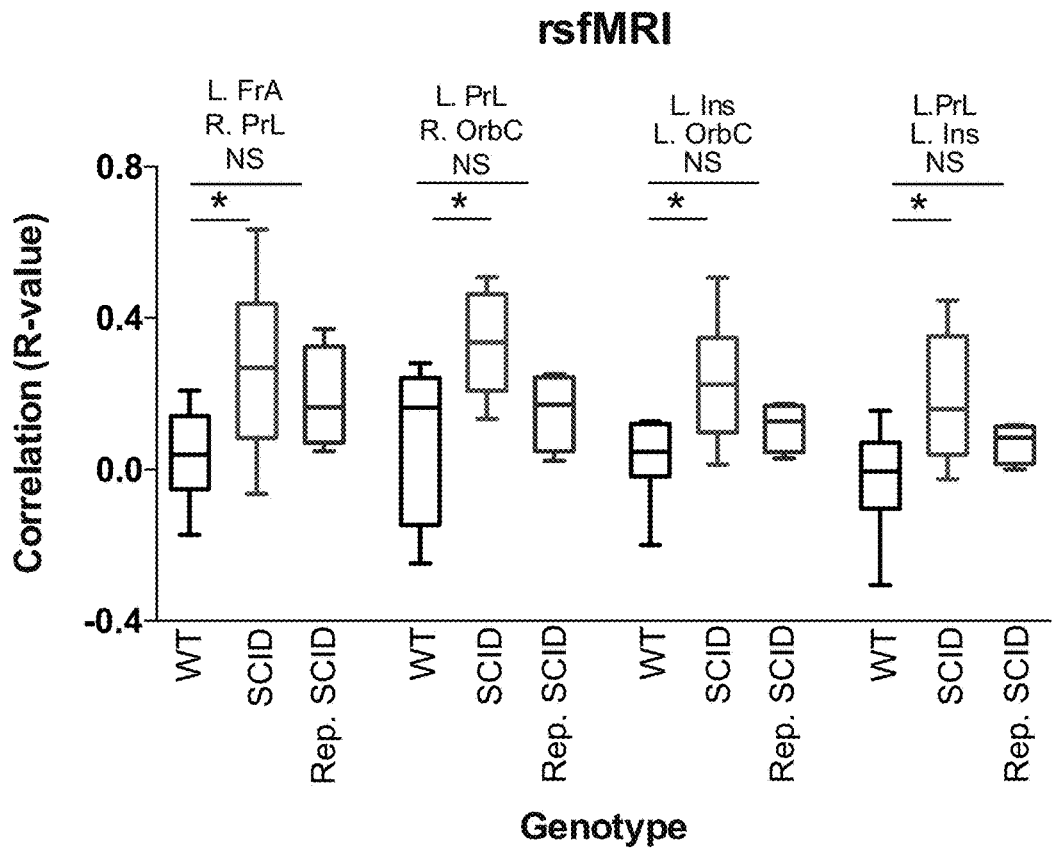

The present invention may be understood more readily by reference to the following detailed description of embodiments of the invention and the methods included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs as read in light of the specification.

The terms "treatment", "treating" and the like are used herein to have their ordinary meaning as understood in light of the specification, and generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein has its ordinary meaning as understood in light of the specification, and covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

As used herein, the singular forms "a," "an," and "the" include plural reference unless the context clearly dictates otherwise. Thus, for example, reference to "a reagent" is reference to one or more reagents and includes equivalents thereof known to those skilled in the art. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "about" has its ordinary meaning as understood in light of the specification, and is used herein to provide literal support for the exact number that it precedes, as well as a number differs from the given number by less than 10%. In some embodiments, the term "about"

indicates that the number differs from the given number by less than 9%, 8%, 7%, 6%, 5%, 4%, 3%, 2%, or 1%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

DETAILED DESCRIPTION

The present disclosure provides method of treating social dysfunction neurological disorders in an animal subject comprising administering to the subject a therapeutically effective amount of a compound that increases STAT1 activity. The present disclosure further provides methods of treating seizures in an animal subject, comprising administering to the subject a therapeutically effective amount of a compound that increases STAT1 activity.

Social behavior is beneficial for many processes critical to the survival of an organism, including foraging, protection, breeding, and for higher order species, mental health[2,3]. Social dysfunction manifests in several neurological and mental disorders such as autism spectrum disorder (ASD), frontotemporal dementia, and schizophrenia amongst others[4]. Likewise, imbalance of cytokines, a disparity of T cell subsets, and overall immune dysfunction is often associated with abovementioned disorders[5-7]. However, the fundamental mechanism(s) by which dysfunctional immunity may interfere with neural circuits and contribute to behavioral deficits remain unclear.

Figure 4A:
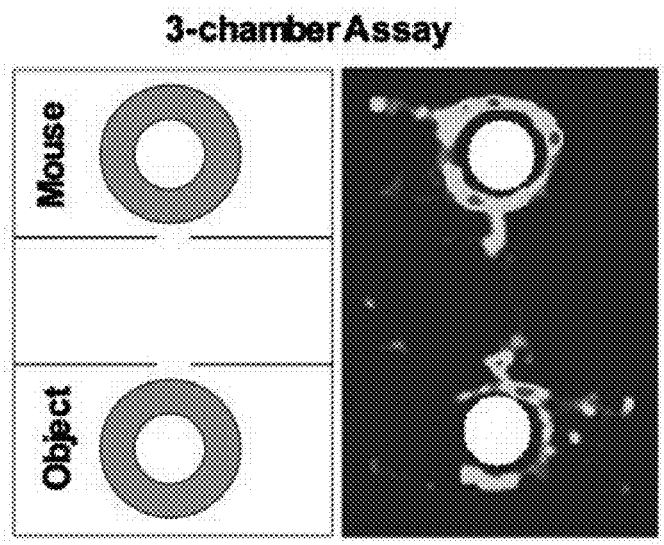
FIGS. 4A-4L show that SCID mice have no observable anxiety, motor, or olfactory deficits.
Figure 4B:
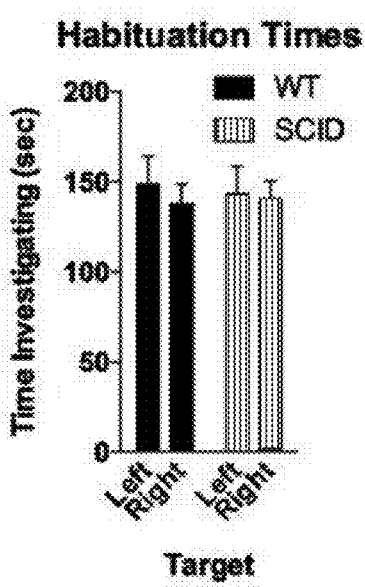
Figure 4C:
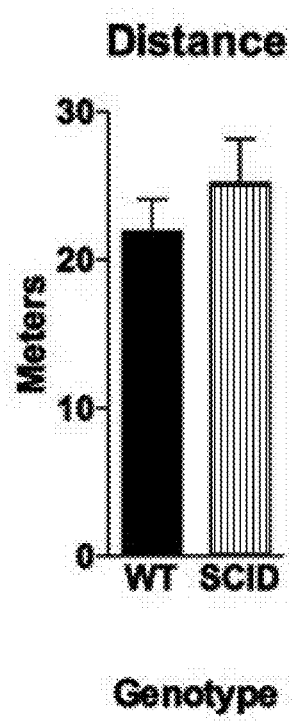
Figure 4D:
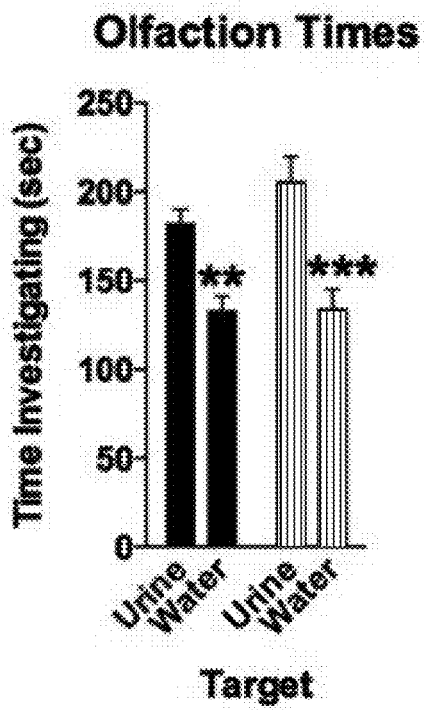
Figure 4E:
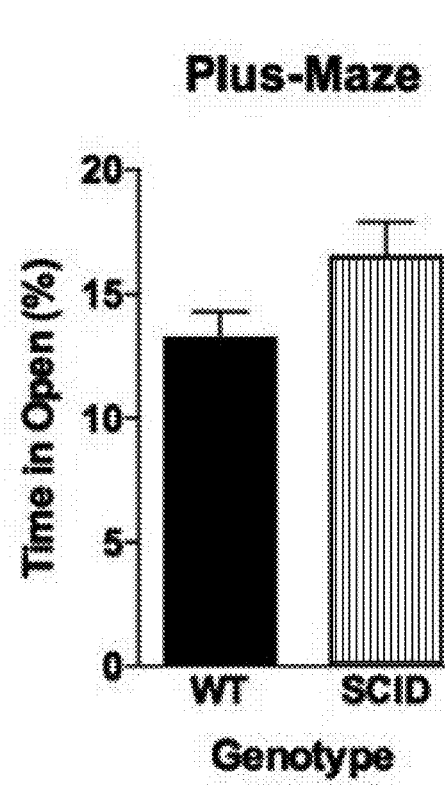
Figure 4F:
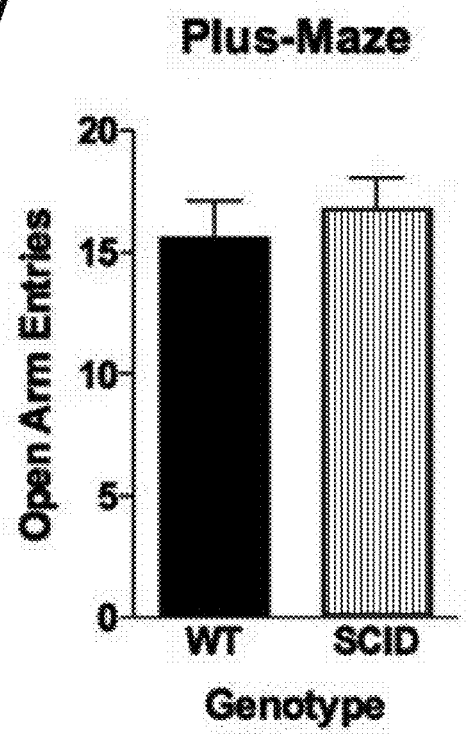
Figure 4G:
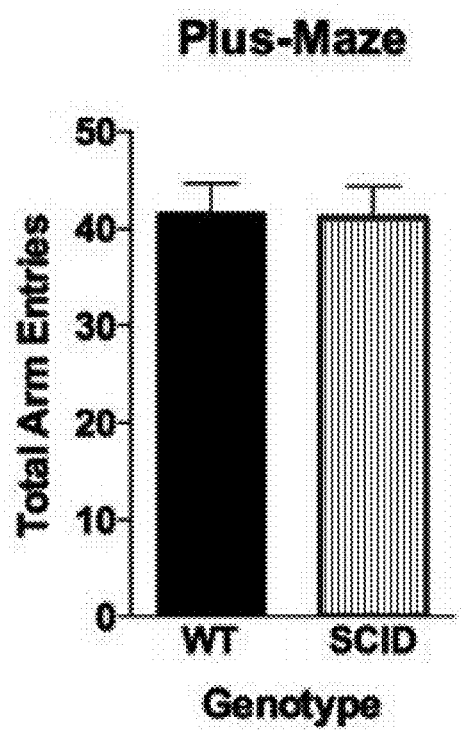
Figure 4H:
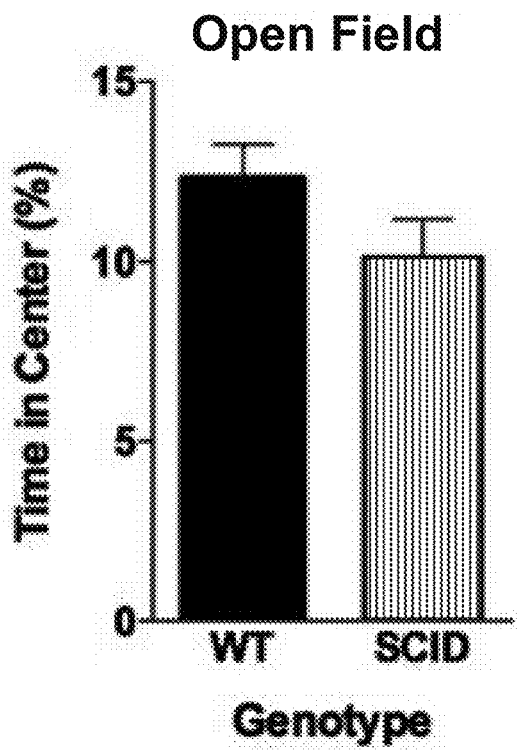
Figures 4I, 4J, 4K:
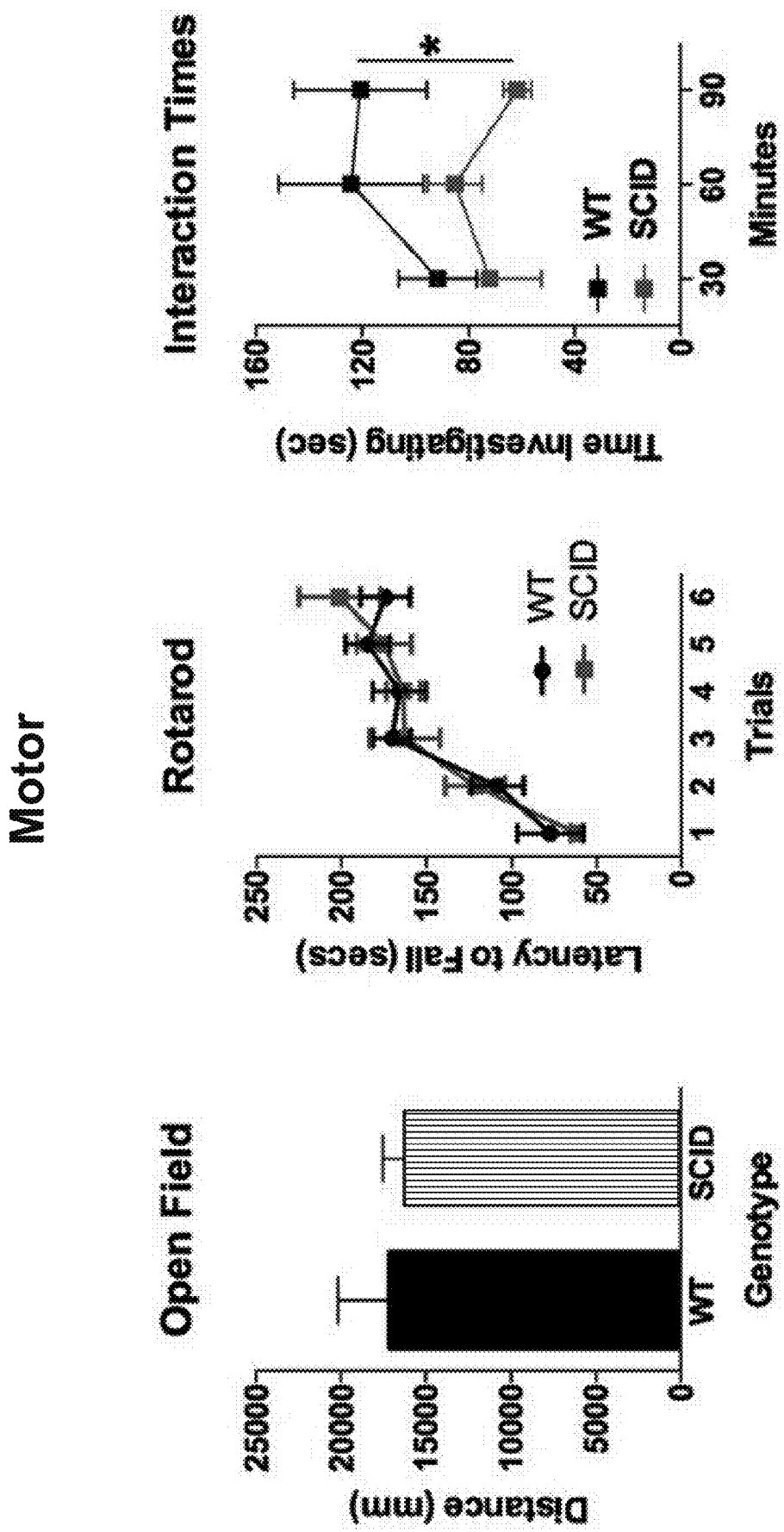
Figure 4L:
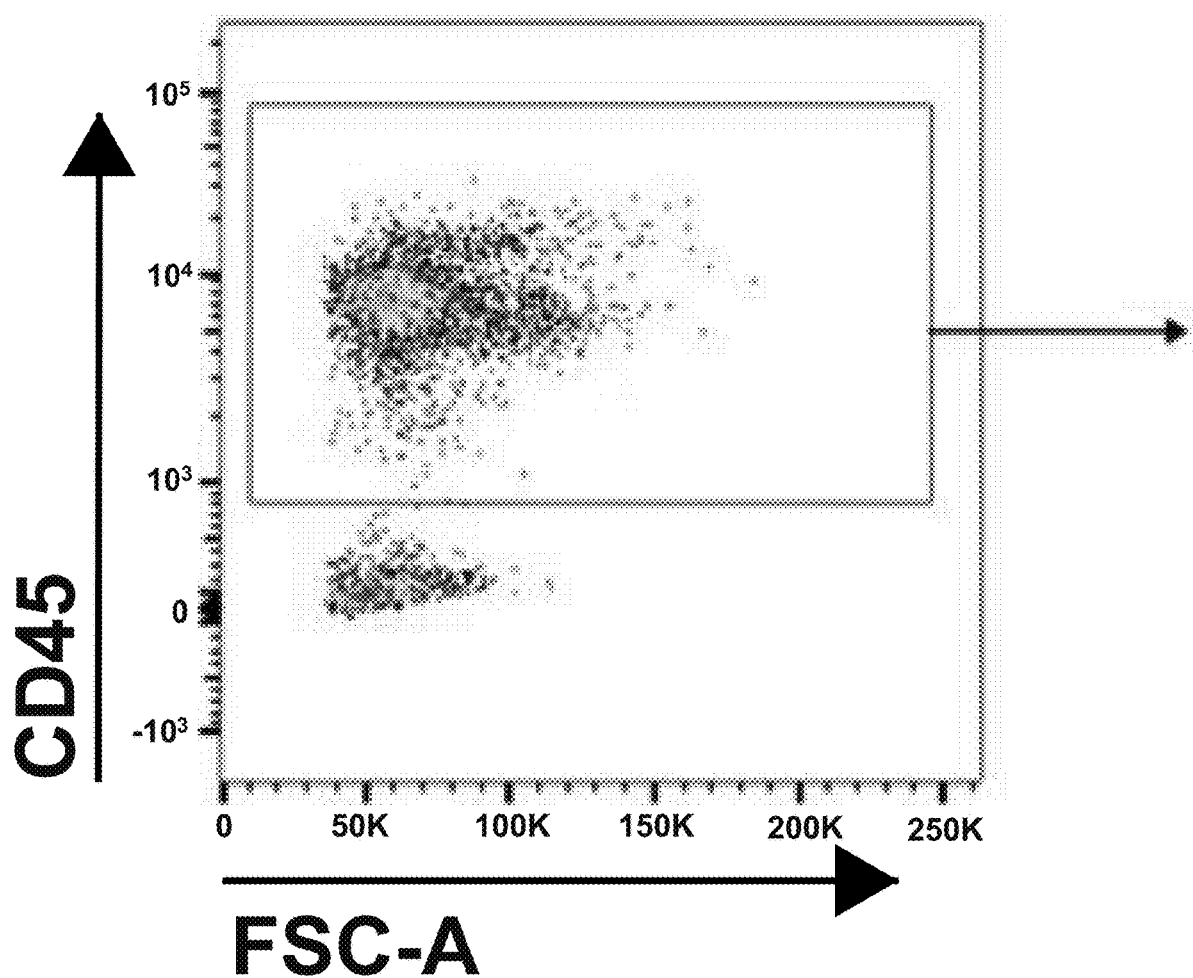
Figure 4M:
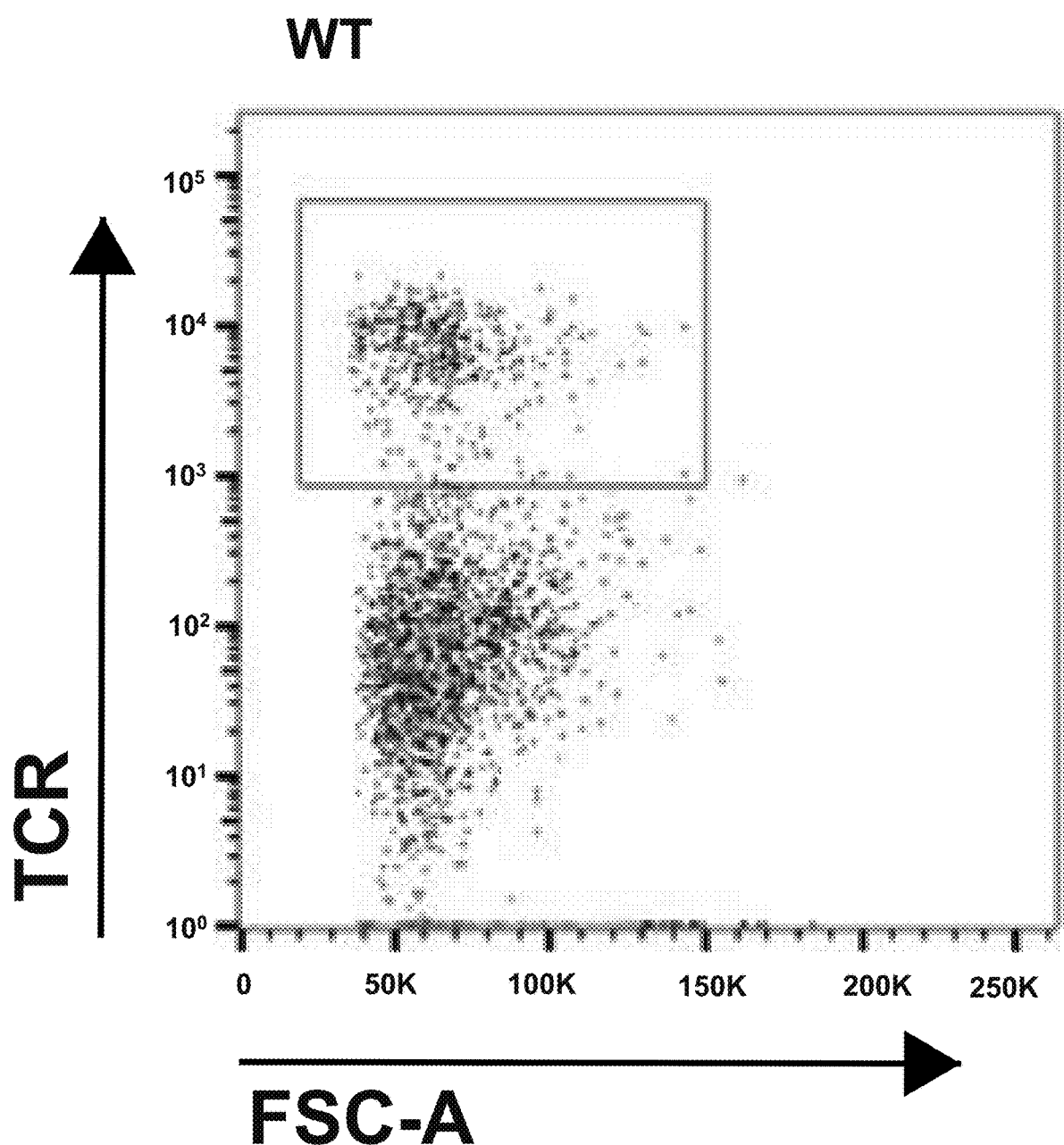
Figure 4N:
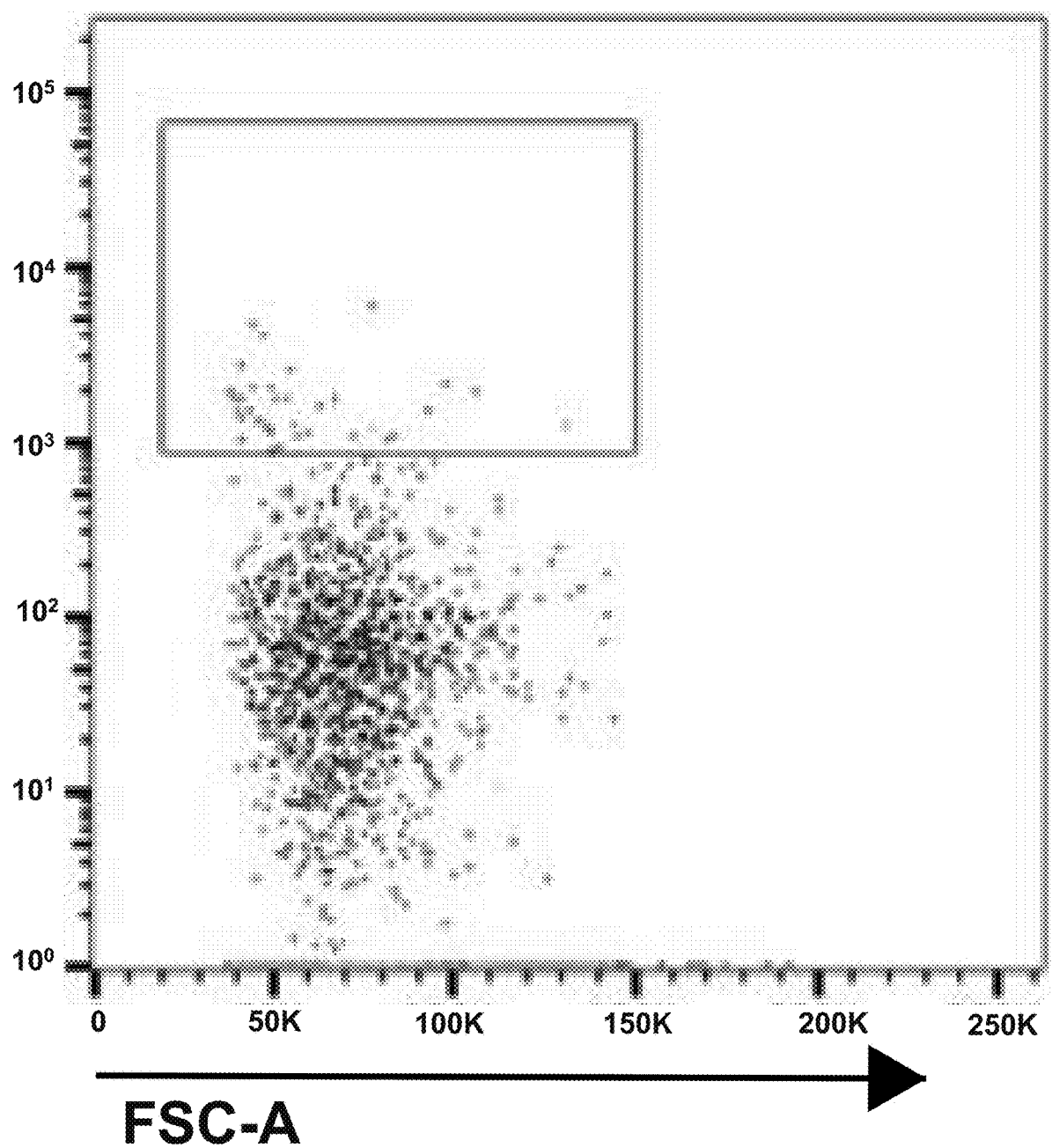
Figure 4O:
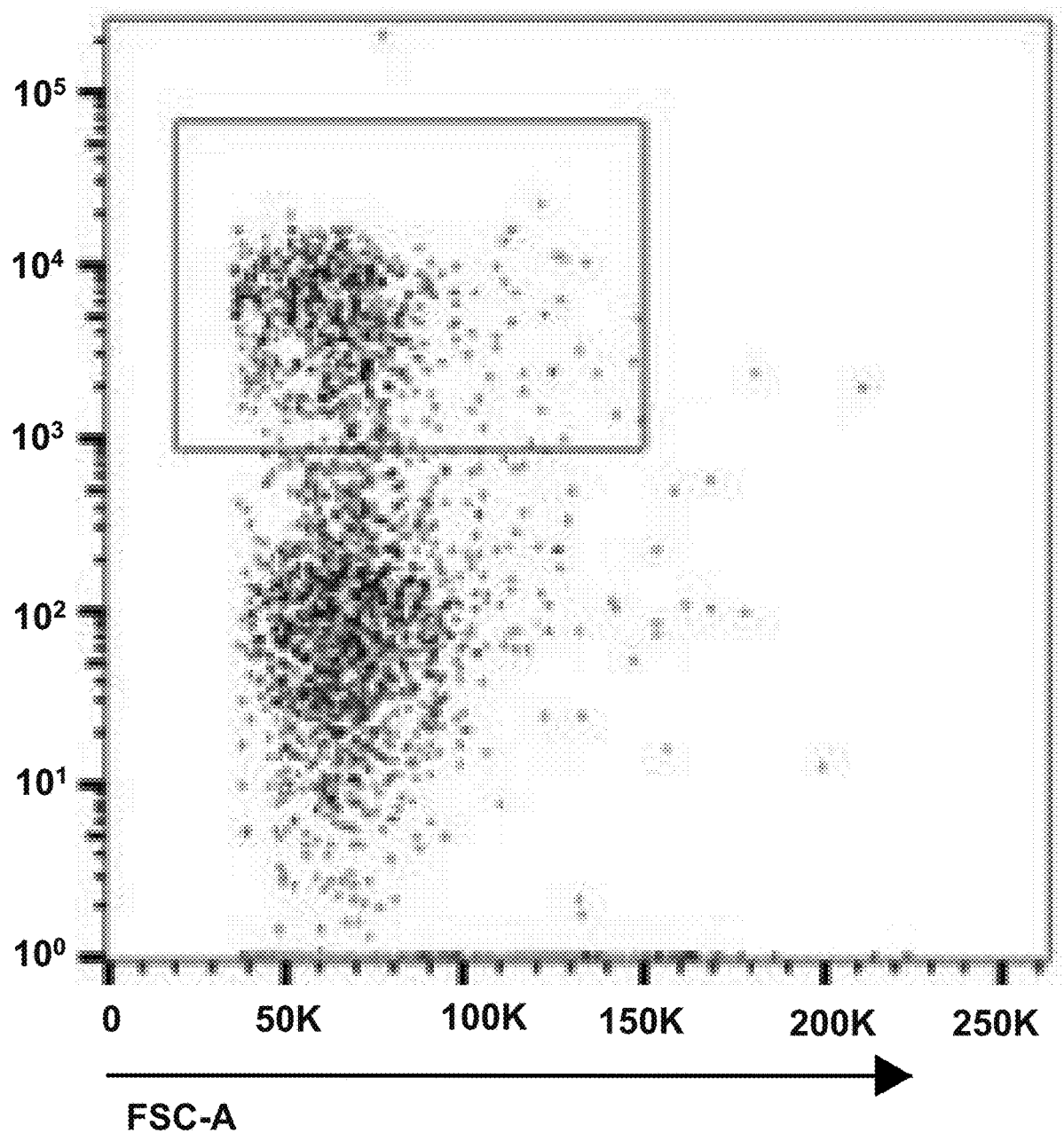
Figure 4Q:
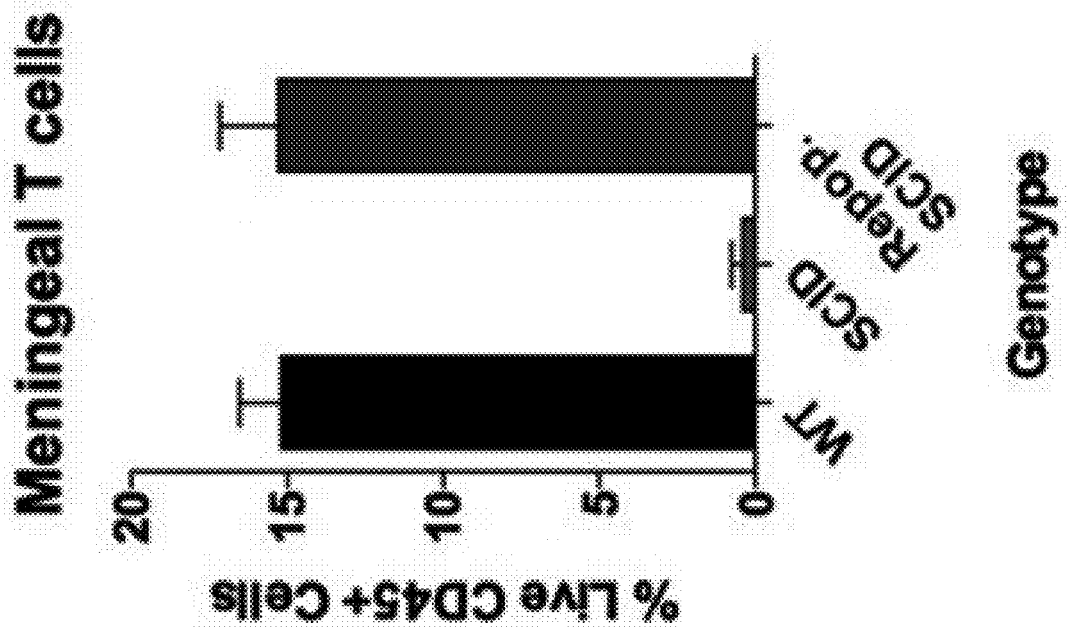
Figure 4P:
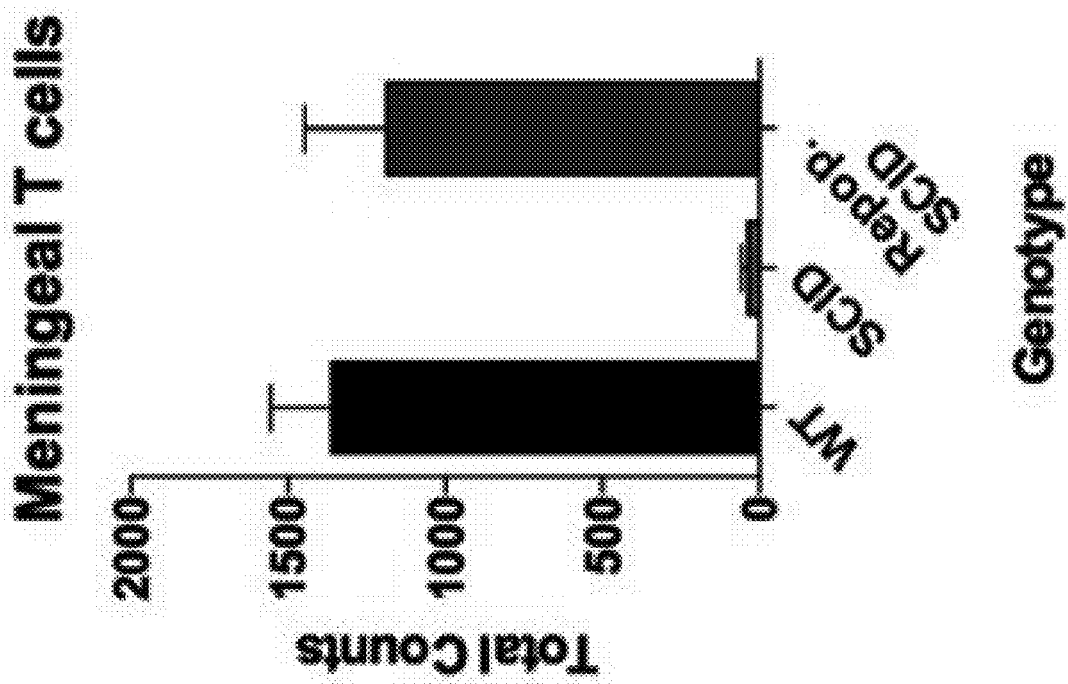

To test if adaptive immunity is necessary for normal social behavior, SCID mice (deficient in adaptive immunity) were tested using the 3-chamber sociability assay[8] (FIG. 4A). This assay quantifies the preference of a mouse for investigating a novel mouse versus object, and has been used to identify deficits in multiple mouse models of disorders that present with social dysfunction[9]. Unlike wild-type mice, SCID mice lacked social preference for a mouse over an object (FIG. 1A). Importantly, SCID mice did not show anxiety, motor, or olfactory deficits (FIGS. 4B-4J). It was confirmed that SCID mice have social deficits by analyzing social interactions in a home cage (FIG. 4K). To test if social deficits were reversible, 4-week-old SCID mice were repopulated with wild-type lymphocytes (FIGS. 4L-4Q) and social behavior was measured 4 weeks post transfer. SCID mice repopulated with lymphocytes, unlike those injected with the vehicle, showed social preference indistinguishable from wild-type mice (FIG. 1B).

Figure 1E:
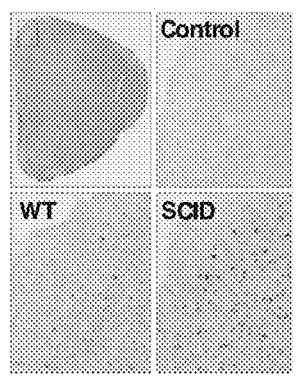
Figure 1F:
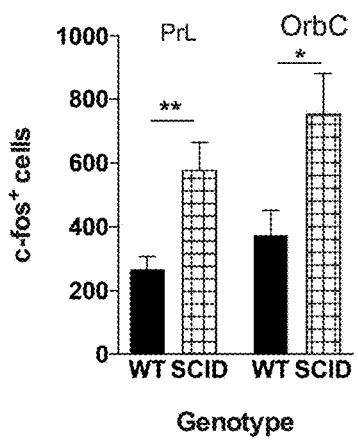
Figure 5A:
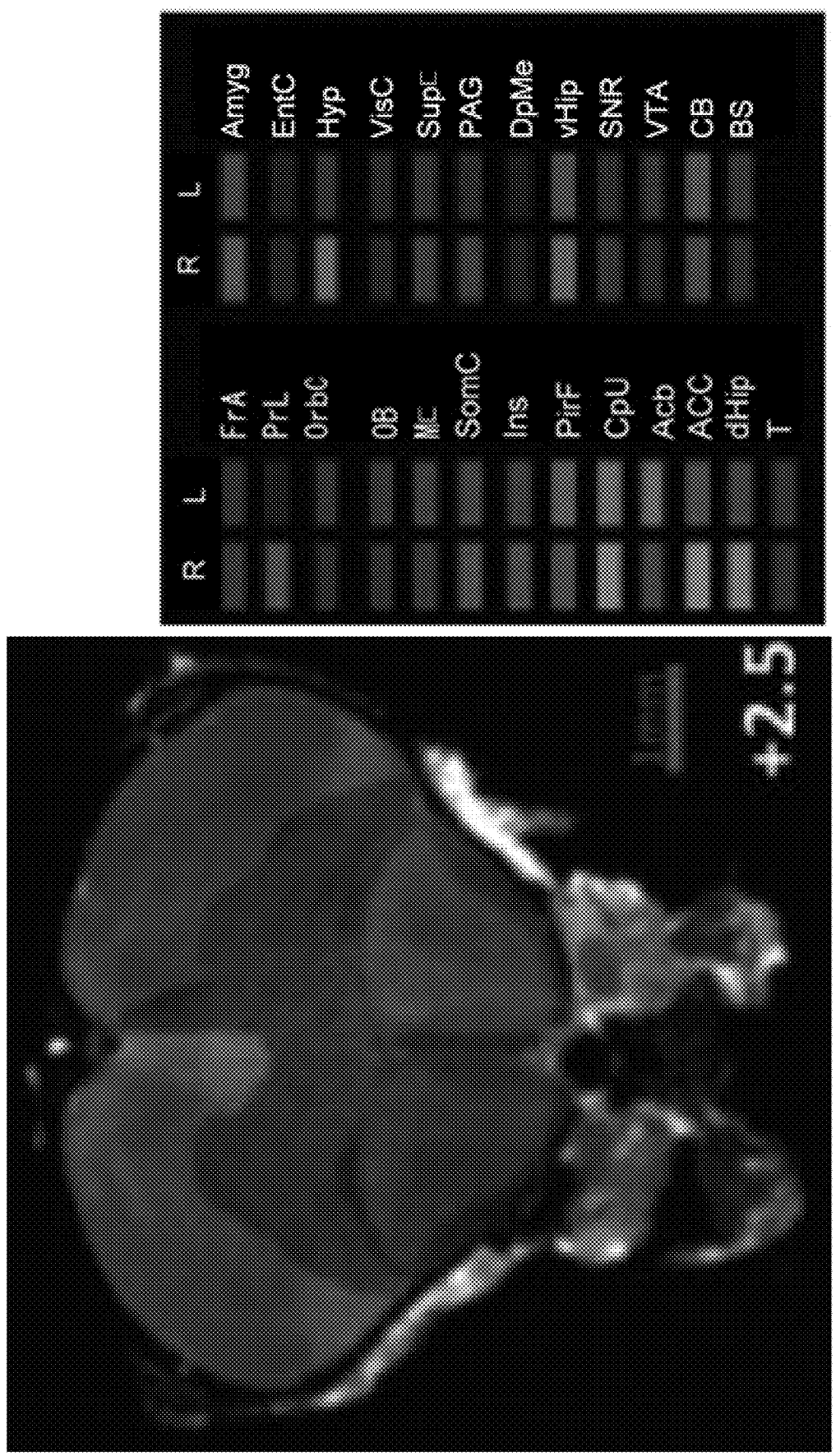
FIGS. 5A-5J show Neuroanatomical Structures analyzed by rsfMRI.
Figure 5B:
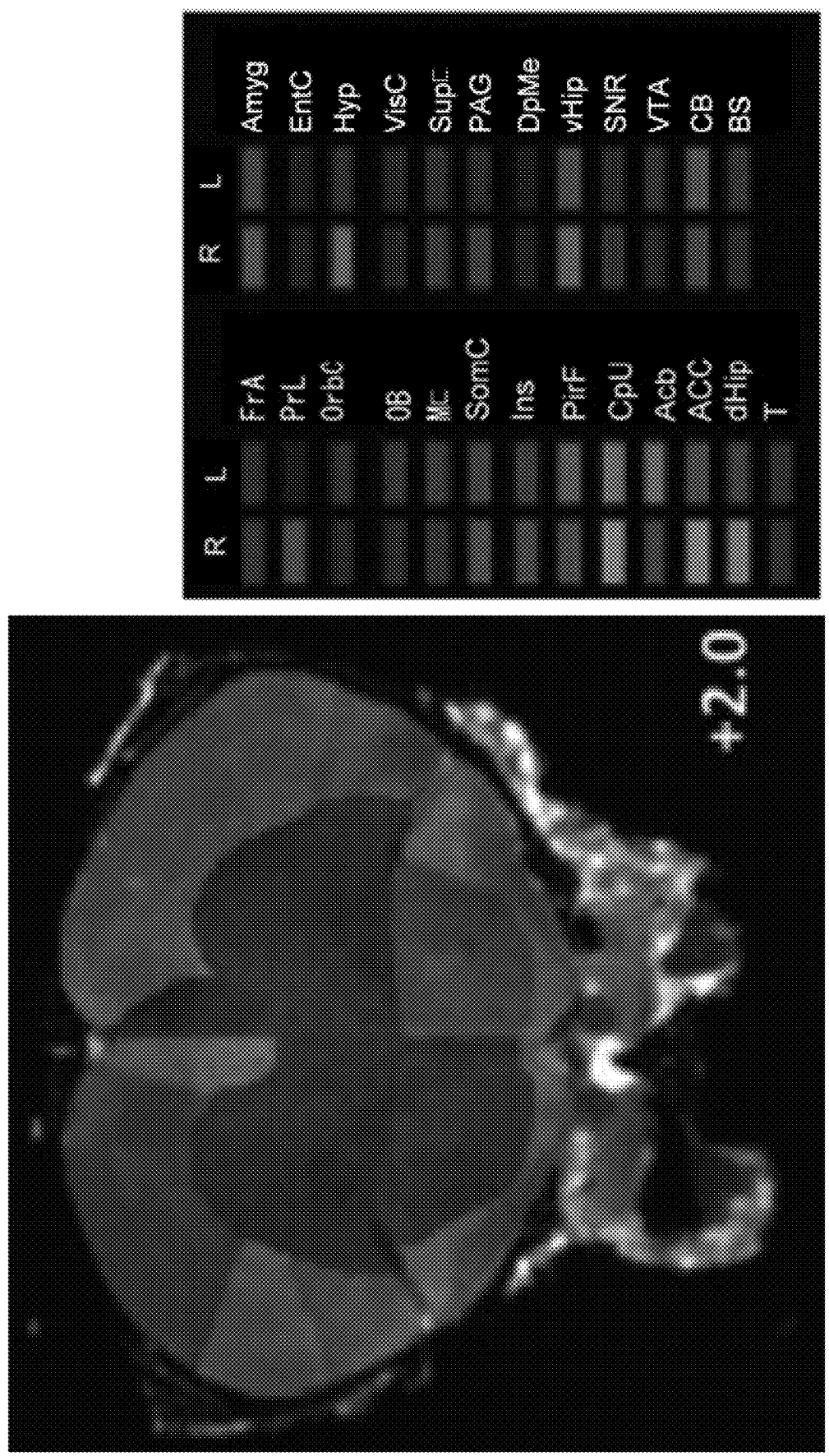
Figure 5C:
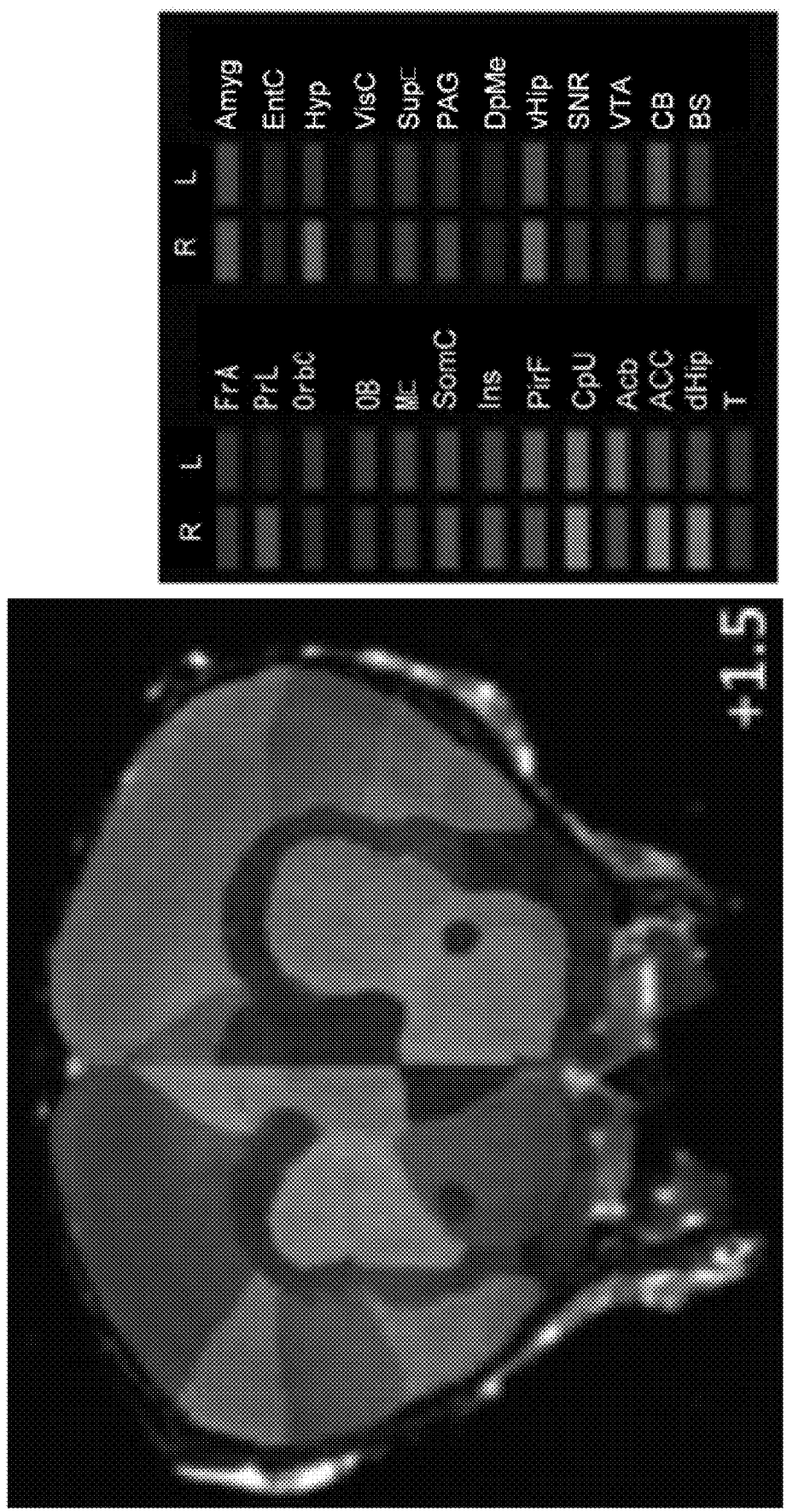
Figure 5D:
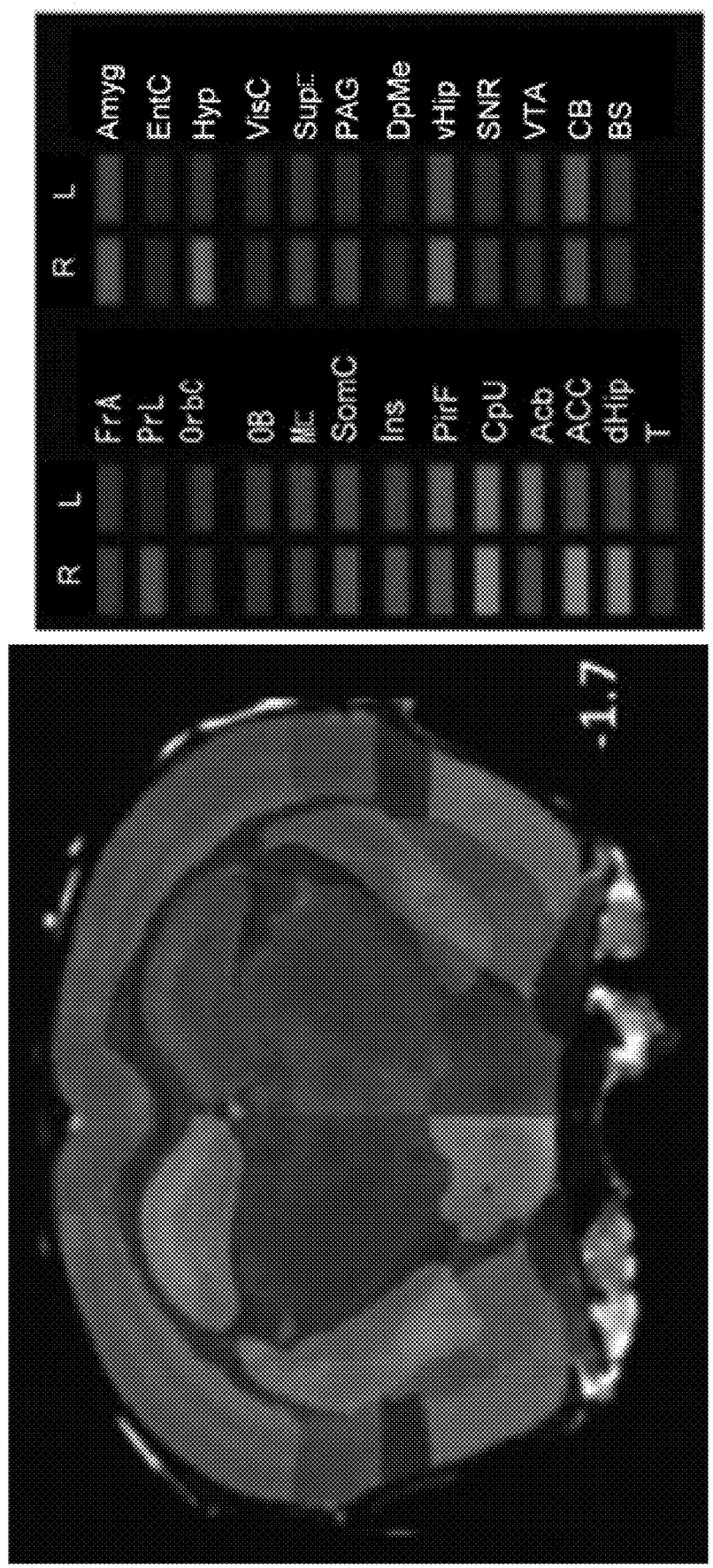
Figure 5E:
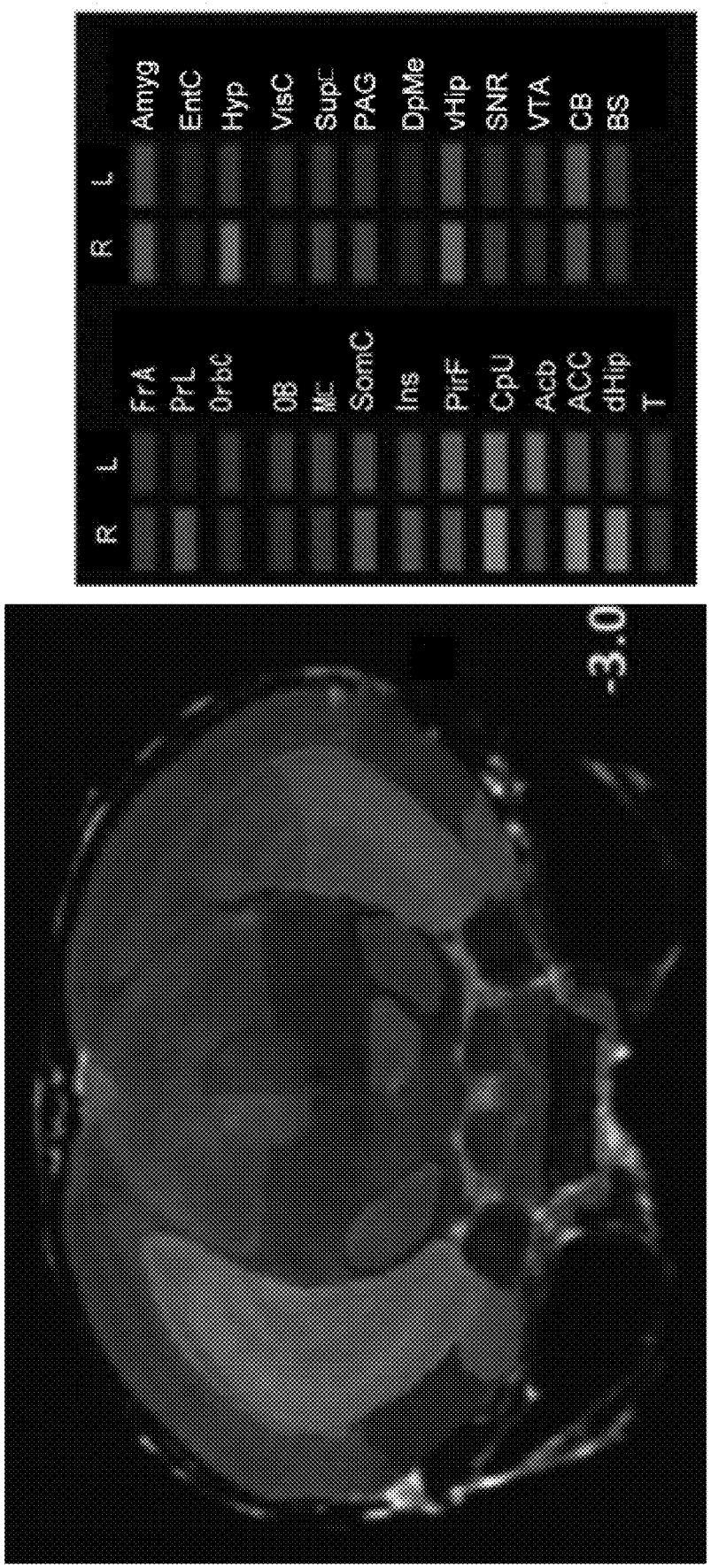
Figure 5F:
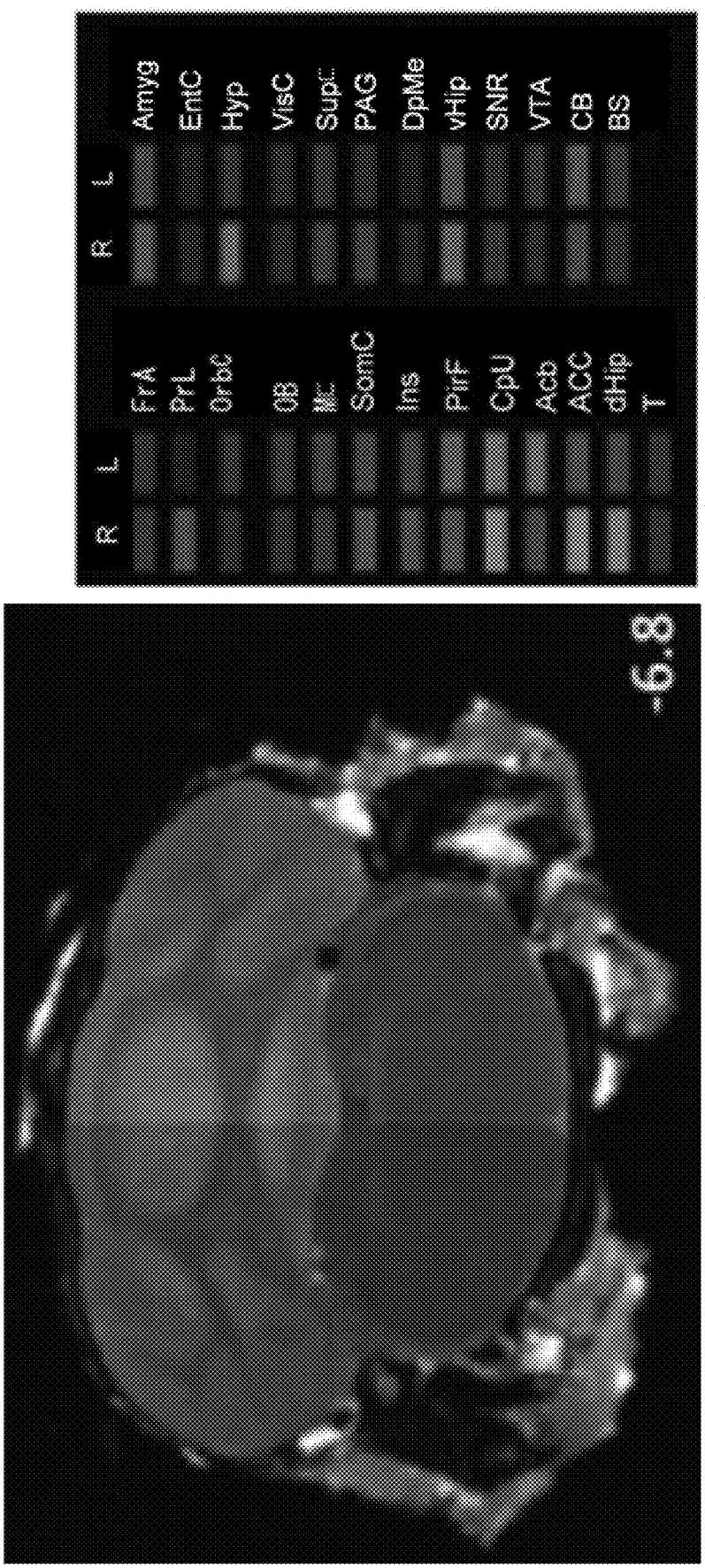
Figure 5J:
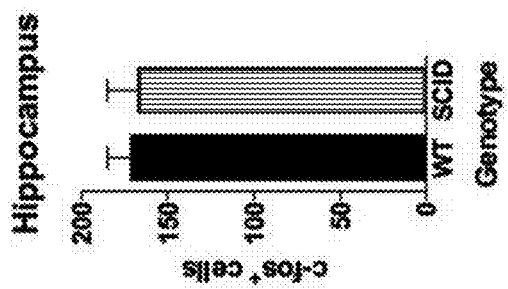
Figure 5I:
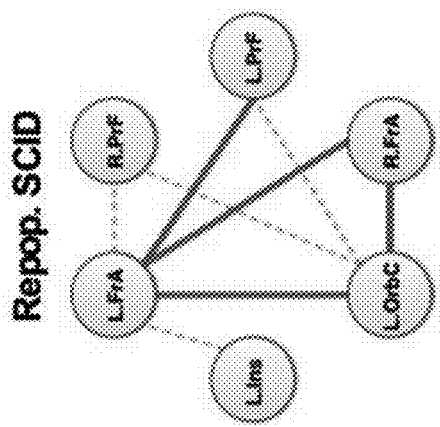
Figure 5H:
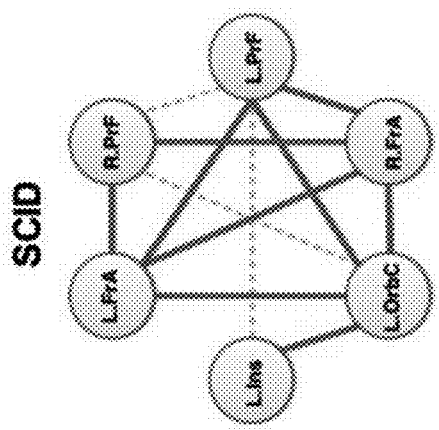
Figure 5G:
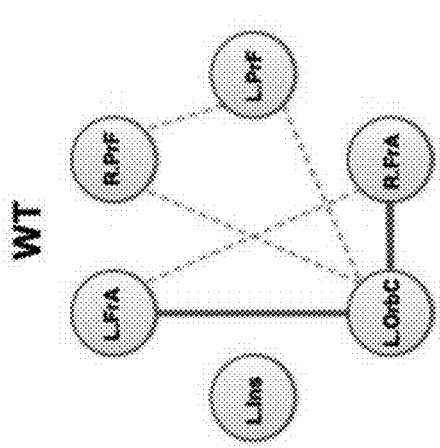

Recent clinical findings indicate disturbed circuit homeostasis, resulting in hyperconnectivity, is a feature of children with ASD[10]. Imaging studies using task-free resting state fMRI (rsfMRI), revealed hyper-connectivity among frontal cortical nodes in ASD patients[11]. Disturbances in resting state connectivity are also observed in mice with social deficits[12]. rsfMRI is an unbiased technique used to assess synchrony between brain regions over time by comparing spontaneous fluctuations in blood oxygenation level dependent (BOLD) signals[13]. To assess the influence of adaptive immunity on functional connectivity, resting-state BOLD signals from wild-type and SCID mice were analyzed (FIGS. 5A-5F). SCID mice exhibited hyper-connectivity between multiple frontal and insular regions (FIG. 1E, 1D; FIGS. 5G-5I; Supplement Table 1) implicated in social behavior and ASD. Notably, repopulating SCID mice with lymphocytes rescued aberrant hyper-connectivity observed in vehicle-treated SCID controls (FIGS. 1E, 1D; FIGS. 5G-5I). Interestingly, other functionally connected regions, not directly implicated in social function, such as interhemispheric connectivity between motor and somatosensory cortex were not affected by a deficiency in adaptive immunity (Supplement Table 1). Using another approach to analyze neuronal activation in a task-based system, it was demonstrated that SCID mice exposed to a social stimulus exhibited hyper-responsiveness in the prefrontal cortex (PFC; increased number of c-fos+ cells in PFC; FIGS. 1E, 1F) but not the hippocampus (FIG. 5J).

Figure 1G:
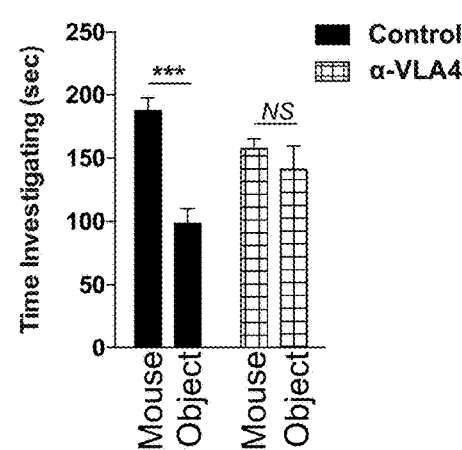
Figure 1H:
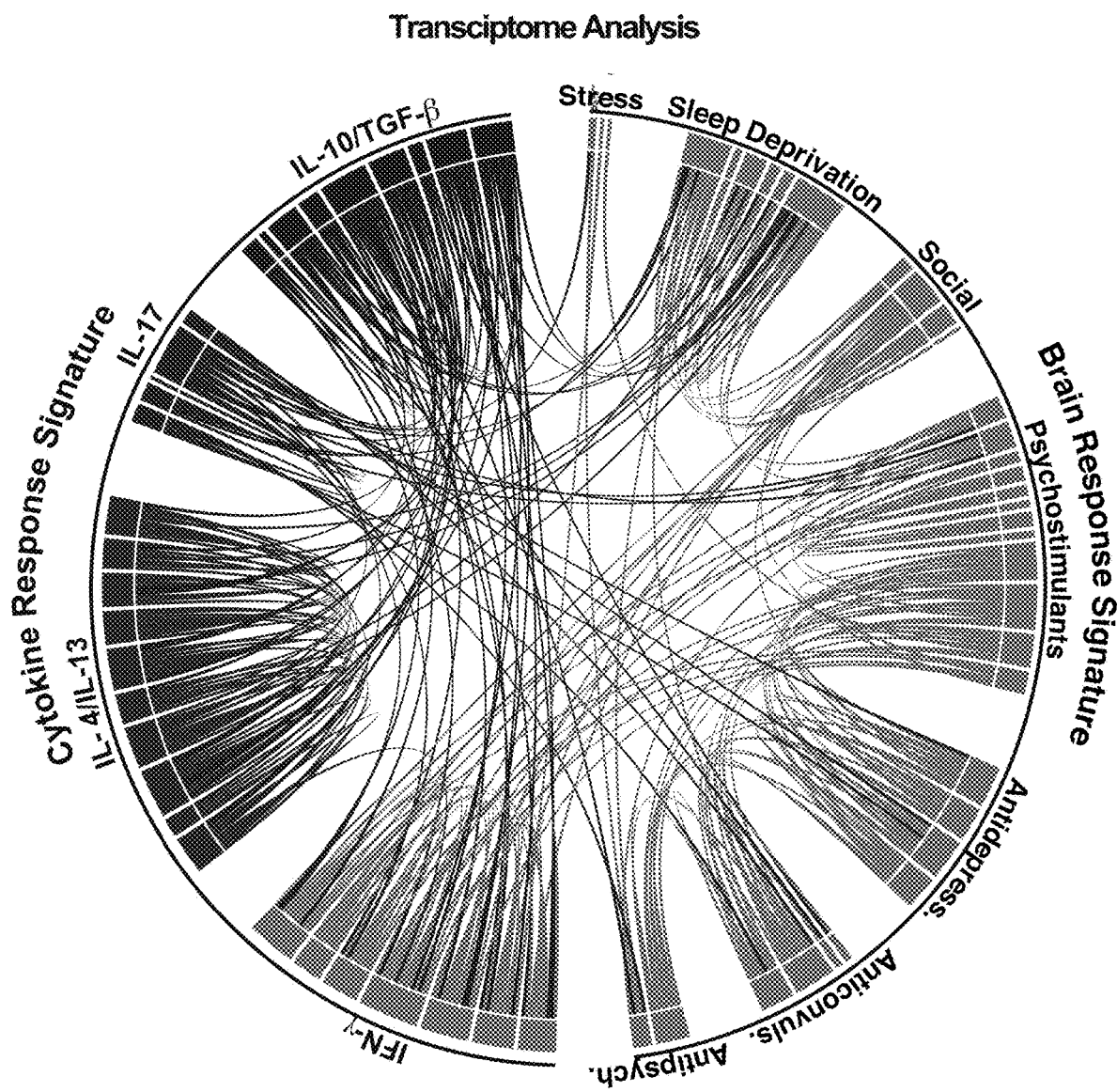
Figure 6A:
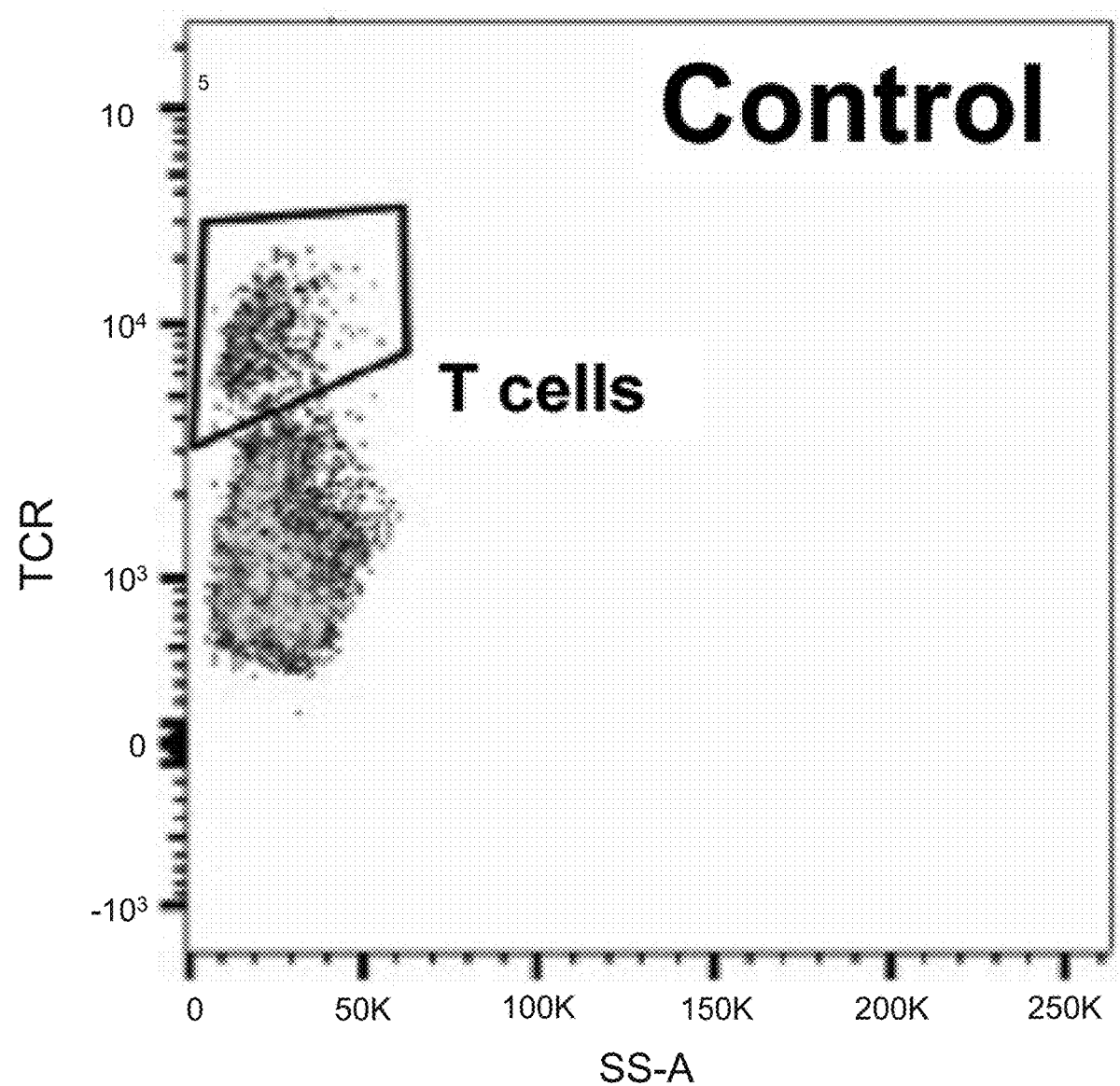
FIGS. 6A-6C show acute reduction of meningeal T cells with anti-VLA4.
Figure 6B:
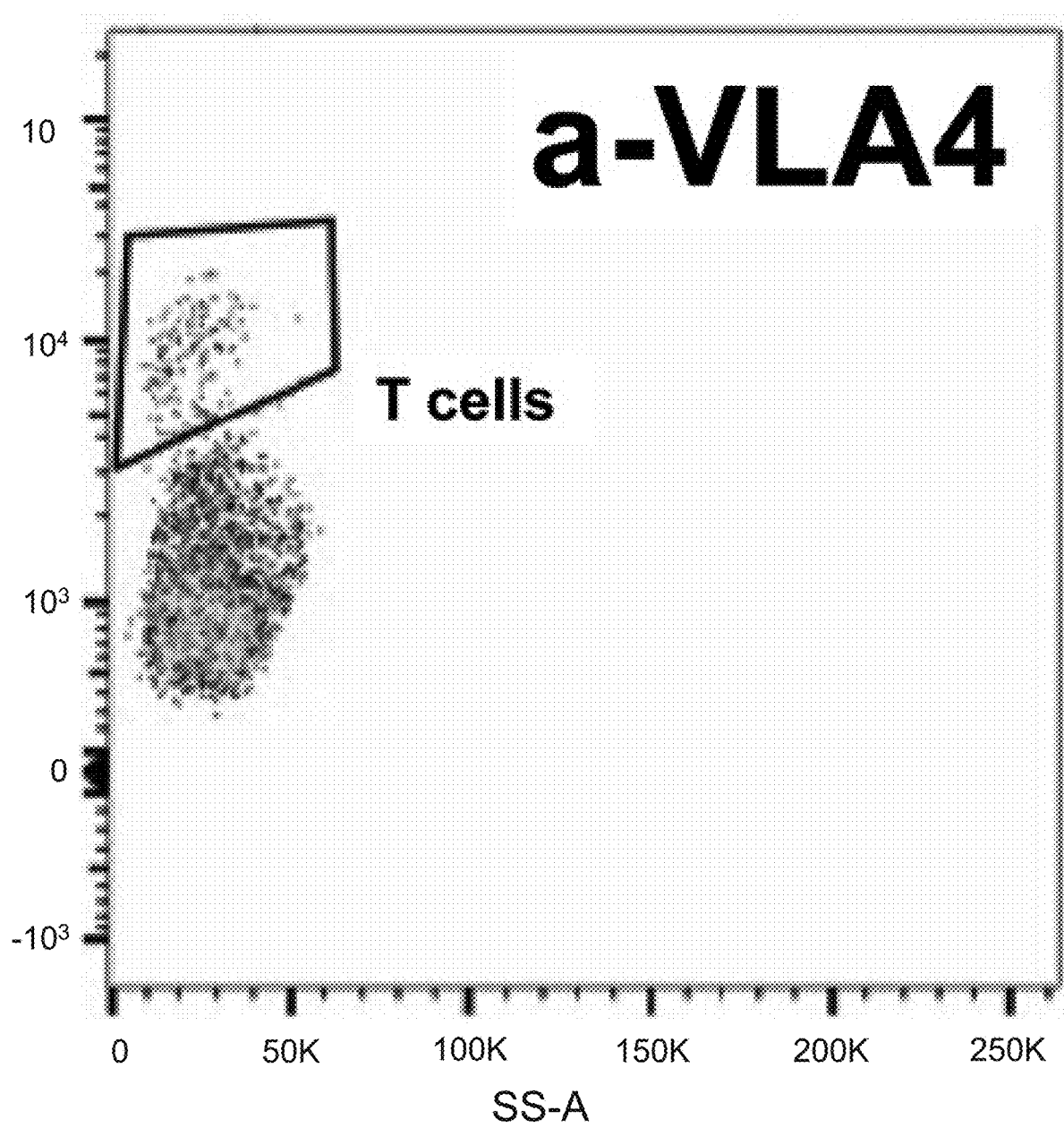
Figure 6C:
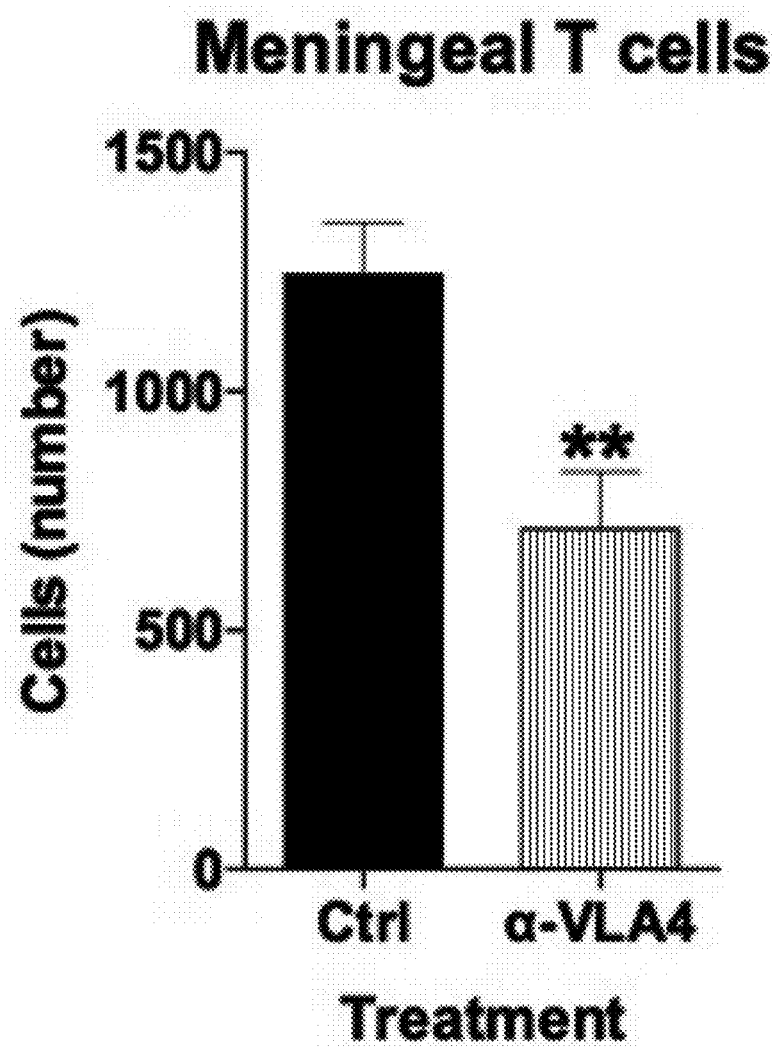
Figure 7:
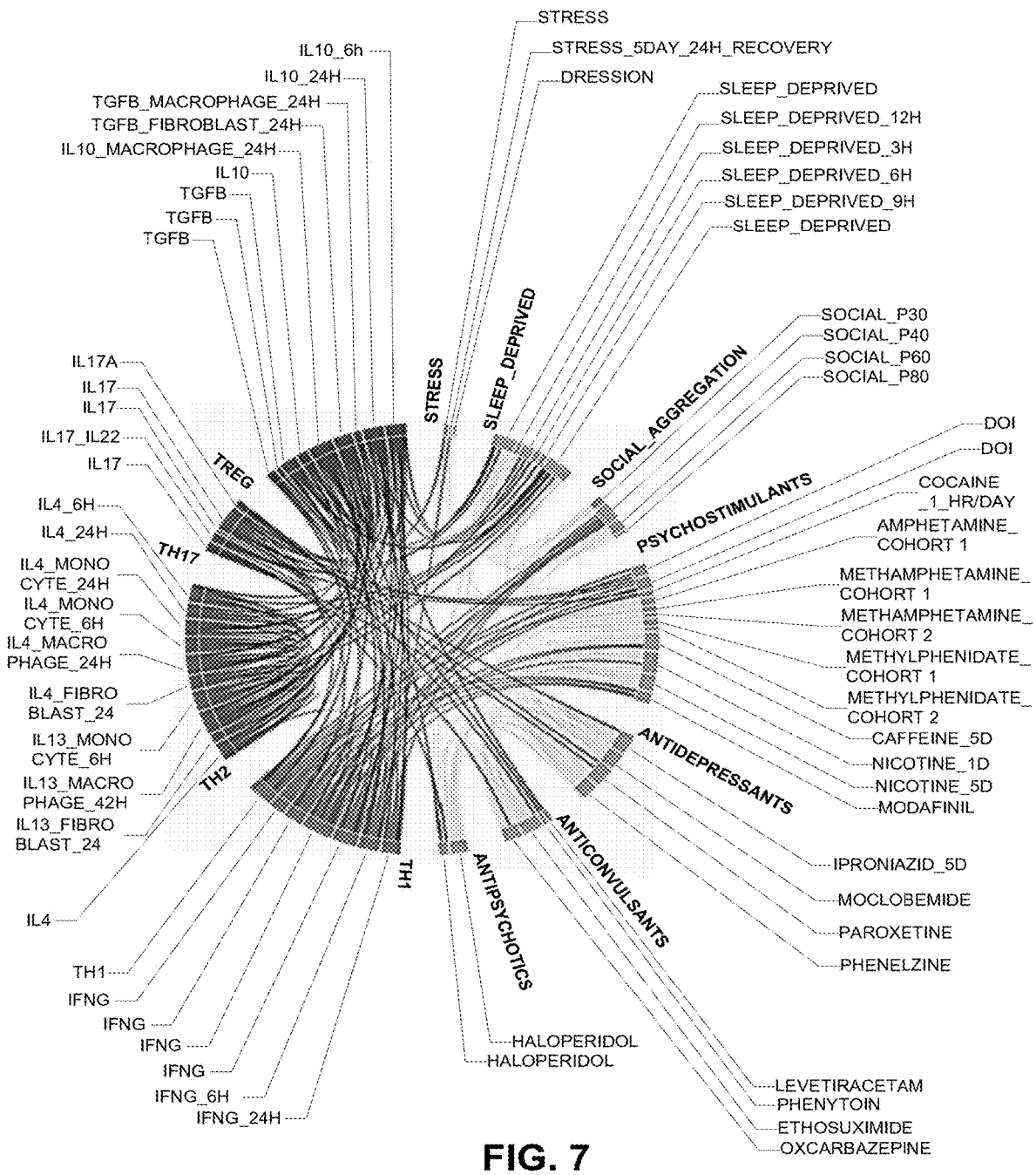
FIG. 7 shows acircos plot showing the connectivity of Th1 response and social aggregation. Here labels are shown for the datasets analyzed and presented in FIG. 1H.

We previously demonstrated T cells influence learning behavior and exert their beneficial effects presumably from the meninges[1, 4]. To address the role of meningeal T cells in social behavior, the extravasation of T cells into the meninges of wild-type mice was decreased using antibodies against VLA4[15] an integrin expressed on T cells (among other immune cells) required for CNS homing. Partial elimination of T cells from meninges (FIGS. 6A-6C) was sufficient to cause a loss in social preference (FIG. 1G). Despite their proximity to the brain, meningeal T cells do not enter the brain parenchyma, suggesting their effect is mediated by soluble factors. To identify which T cell-mediated pathways are involved in regulating social behavior, a gene set enrichment analysis (GSEA) was used to search for T cell-mediated response signatures (IFN-γ, IL-4/IL-13, IL-17, 11-10, TGF-β) in 41 transcriptomes from mouse and rat brain cortices. GSEA assesses if the expression of a previously defined group of related genes is enriched in one biological state. In this case, GSEA was used to identify which cytokine induced response signatures were enriched in the transcriptomes of mice and rats exposed to different stimuli. The stimuli included: social aggregation, sleep deprivation, stress, psycho stimulants, antidepressants, anticonvulsants, and antipsychotics. Transcriptomes from cortices of animals exposed to social aggregation and psychostimulants were enriched for IFN-γ regulated genes (FIG. 1H, FIG. 7, and Supplementary Tables 2, 3).

Figure 2A:
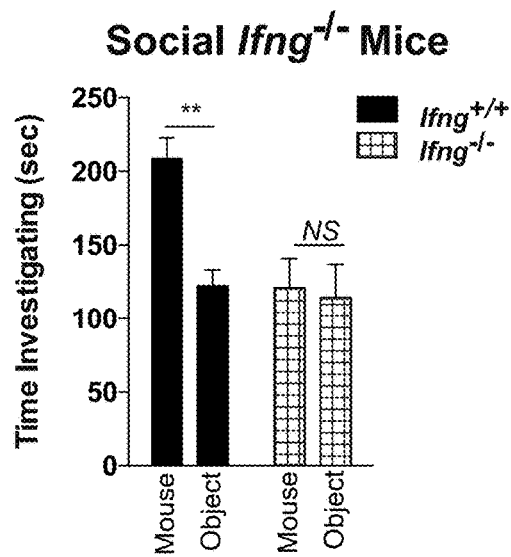
FIGS. 2A-2M show that IFN-γ supports proper neural connectivity and social behavior.
Figure 2B:
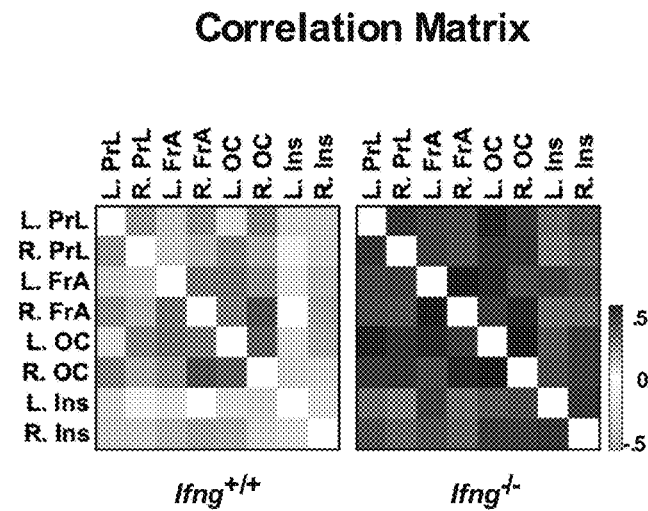
Figure 2C:
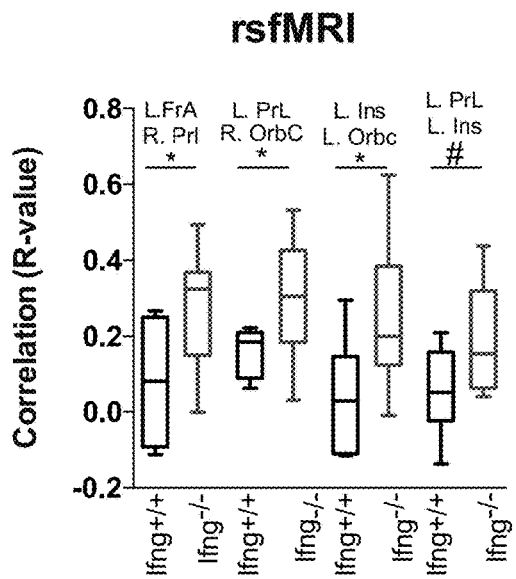
Figure 2D:
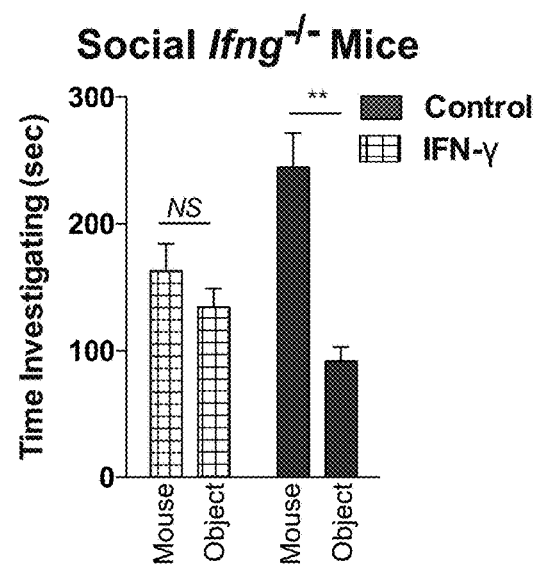
Figure 8A:
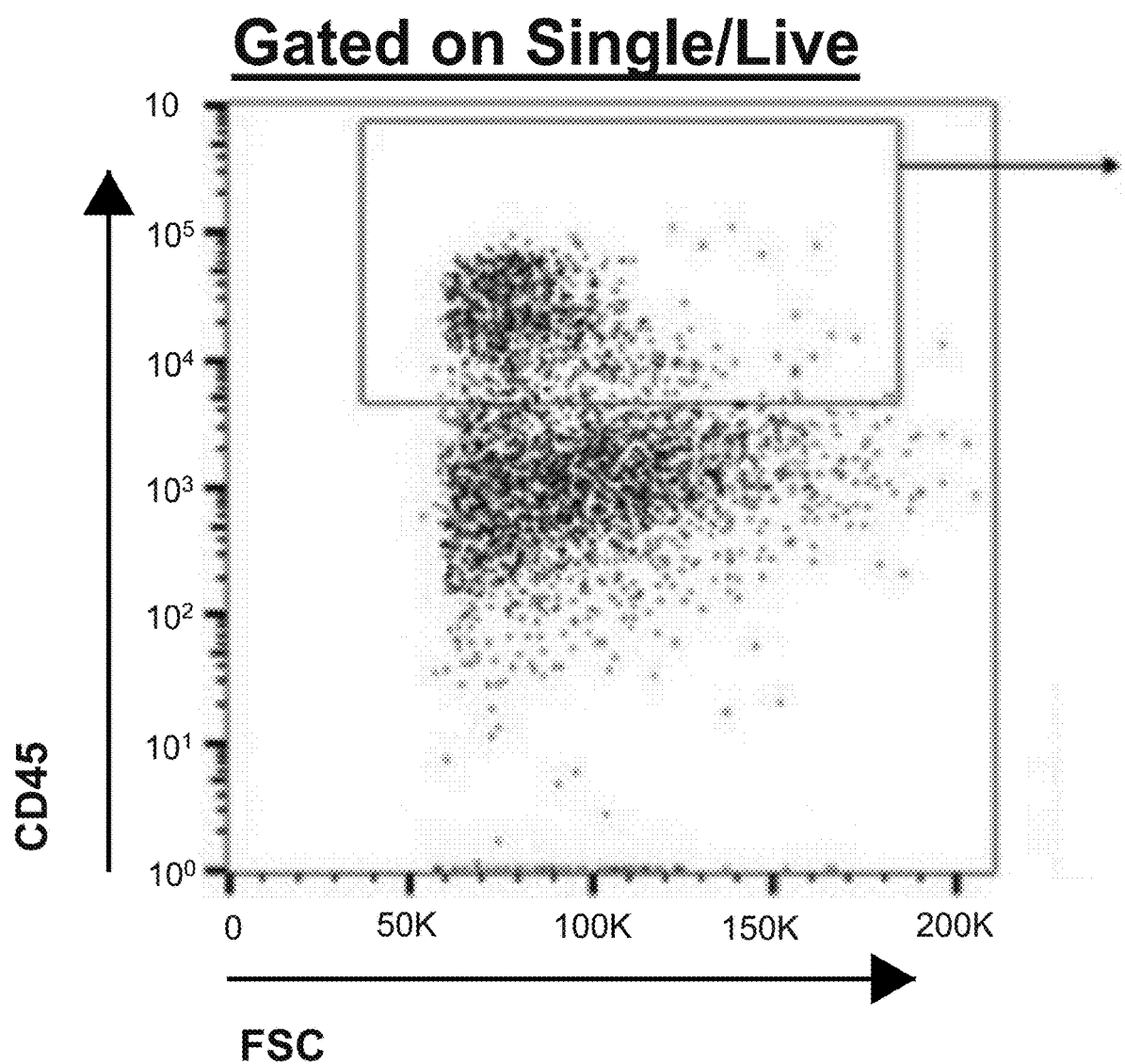
FIGS. 8A-8I show that T cells in the meninges produce IFN-γ and IFN-γ deficient mice have normal levels of anxiety and motor behavior.
Figure 8B:
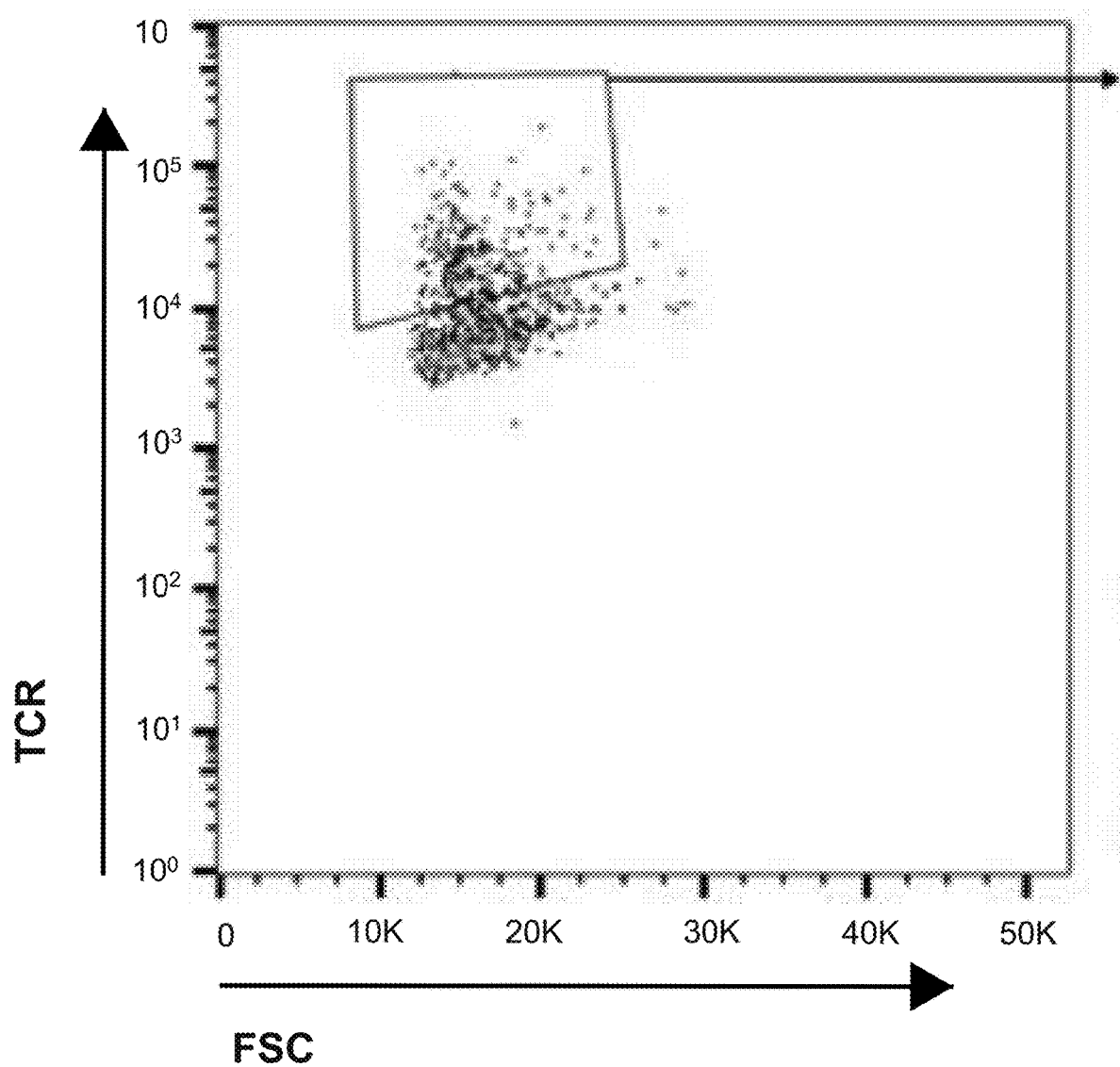
Figure 8C:
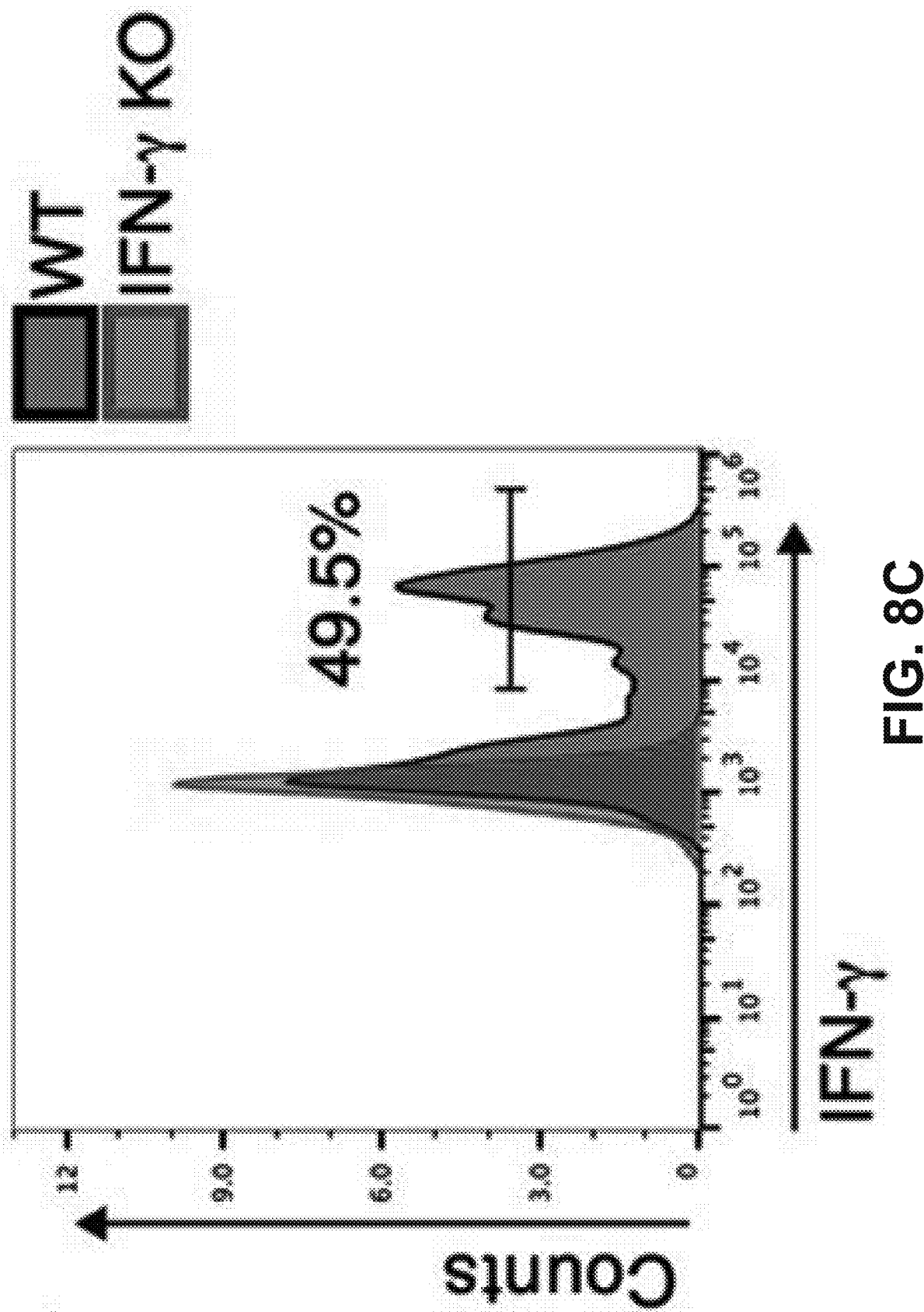
Figure 8F:
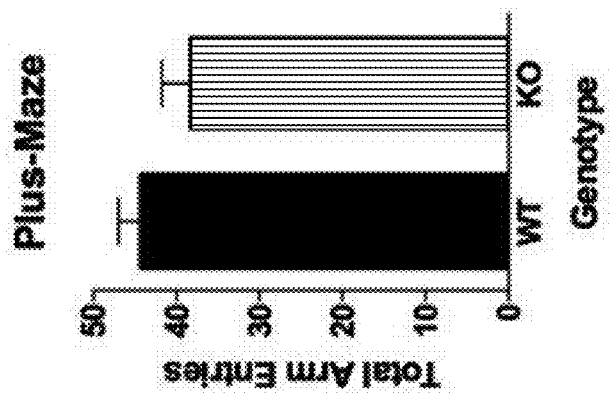
Figure 8E:
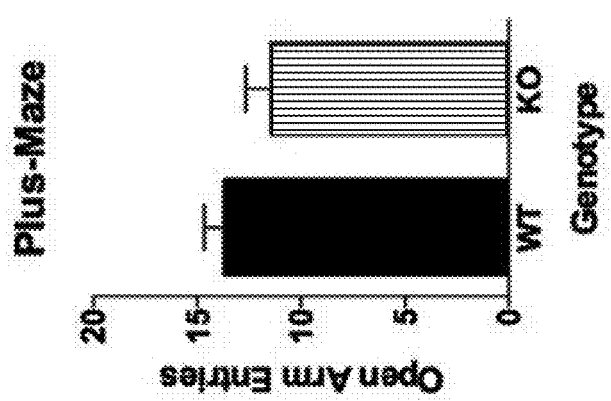
Figure 8D:
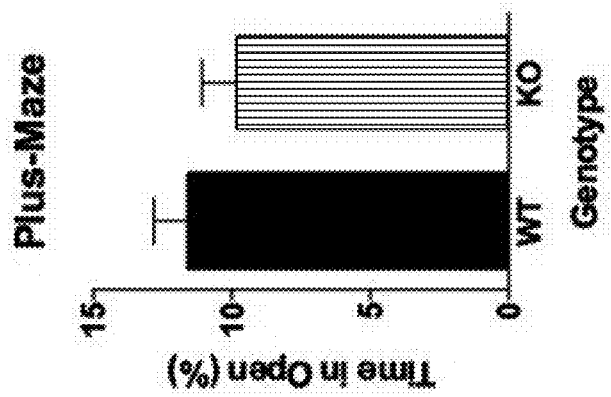
Figure 8I:
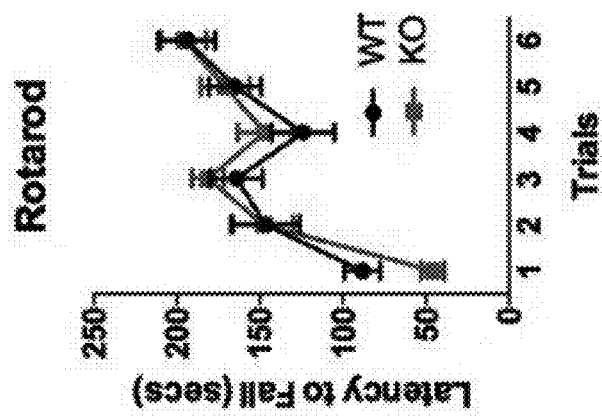
Figure 8H:
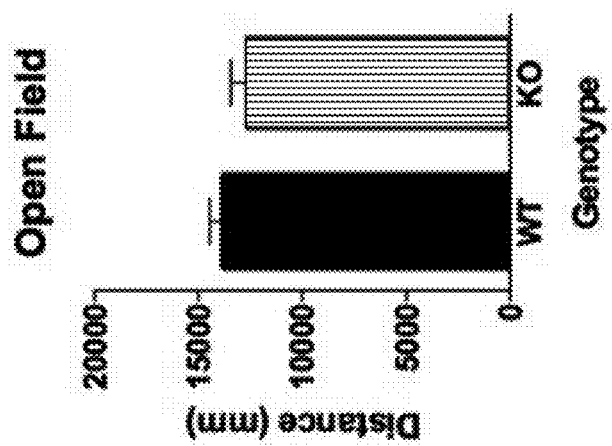
Figure 8G:
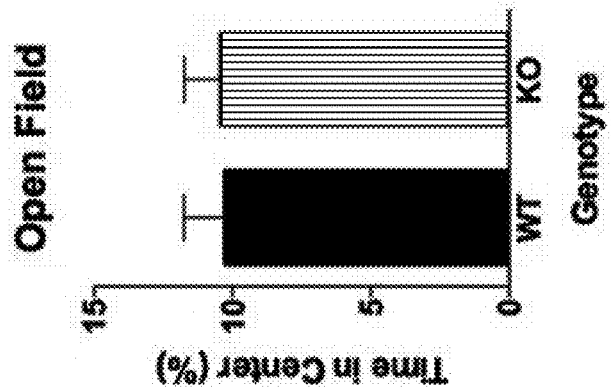
Figure 9A:
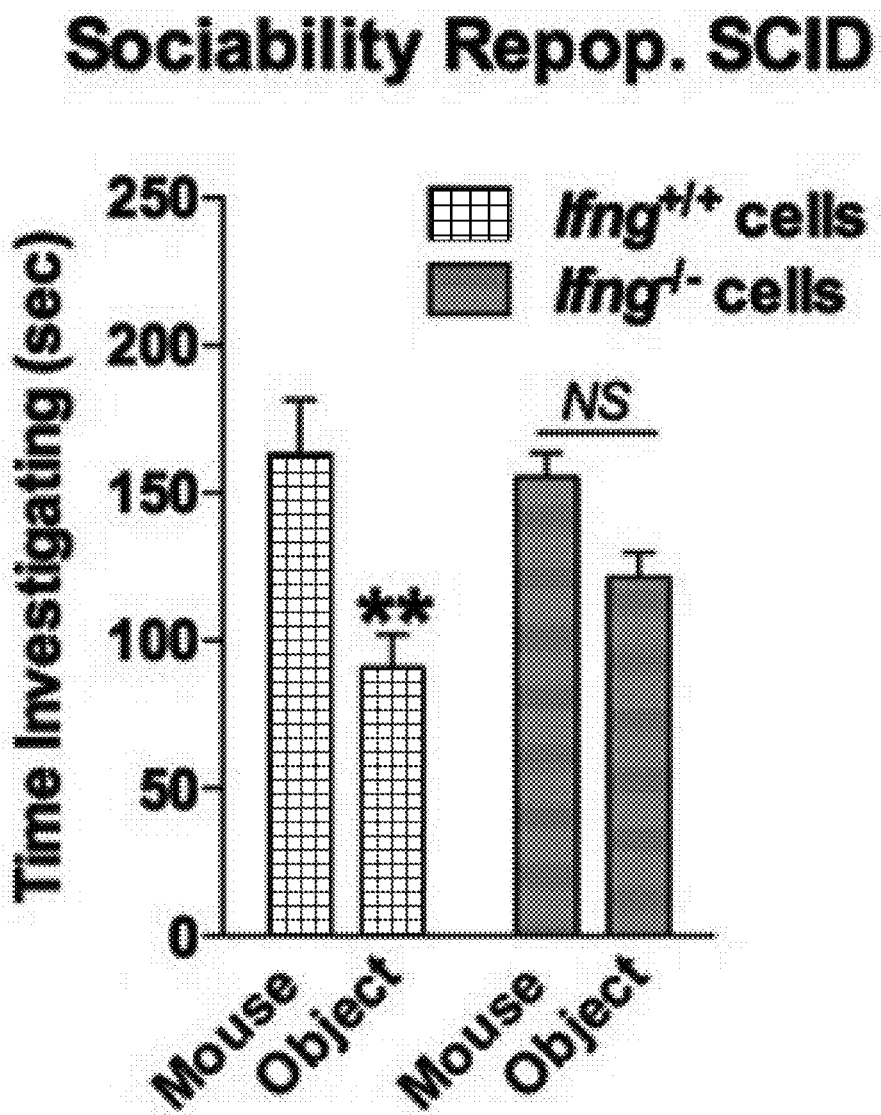
FIGS. 9A-9G show that IFN-γ signaling is necessary for normal social behavior.
Figures 9B, 9C, 9D:
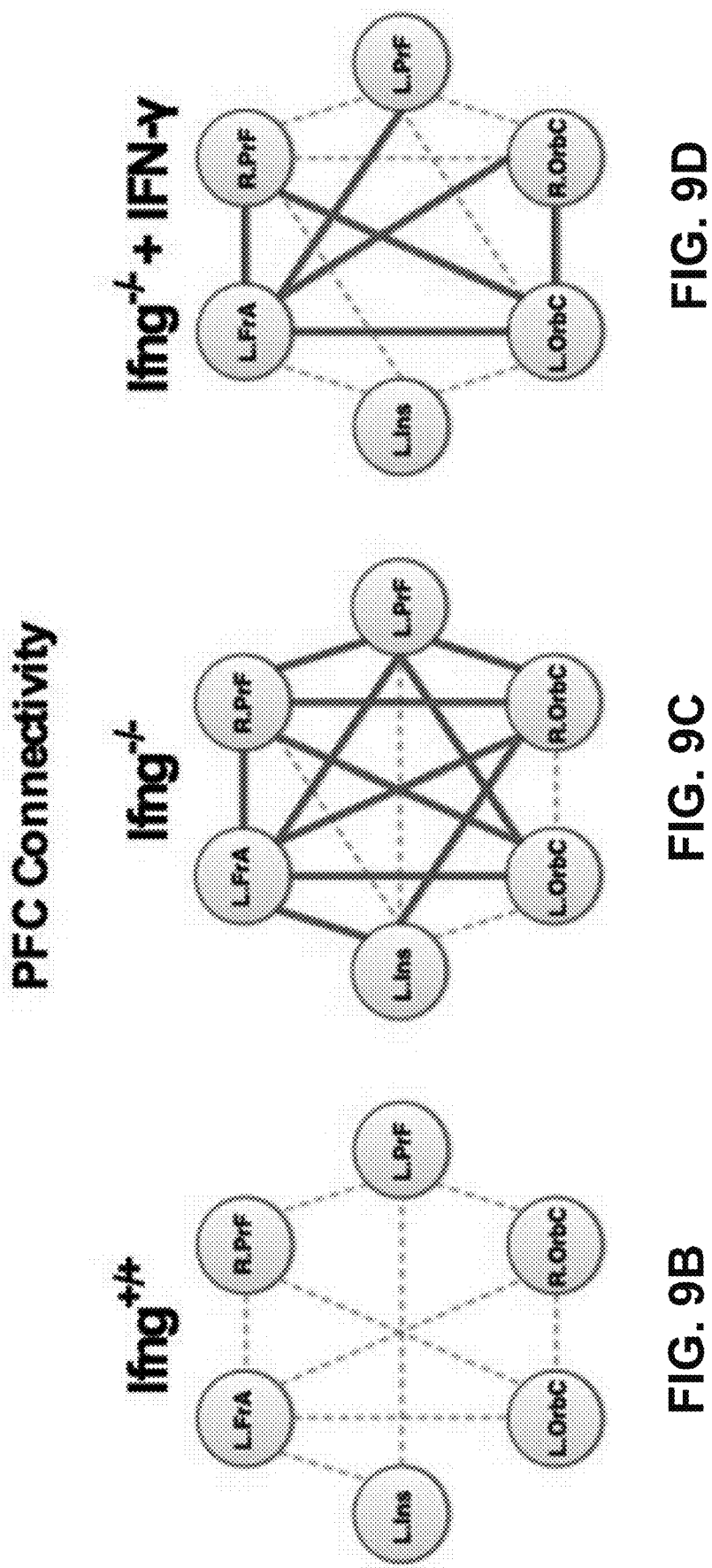
Figure 9G:
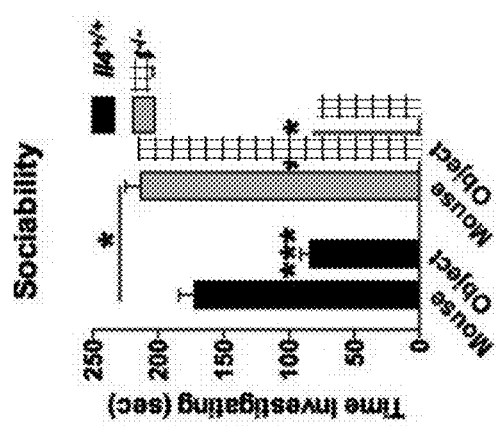
Figure 9F:
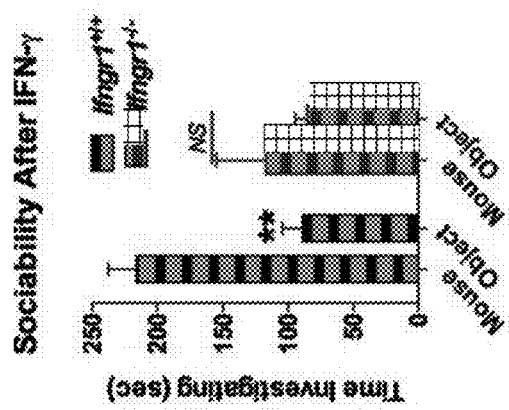
Figure 9E:
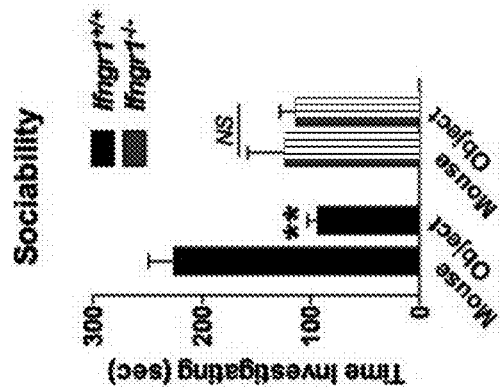
Figure 10A:
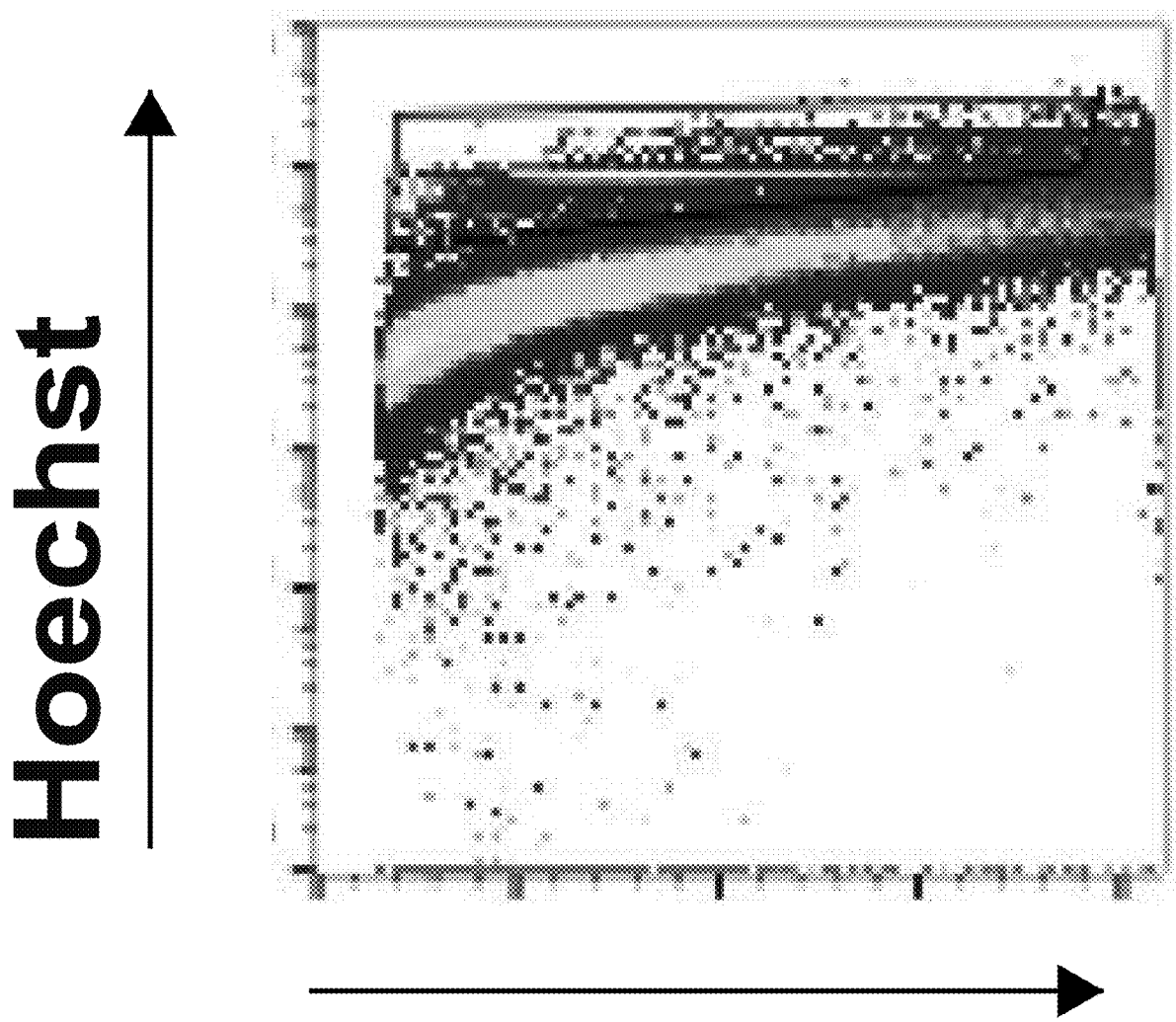
FIGS. 10A-10E show gating strategy for neurons and microglia. Brain homogenates were stained and analyzed by flow cytometry. Cells were gated on nucleated, singlets, and live. Neurons were then gated on NeuN positive and microglia on CD11B positive cells.
Figure 10B:
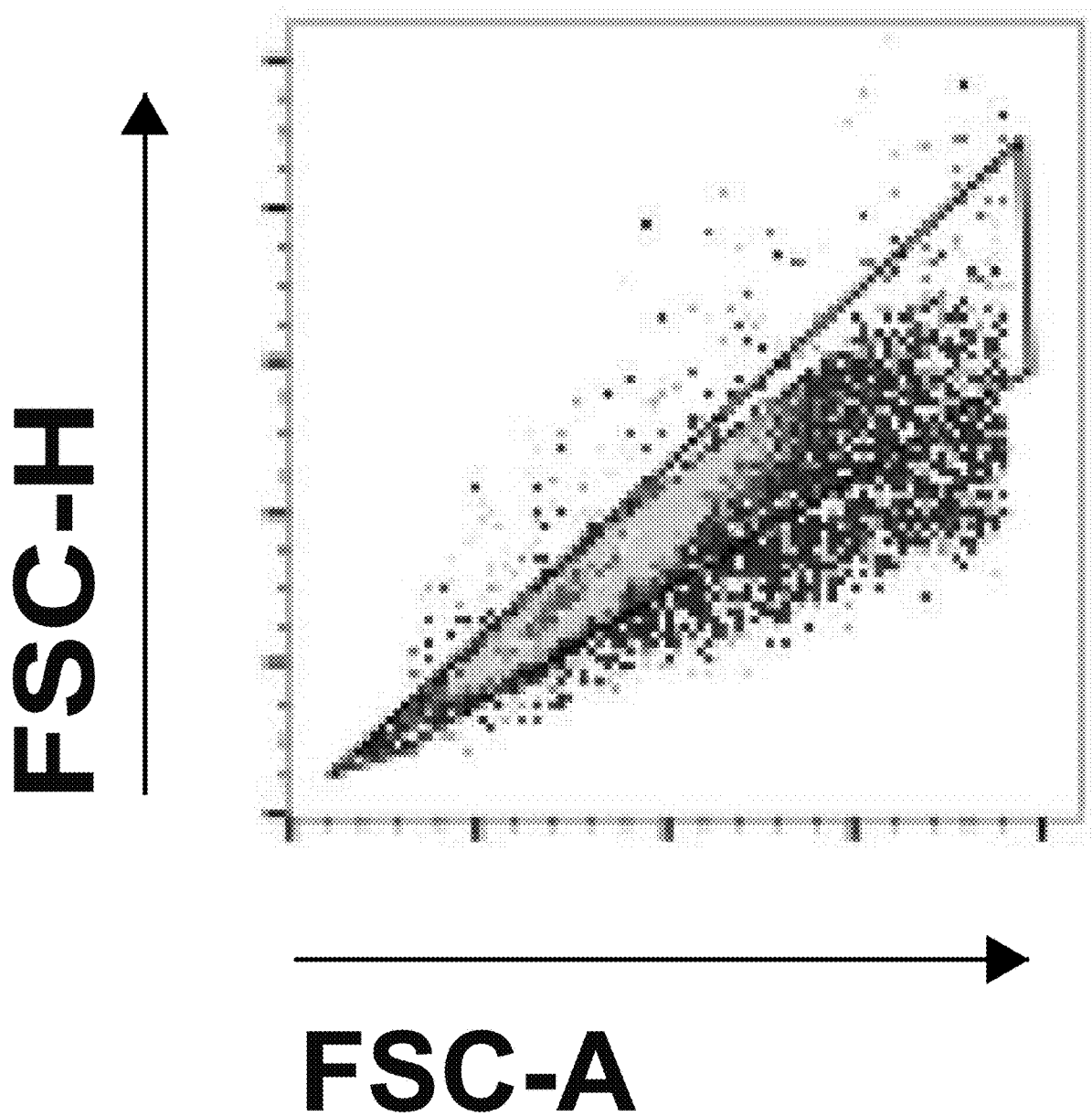
Figure 10C:
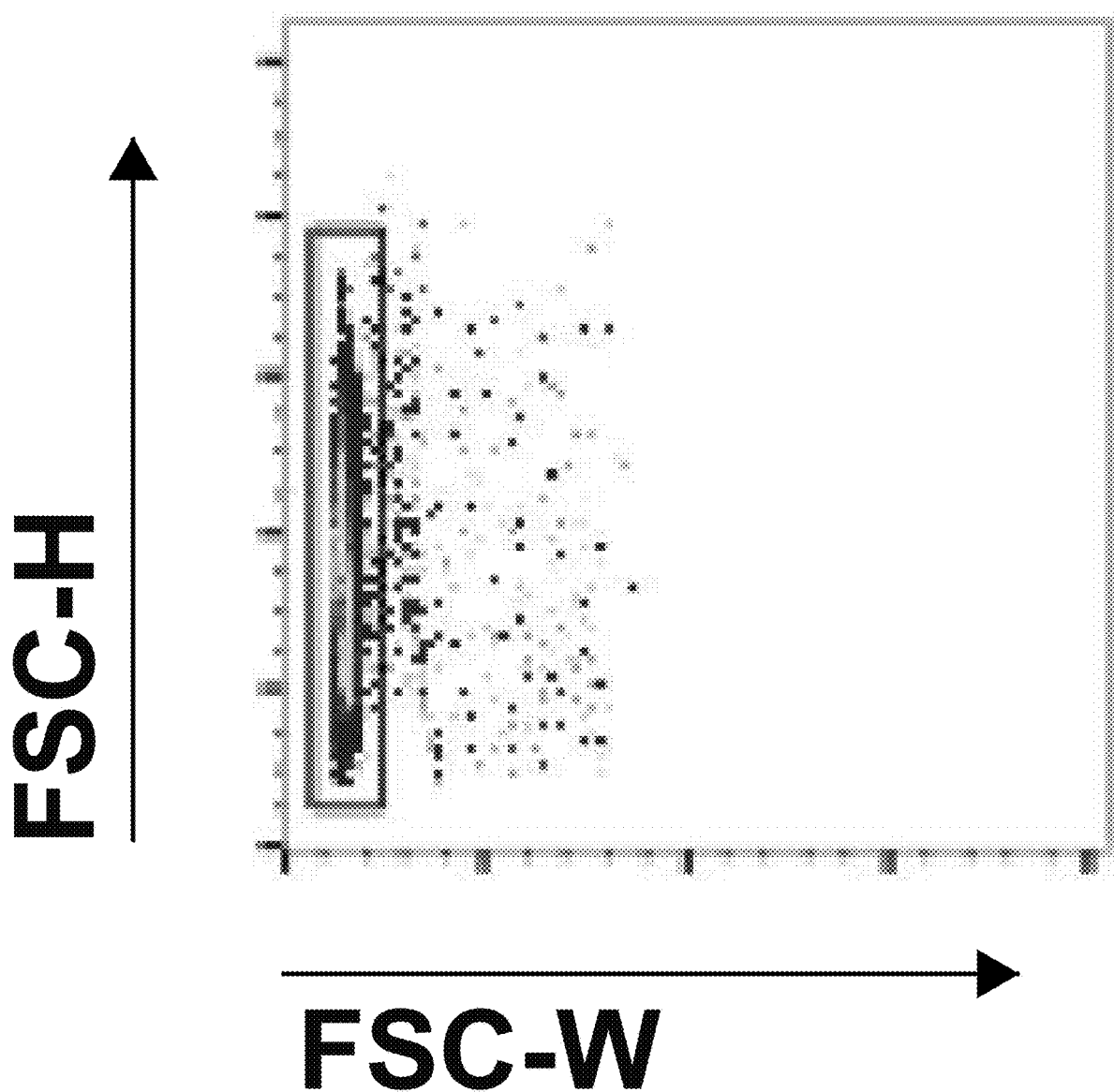
Figure 10D:
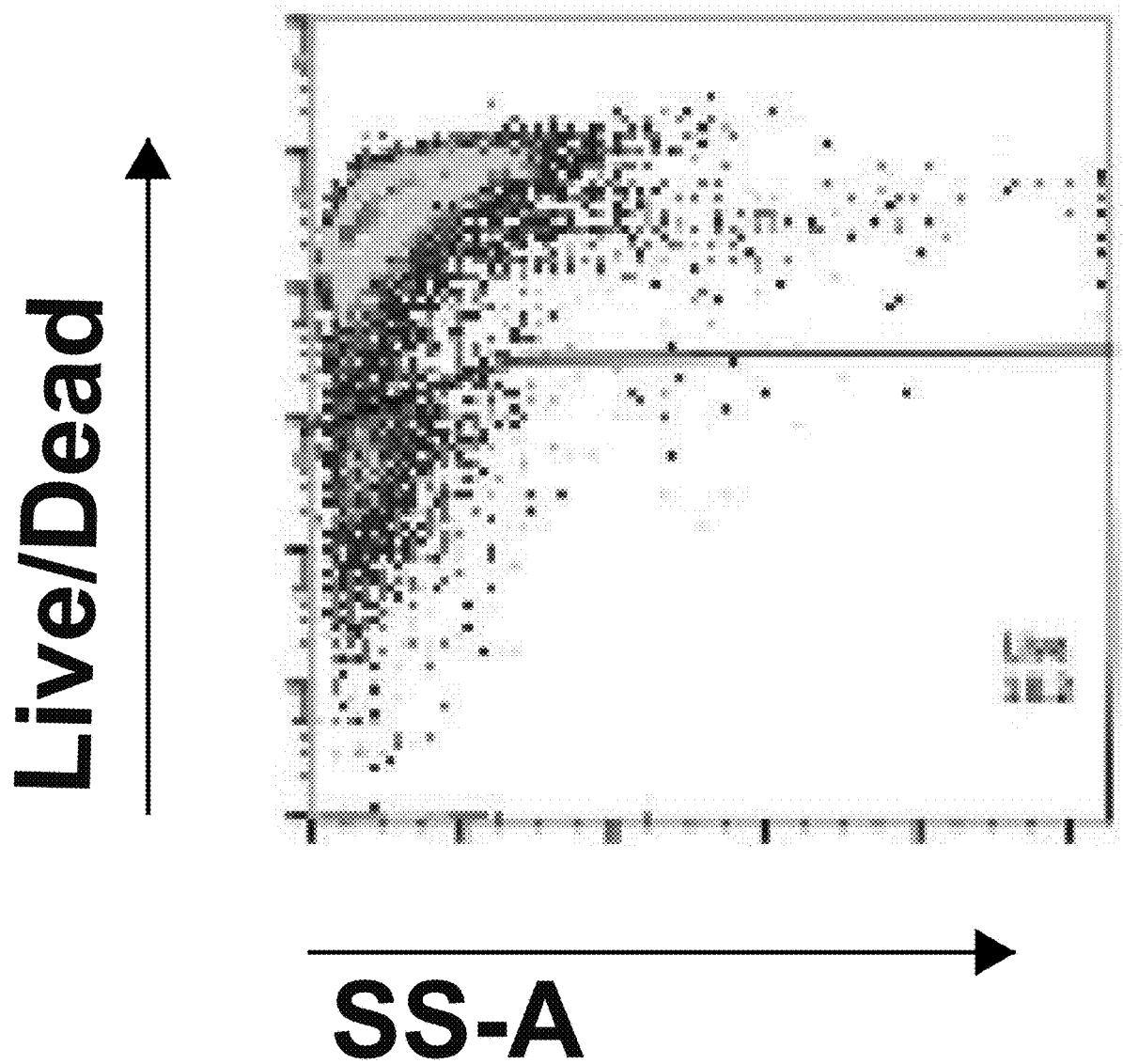
Figure 10E:
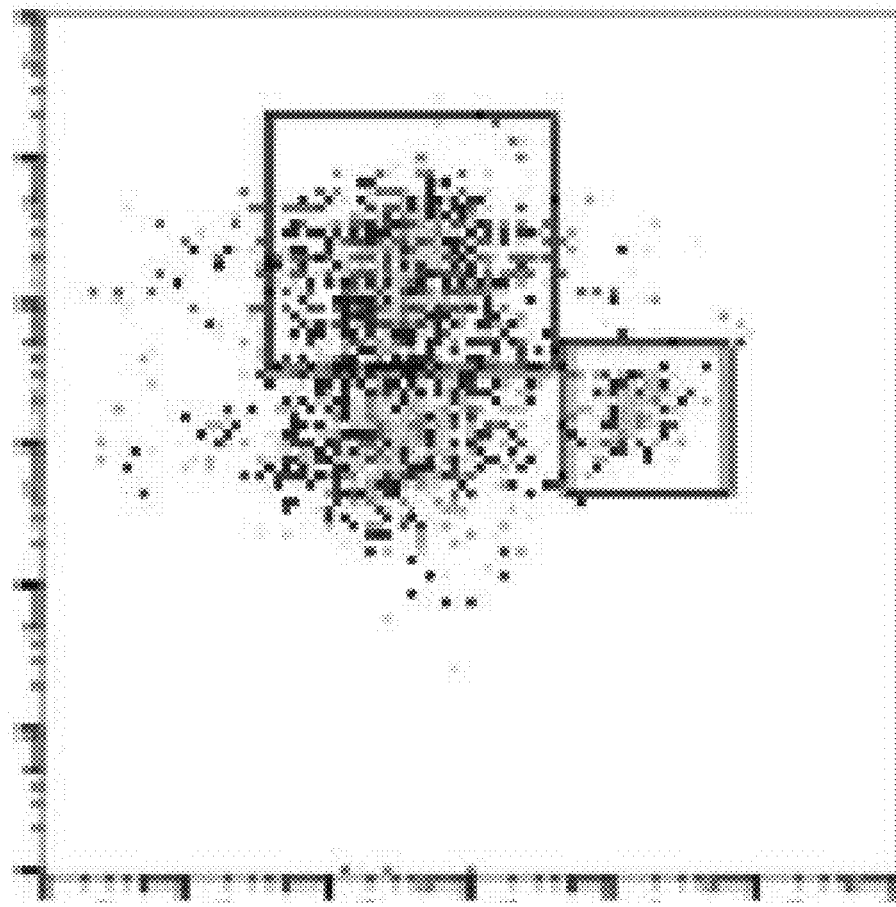

A substantial number of meningeal T cells are capable of expressing IFN-γ (41.95%±6.34 of TCR+ cells; FIGS. 8A-8C) and recent work has proposed a role for IFN-γ in T cell trafficking into meningeal spaces[16]. To assess the potential role of IFN-γ in mediating the influence of T cells on social behavior, the social behavior of IFN-γ deficient mice was examined and it was determined that they had social deficits (FIG. 2A). Importantly, IFN-γ deficient mice did not show anxiety or motor deficits (FIGS. 8D-8I). Similar to SCID mice, IFN-γ deficient mice also exhibited aberrant hyperconnectivity in fronto-cortical/insular regions (FIGS. 2B-2C; Supplement Table 1). While repopulating SCID mice with lymphocytes from wild-type mice restored a social preference, repopulating SCID mice with lymphocytes from Ifng−/−mice did not have such an effect (FIG. 9A). Remarkably, a single injection of recombinant IFN-γ into the cerebrospinal fluid (CSF) of Ifng−/−mice was sufficient to restore their social preference when tested after 24 hours post injection (FIG. 2D) and reduce overall hyperconnectivity in the PFC (FIGS. 9B-9D). To further validate a role for IFN-γ signaling in social behavior, mice deficient for the IFN-γ receptor (Ifngr–/–mice) were tested and it was found that they had a similar social deficit as Ifng–/–mice (FIG. 9E), which, as expected, was not rescued by injecting recombinant IFN-γ into the CSF (FIG. 9F). Based on previous demonstration of a role for IL-4 produced by meningeal T cells in spatial learning behavioral, it was assessed whether deficiency in IL-4 would also result in social deficits. IL-4 deficient mice did not demonstrate social deficits; in fact, they spent more time investigating a novel mouse than a novel object as compared to wild-type mice (FIG. 9G).

Figure 2E:
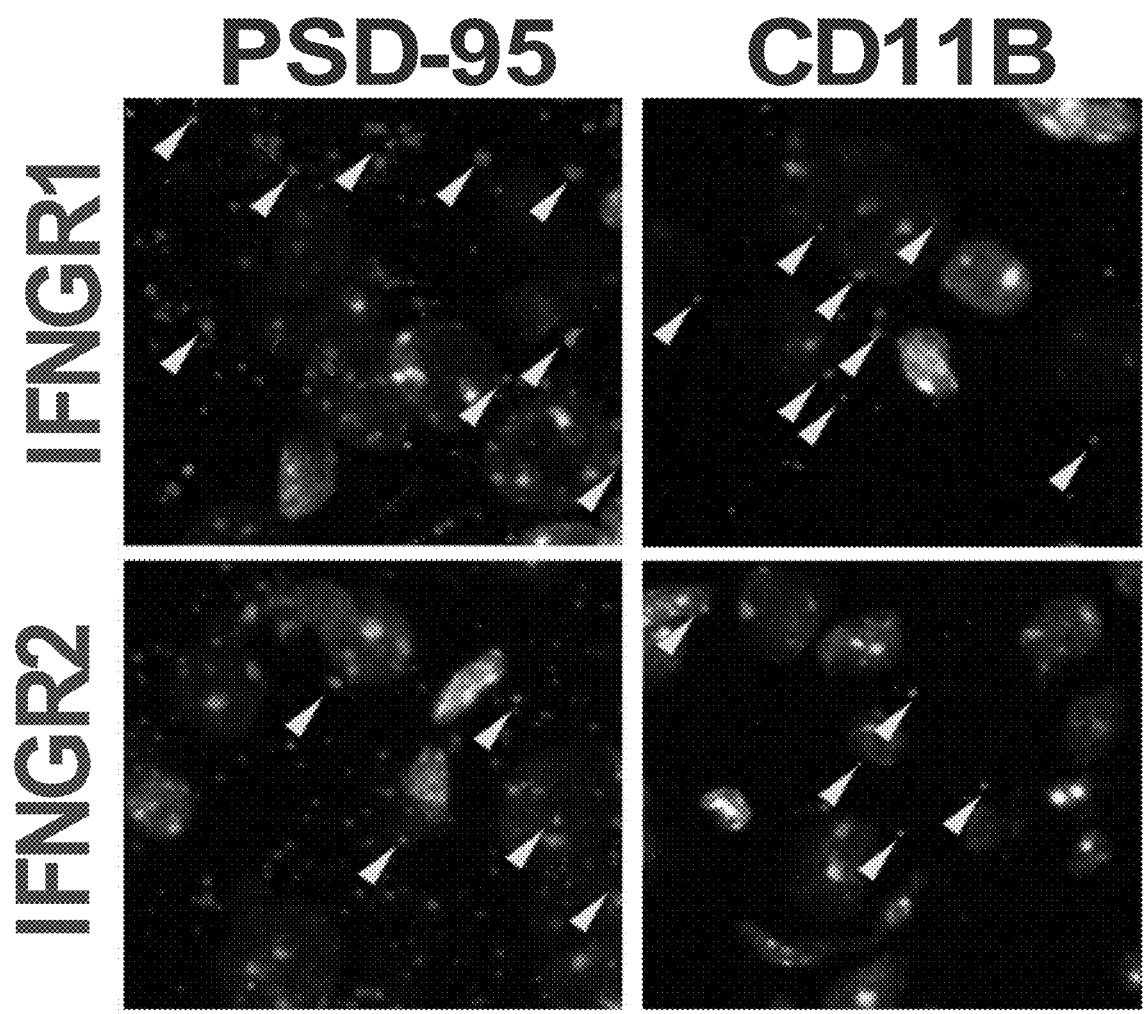
Figure 2F:
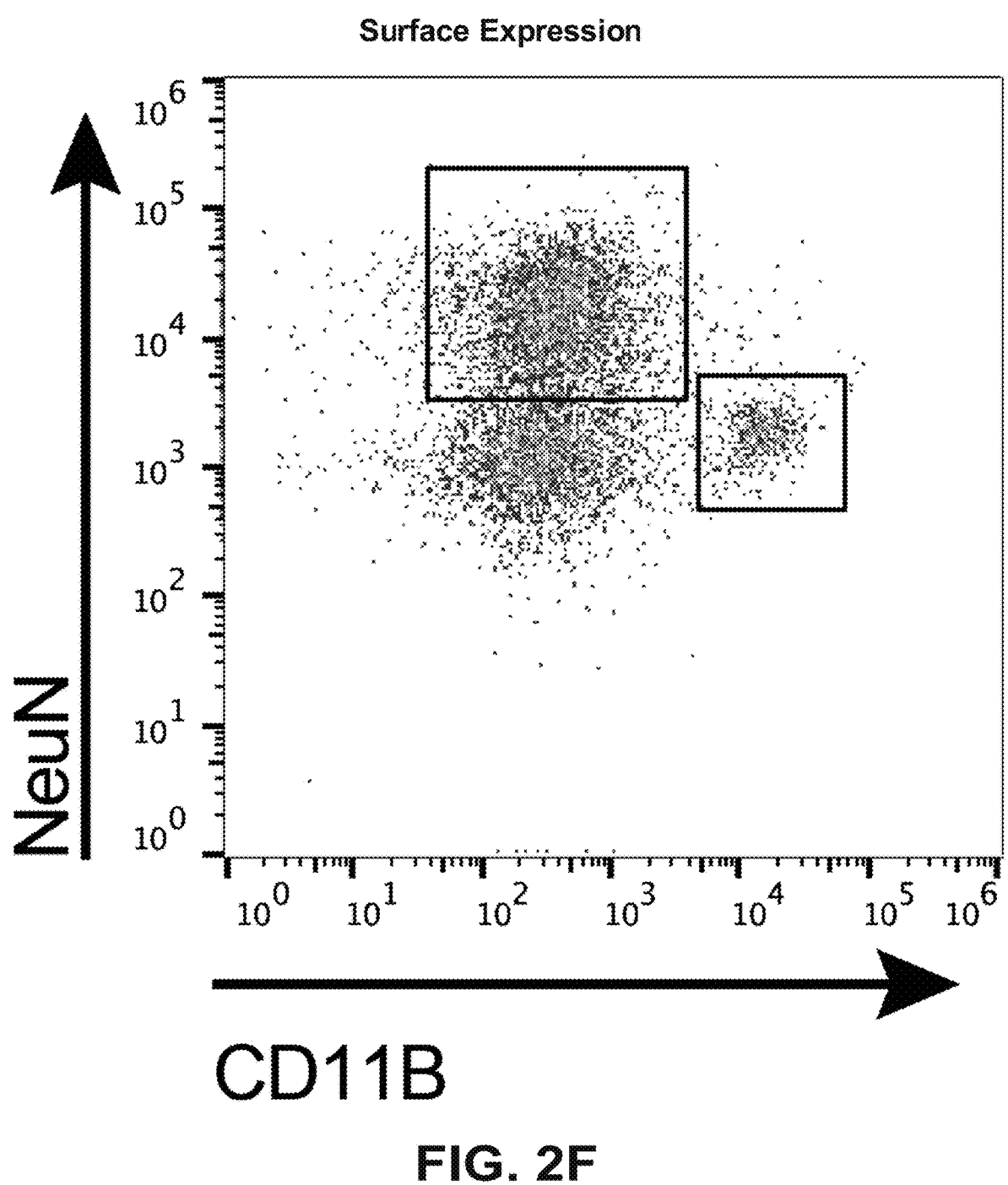
Figure 11:
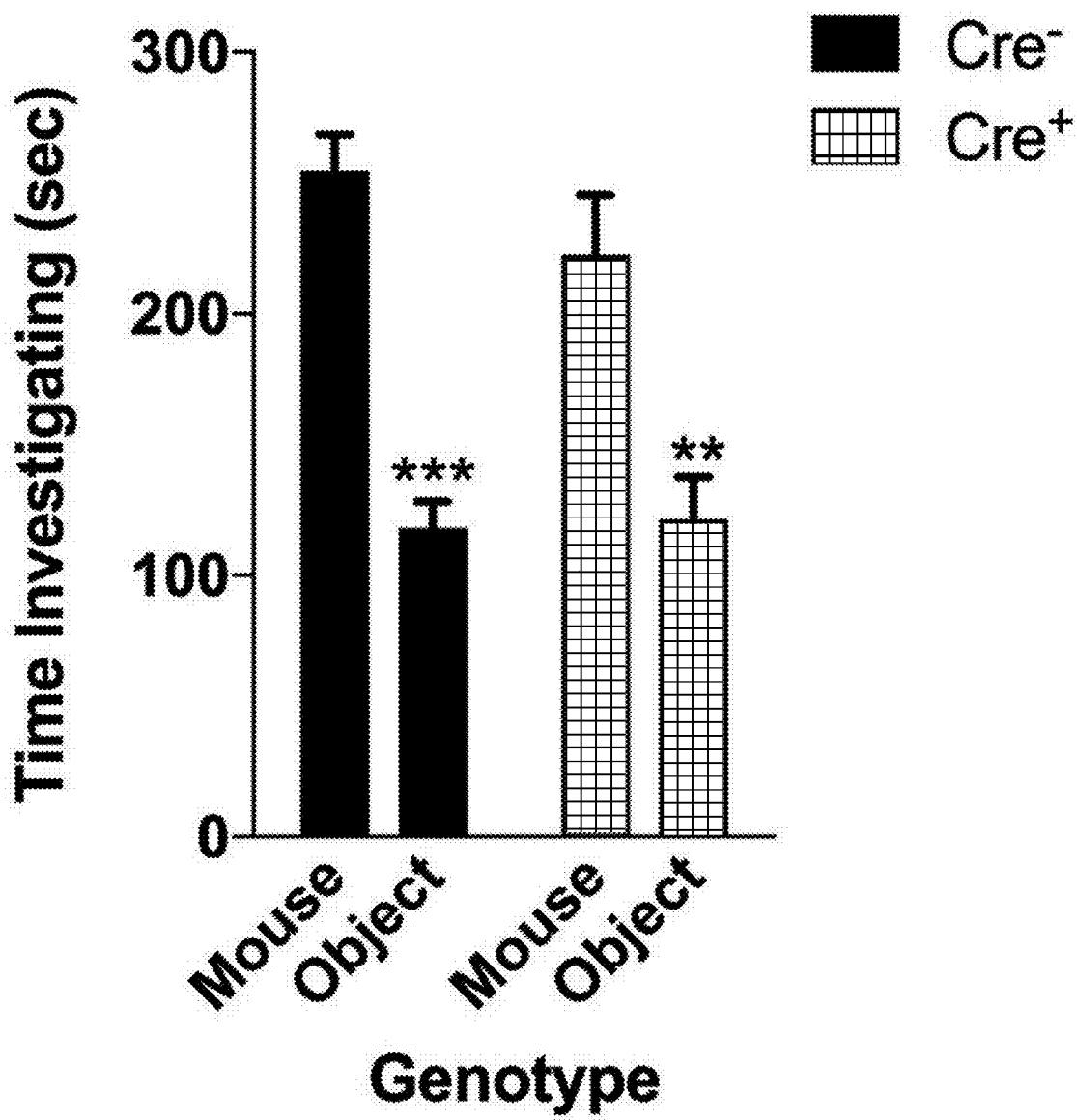
FIG. 11 shows that IFN-γ Signaling in Microglia is not Necessary for Normal Social Function. Mice deficient for STAT1 in microglia have normal social preference (n=9 mice per group; ANOVA for Cre $F (1, 16)=1.809$ and sociability $F (1, 16)=30.10$; $P<0.0001$; $P<0.01$; * $P<0.001$ Sidak's post-hoc).

To determine which cell types in the brain respond to IFN-γ, mouse PFC was analyzed for the expression of IFN-γ receptor subunits 1 and 2 and it was found that both neurons and microglia express mRNA and protein for R1 and R2 subunits of the IFN-γ receptor (FIGS. 2E, 2F; FIGS. 10A-10E). Microglia are CNS resident macrophages and are known to express the IFN-γ receptor 17. However, genetically deleting STAT1, the signaling molecule downstream of the IFN-γ receptor, from microglia (and other cells of myeloid origin), did not disturb normal social preference (FIG. 11). These results led us to focus on neuronal responses to IFN-γ as they relate to social behavior.

Figure 2H:
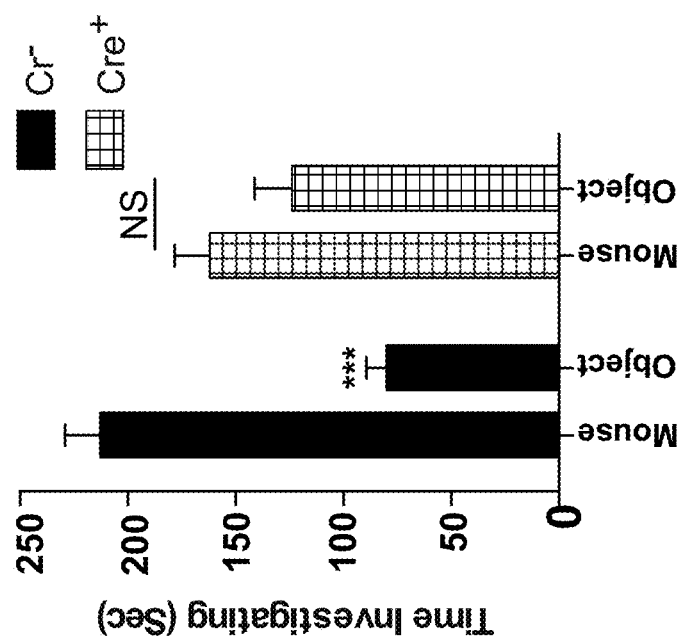
Figure 2G:
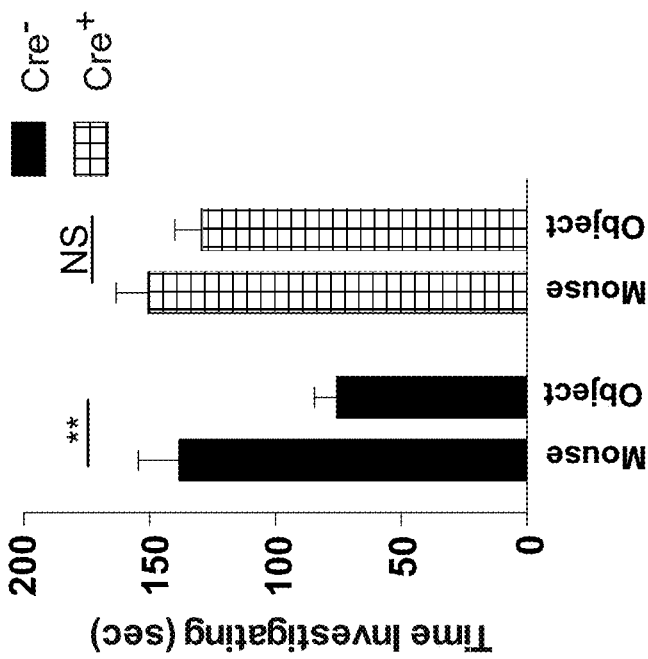
Figure 12B:
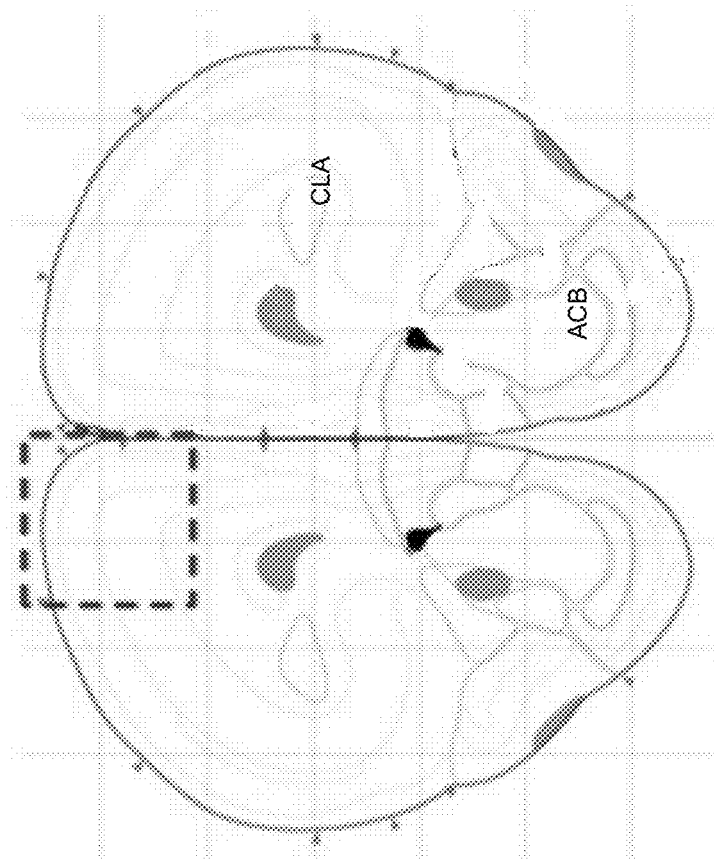
FIGS. 12A-12C show deleting IFNGR1 by AAV transduction. Mice were injected with AVVs expressing Cre and GFP under a synapsin promoter.
Figure 12A:
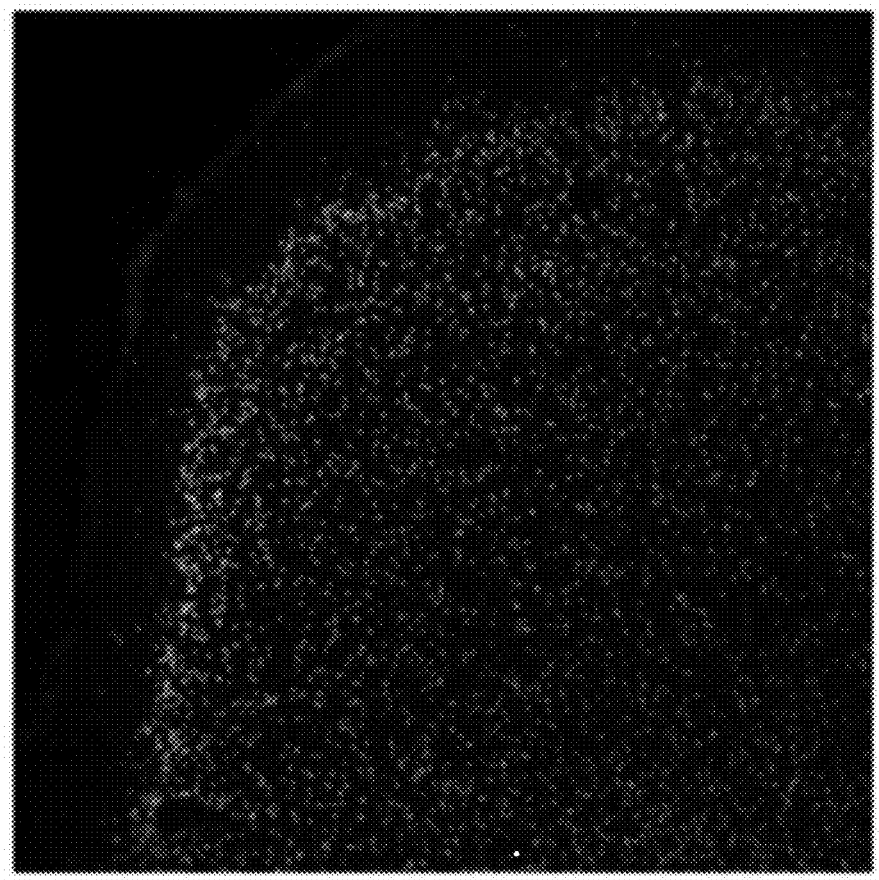
Figure 12C:
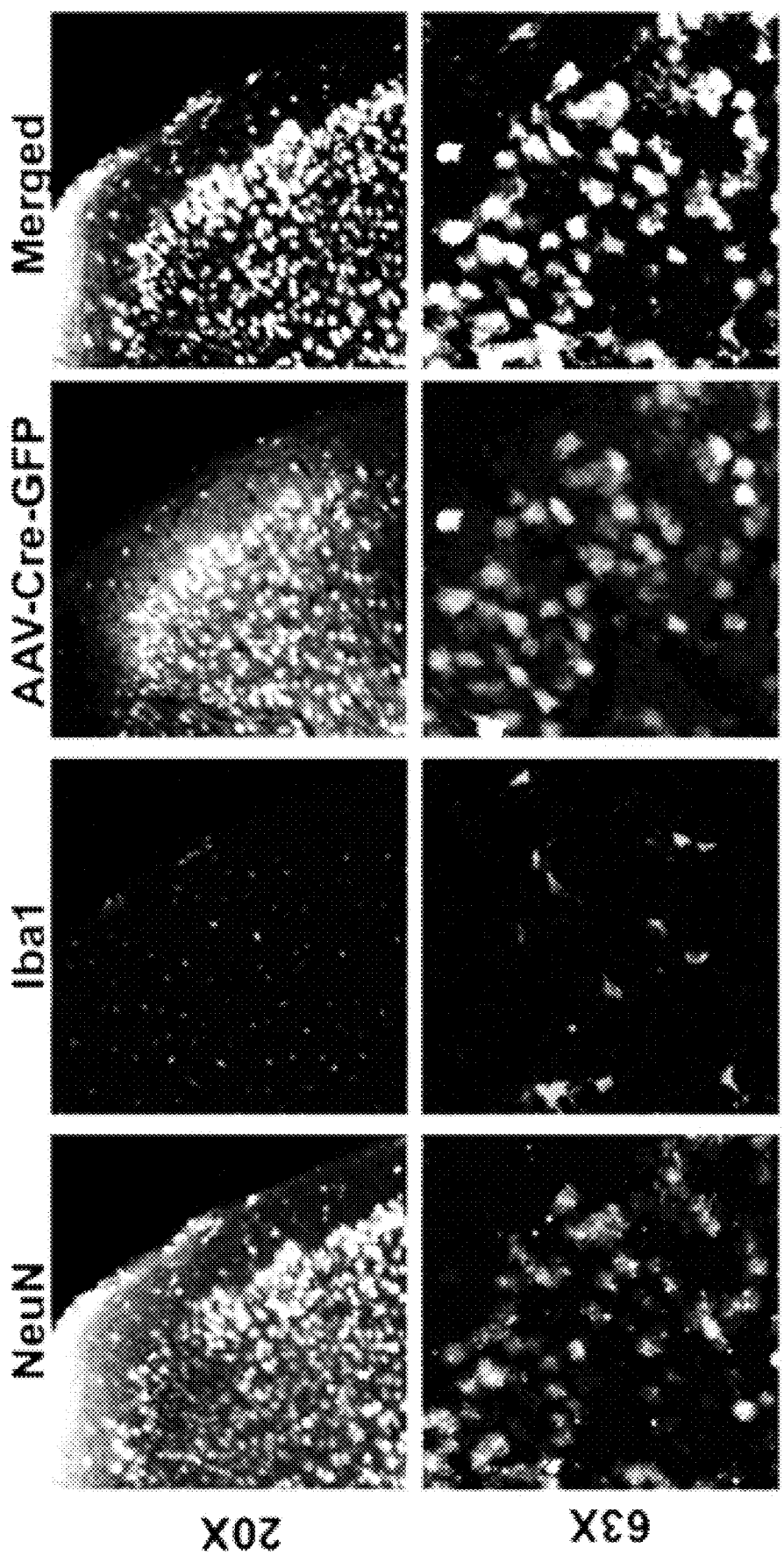

To assess a role for IFN-γ in neuronal signaling, Ifngrl in PFC neurons were deleted via AAV delivery of Cre recombinase under the Synapsin I promoter (FIGS. 12A-12C). Attenuating IFN-γ signaling in PFC neurons was sufficient to alter mouse behavior in a 3-chamber social task and result in a lack of social preference (FIG. 2G), reinforcing the importance of IFN-γ signaling on neurons for social behavior. Injecting recombinant IFN-γ into the CSF, activated layer I neocortical neurons as assessed by c-fos immunoreactivity (FIGS. 13A-13D). These neurons are almost entirely inhibitory[18], suggesting that IFN-γ may drive regional inhibition of circuits by directly activating layer I inhibitory neurons located in close proximity to the brain surface and CSF. To investigate mechanisms downstream of the IFN-γ receptor, VgatCre::Stat1 fl/fl mice were used. Deletion of STAT1 from GABAergic inhibitory neurons was sufficient to induce deficits in social behavior (FIG. 2H), suggesting that the IFN-γ may be signaling through inhibitory neurons.

Figure 2I:
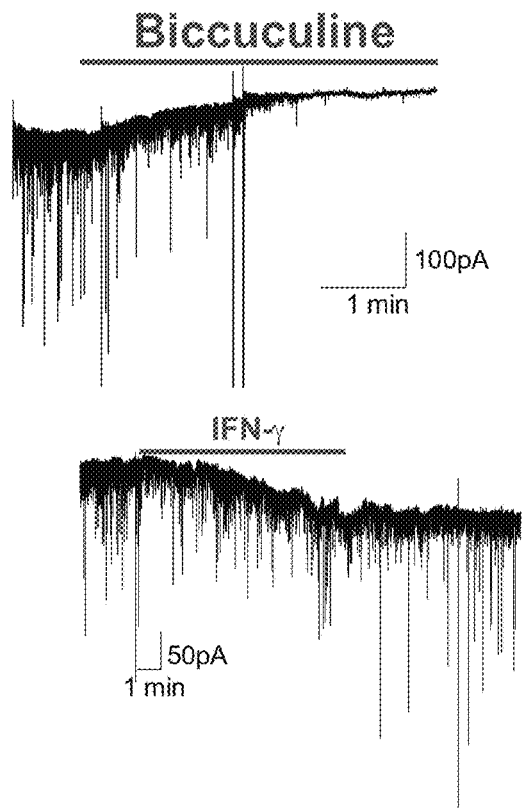
Figure 2J:
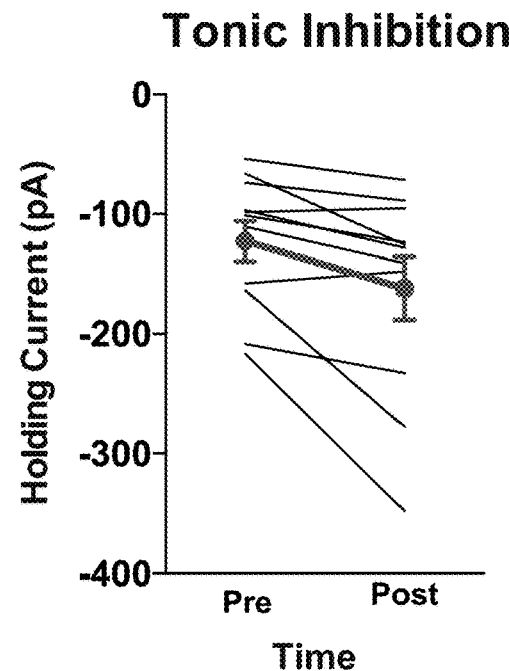
Figure 2K:
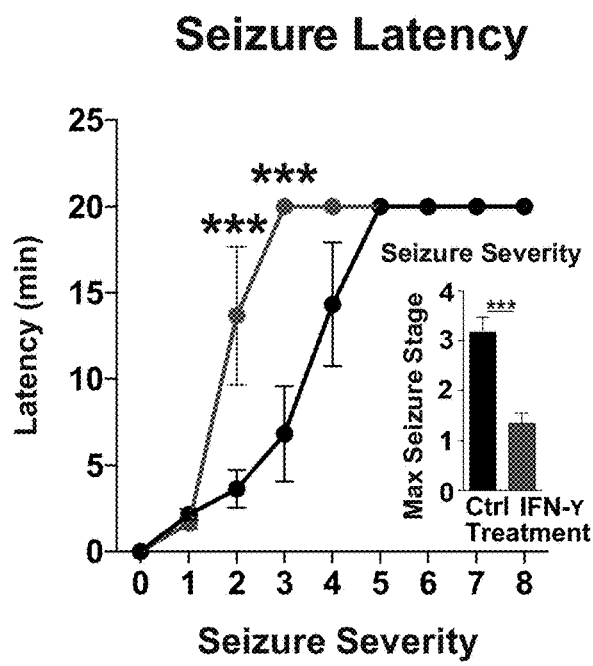
Figure 2L:
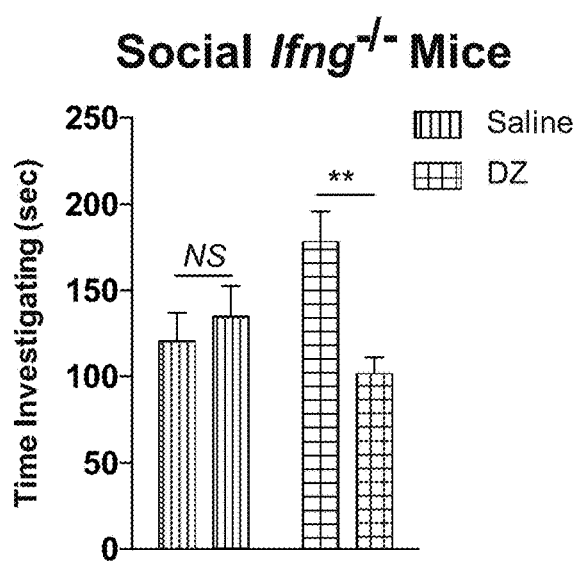
Figure 2M:
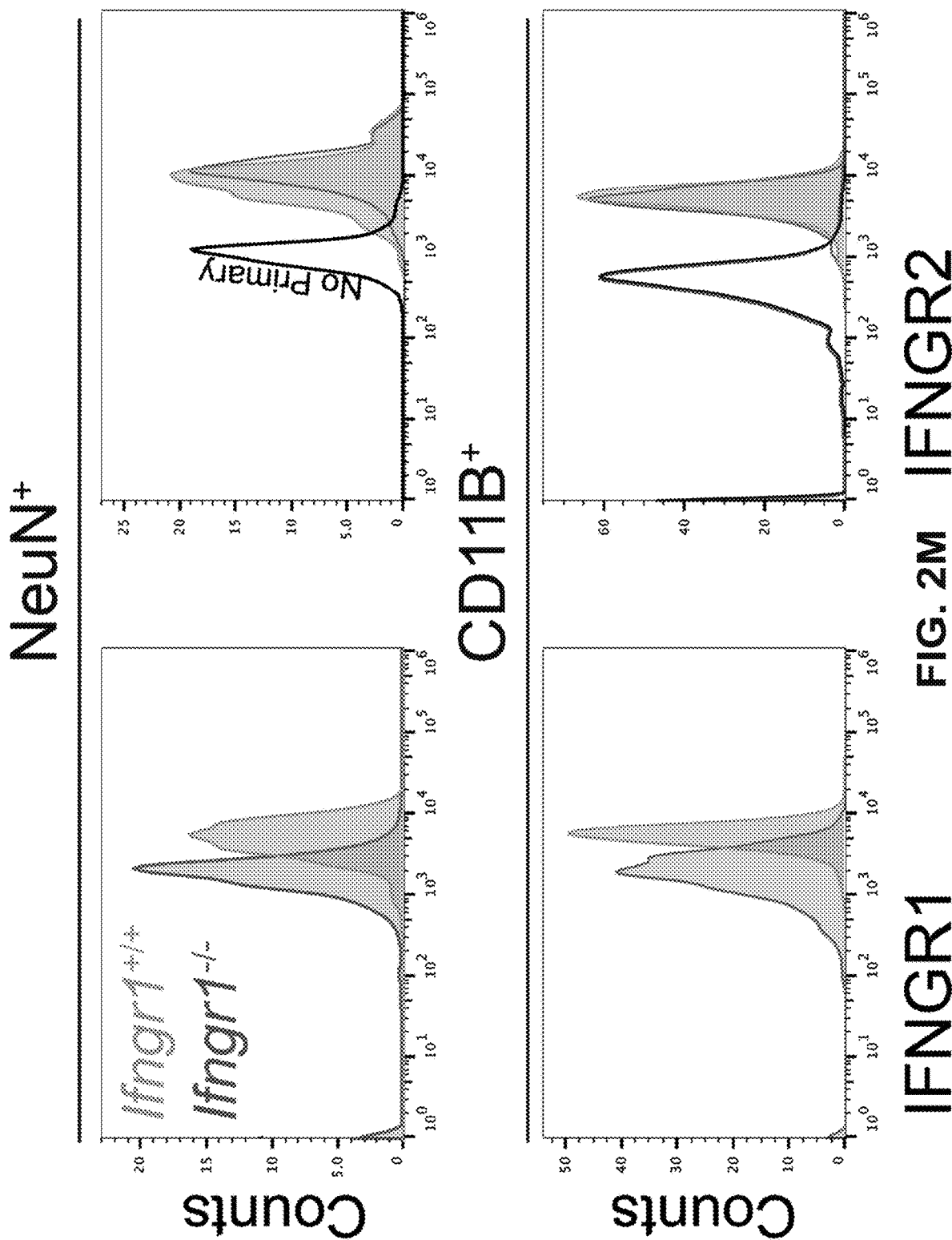
Figures 13A, 13B, 13C:
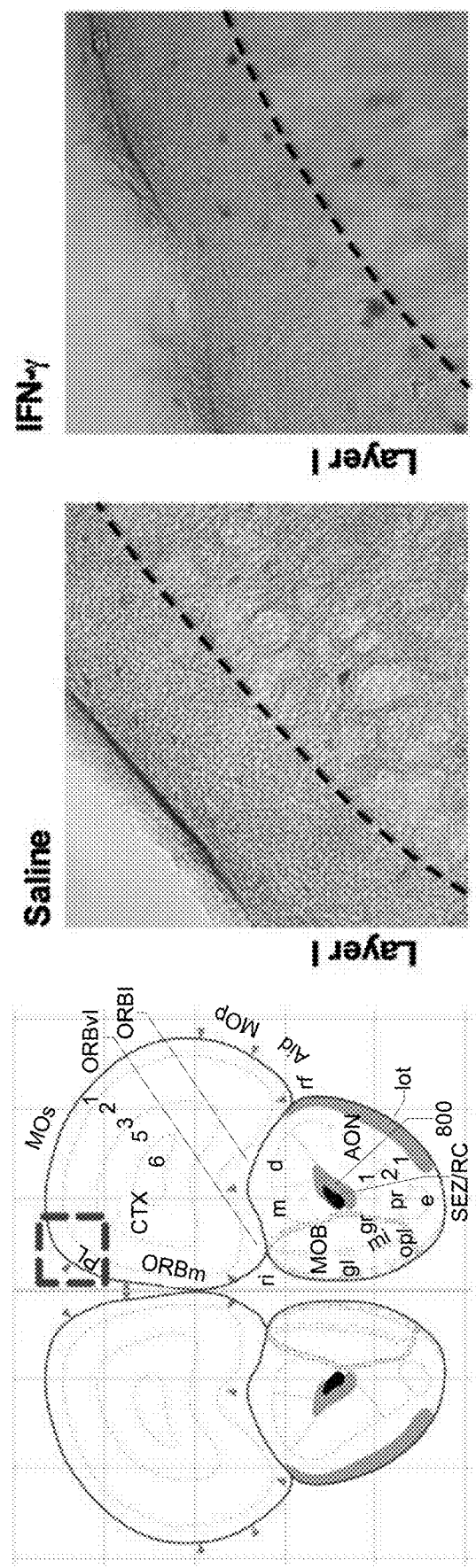
FIGS. 13A-13F show that IFN-γ increased the number of c-fos+ cells in Layer I of the PFC.
Figures 13D, 13E, 13F:
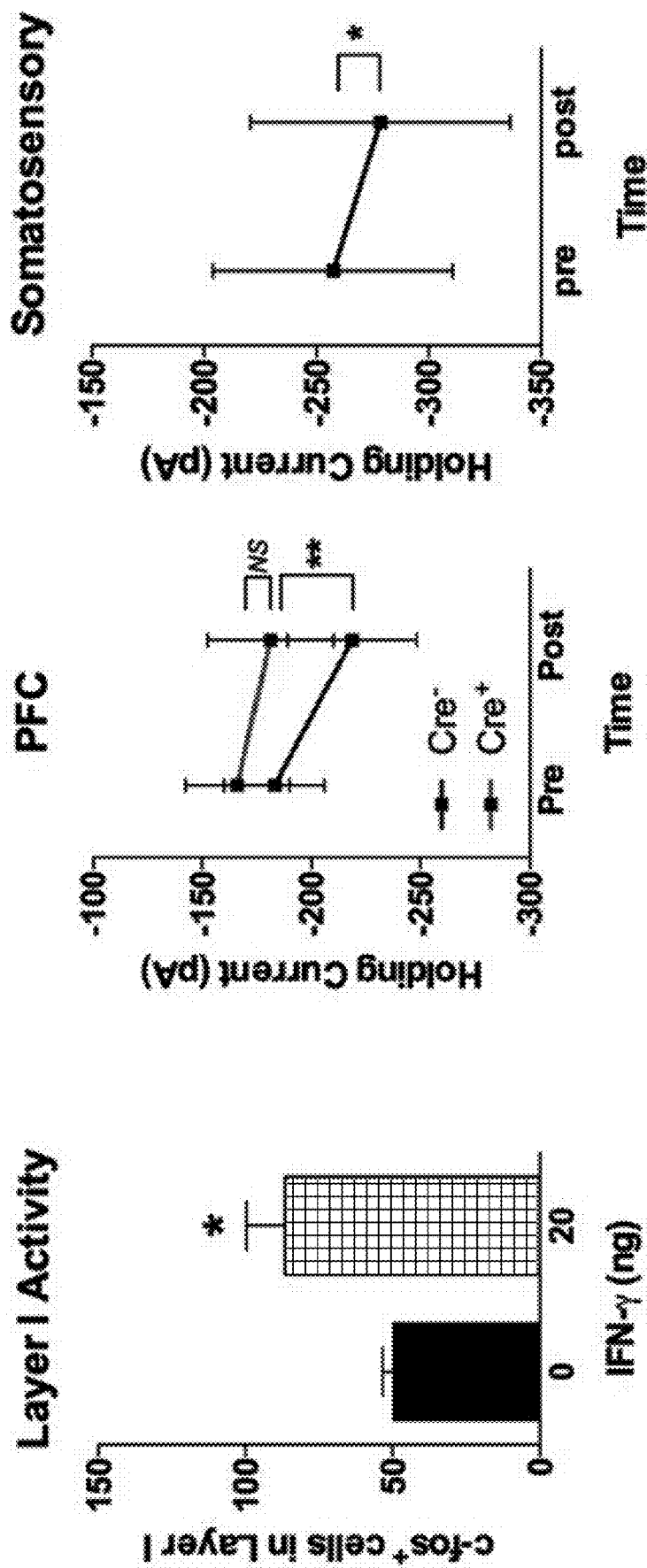

To directly assess if IFN-γ can drive inhibitory tone in the PFC, inhibitory currents in layer 2/3 pyramidal cells from acutely prepared brain slices from wild-type mice were measured. In addition to receiving phasic inhibitory synaptic input, these cells are also held under a tonic GABAergic current that serves to hyperpolarize their resting membrane potential (FIG. 2I). Tonic GABAergic currents are extrasynaptic and can yield longlasting network inhibition[19]. IFN-γ augmented tonic current was observed (FIGS. 2I, 2J, FIGS. 13E-13F), suggestive of elevated levels of ambient GABA during application of IFN-γ. Deleting the IFN-γ receptor from inhibitory neurons (VgatCre::Ifngrl fl/fl mice) prevented IFN-γ from augmenting tonic inhibitory current (FIG. 13E). Given that IFN-γ promotes inhibitory tone, we tested if IFN-γ could prevent aberrant neural discharges by injecting IFN-γ into the CSF and then chemically inducing seizures with the GABA type A receptor antagonist, pentylenetetrazole (PTZ). Mice injected with IFN-γ were less susceptible to PTZ induced seizures; IFN-γ delayed seizure onset and lowered seizure severity (FIG. 2K). Further, to test if overexcitation causes social deficits in IFN-γ deficit mice, Ifng–/–mice were treated with diazepam to augment GABAergic transmission[20]. Diazepam successfully rescued social behavior of Ifng–/–mice, similar to the effect observed with recombinant IFN-γ treatment (FIG. 2L), suggesting that social deficits, due to a deficiency in IFN-γ, may arise from inadequate control of GABAergic inhibition by IFN-γ.

Figure 3G:
Figure 3G:
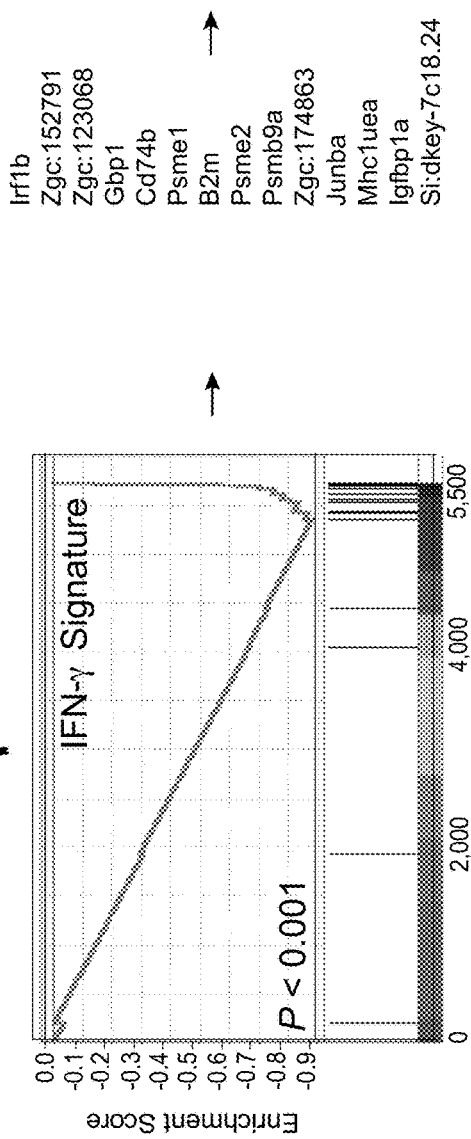
Figure 3H:
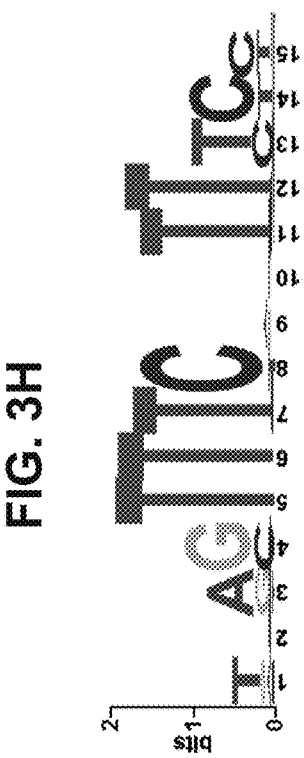
Figure 3I:
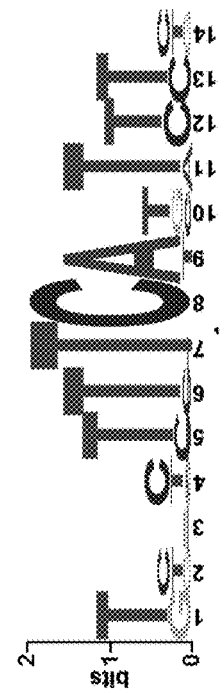

It is intriguing that IFN-γ, predominately thought of as an anti-pathogen cytokine, can play such a profound role in maintaining proper social function. Since social behavior is crucial for the survival of a species and aggregation increases the likeliness of spreading pathogens, there may have been co-evolutionary pressure to increase an antipathogen response as sociability increased, and the IFN-γ pathway may have influenced this co-evolution. Metadata of publically available transcriptomes from multiple organisms including the rat, mouse, zebrafish, and fruit flies were analyzed. Using GSEA, it was determined that transcripts from social rodents (acutely group housed) are enriched for an IFN-γ responsive gene signature (FIGS. 3A-3C, FIGS. 3D-3F; Supplementary Tables 3-7). Conversely, rodents that experienced social isolation demonstrated a dramatic loss of the IFN-γ responsive gene signature (Supplementary Tables 3-7). Zebrafish and flies showed a similar association between anti-pathogen and social responses (FIGS. 3G-3I, FIGS. 3J-3L). Immune response programs were highly enriched in the brain transcriptomes of flies selected for low aggressiveness traits (a physiological correlate for socially experienced flies[21]; FIGS. 3J-3L; Supplementary Tables 3-7). Analyses of the promoters of these highly upregulated social genes showed that they are enriched for STAT1 transcription factor binding motifs (FIGS. 3A-3L). These data suggest, even in the absence of infection, an IFN-γ gene signature is upregulated in aggregated organisms. This is consistent with an interaction between social behavior and the anti-pathogen response, a dynamic that could be mediated by the IFN-γ pathway. Since low-aggressive flies upregulate genes in the JAK/STAT pathway (canonically downstream of IFN-γ receptors in higher species), yet lack IFN-γ or T cells, it may be that T cell-derived IFN-γ has evolved in higher species to more efficiently regulate an anti-pathogen response during increased aggregation of individuals.

These results reveal a novel role for meningeal immunity in regulating neural activity and social behavior through IFN-γ. The role of immune molecules has been previously shown to control brain development and function[22-26] and a role for cytokines in influencing behavior has been proposed, primarily in the context of sickness behavior and pain[27, 28]. These signaling paradigms, however, have predominately focused on peripheral nerves and non-neuronal targets. As shown herein, CNS neurons directly respond to IFN-γ derived from meningeal T cells to elevate tonic GABAergic inhibition and prevent aberrant hyper-excitability in the PFC. These data suggest that social deficits in numerous neurological and psychiatric disorders may result from impaired circuitry homeostasis derived from dysfunctional immunity. Based on these findings, it is also plausible that subtle homeostatic changes in meningeal immunity may also contribute to modulating neuronal circuits that are responsible for our everyday behaviors and personality. Given this communication between immunity and neuronal circuits[29], these pathways may be vulnerable to manipulation by fast-evolving pathogens.

Methods of Treatment for Social Dysfunction Neurological Disorders

The present disclosure provides methods for treating social dysfunction neurological disorders in an animal subject, comprising administering to the subject a therapeutically effective amount of a compound that increases STAT1 activity. In some aspects, the animal subject is a human.

In some embodiments, the compound that increases STAT1 activity comprises IFN-γ. In some embodiments, the compound comprises STAT1. In further embodiments the compound increases STAT1 activity in GABAergic inhibitory neurons. In some embodiments, the compound increases GABAergic transmission. In some embodiments the compound is a GABA receptor agonist and/or a positive allosteric modulator. In some embodiments, the compound is a benzodiazepine compound. In some embodiments the benzodiazepine compound is diazepam.

In some embodiments the method of treating comprises the step of identifying a subject in need of said treatment. In further embodiments the subject in need of said treatment is susceptible to or suffering from a social dysfunction neurological disorder, such as autism spectrum disorder (ASD), frontotemporal dementia, and schizophrenia. Identification of such subjects may be made using techniques known to a person of ordinary skill in the art.

In some aspects, the administration of the compound is into the cerebrospinal fluid (CSF) of said subject. In some embodiments, an ointment comprises said compound and wherein the administration is via application of the ointment to the head of said subject. In some embodiments the compound is administered to the scalp skin of the subject.

Methods of Treatment for Seizures

The present disclosure further provides methods of treating seizures in an animal subject, comprising administering to the subject a therapeutically effective amount of a compound that increases STAT1 activity. In some aspects, the animal subject is a human.

In some embodiments the method of treating comprises the step of identifying a subject in need of said treatment. In further embodiments the subject in need of said treatment is susceptible to or suffering from seizures. Identification of such subjects may be made using techniques known to a person of ordinary skill in the art.

In some embodiments, the compound that increases STAT1 activity comprises IFN-γ. In some embodiments, the compound comprises STAT1. In further embodiments the compound increases STAT1 activity in GABAergic inhibitory neurons. In some embodiments, the compound increases GABAergic transmission.

In some aspects, the administration of the compound is into the cerebrospinal fluid (CSF) of said subject. In some embodiments, an ointment comprises said compound and wherein the administration is via application of the ointment to the head of said subject. In some embodiments the compound is administered to the scalp skin of the subject.

Pharmaceutically Acceptable Compositions

According to another embodiment, the present invention provides a composition or pharmaceutical composition comprising a compound or therapeutic agent and a pharmaceutically acceptable carrier, adjuvant, or vehicle. In some embodiments, the compound or therapeutic agent of the composition or pharmaceutical composition comprises a compound that increases STAT1 activity. In some embodiments, the compound or therapeutic agent of the composition or pharmaceutical composition comprises IFN-γ. In some embodiments, the compound or therapeutic agent of the composition or pharmaceutical composition comprises STAT1. In some embodiments the compound or therapeutic agent of the composition or pharmaceutical composition increases STAT1 activity in GABAergic inhibitory neurons. In some embodiments, the compound or therapeutic agent of the composition or pharmaceutical composition increases GABAergic transmission. In some embodiments the compound or therapeutic agent of the composition or pharmaceutical composition is a GABA receptor agonist and/or a positive allosteric modulator. In some embodiments, the compound or therapeutic agent of the composition or pharmaceutical composition is a benzodiazepine compound. In some embodiments the benzodiazepine compound is diazepam.

The amount of therapeutic agent is an amount effective to treat the relevant disease, disorder, or condition in a subject in need thereof, e.g., social dysfunction neurological disorders, seizures disorders. In certain embodiments, a composition of this invention is formulated for administration to a subject in need of such composition. In some embodiments, a composition of this invention is formulated for oral administration to a subject. In some embodiments, a composition of this invention is formulated for injection into a subject. In some embodiments, a composition of this invention is formulated for topical application to the skin.

The term "subject," as used herein, means an animal, for example a mammal, such as a human.

The term "pharmaceutically acceptable carrier, adjuvant, or vehicle" refers to a non-toxic carrier, adjuvant, or vehicle that does not destroy the pharmacological activity of the compound or therapeutic with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. The compositions may be administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

In some embodiments, the pharmaceutical compositions are administered by an oral, intravenous, subcutaneous, intranasal, inhalation, intramuscular, intraocular, intraperitoneal, intratracheal, transdermal, buccal, sublingual, rectal, topical, local injection, or surgical implantation route. In some embodiments, the administration route is oral. In some embodiments, the administration is via injection. In some embodiments, the administration is via local injection. In some embodiments, the administration of the compound is into the cerebrospinal fluid (CSF) of said subject. In some embodiments, the administration is transdermal, e.g., via application of an ointment containing the therapeutic to the head of said subject.

To aid in delivery of the pharmaceutical composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions may also be administered topically, especially when the target of treatment includes areas or organs readily accessible by topical application, such as the skin (e.g., scalp skin), or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of a therapeutic include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions are formulated for oral administration. Such formulations may be administered with or without food. In some embodiments, pharmaceutically acceptable compositions are administered without food. In other embodiments, pharmaceutically acceptable compositions of this invention are administered with food.

The amount of therapeutic that may be combined with the carrier materials to produce a composition in a single dosage form will vary depending upon the host treated, the particular mode of administration, and other factors known to one of ordinary skill. Preferably, provided compositions should be formulated so that a dosage of between 0.01-100 mg/kg body weight/day of the therapeutic agent can be administered to a patient receiving these compositions.

It should also be understood that a specific dosage and treatment regimen for any particular patient will depend upon a variety of factors, including the activity of the specific therapeutic employed, the age, body weight, general health, sex, diet, time of administration, rate of excretion, drug combination, and the judgment of the treating physician and the severity of the particular disease being treated. The amount of a therapeutic in the composition will also depend upon the particular therapeutic in the composition.

Pharmaceutically acceptable compositions comprising a therapeutic and a pharmaceutically acceptable excipient, diluent, or carrier, are useful for treating a variety of diseases, disorders or conditions. Such diseases, disorders, or conditions include those described herein.

EXAMPLES

Example 1. Mice Models

All mice (C57BL/6) were either bred in-house or purchased from the Jackson Laboratory. For each individual experiment, the control mice were obtained from the same institution as test mice. In the case that mice were purchased, they were maintained for at least one week to habituate prior to manipulation/experimentation. When possible, mice used for experiments were littermates. These include all electrophysiology experiments, all cohorts using STAT1 fl/fl mice, experiments analyzing induced seizures, experiments counting c-fos+ neurons, and experiments using Il4−/− mice. Experiments assessing the social behavior of SCID mice using the 3-chamber assay include mice breed in-house and mice purchased from the Jackson Laboratory. All other experiment used mice purchased from the Jackson Laboratory. Experimental groups were blinded and randomly assigned prior to the start of experimentation and remained blinded until all data were collected. Mice were housed under standard 12 hour light/dark cycle conditions in rooms equipped to control for temperature and humidity. Unless stated otherwise, male mice were tested at 8-10 weeks of age. Sample sizes were chosen based on a power analysis using estimates from previously published experiments. All experiments were approved by the Institutional Animal Care and Use Committee of the University of Virginia.

Example 2. Behavioral Studies

For cohorts tested with multiple behavioral assay, the elevated plus-maze was performed first and then followed by the open field before any other assay. Prior to all experiments, mice were transported to the behavior room and given 1 hour to habituate. All behavioral testing was conducted during daylight hours.

Elevated Plus-Maze

Mice were placed into the center hub and allowed to explore the plus-maze for 10 minutes. Video tracking software (CleverSys) was used to quantify time spent in the open arms.

Open Field

Mice were placed into the open field (35 cm×35 cm) and allowed to explore for 15 minutes. Total distance and time spent in the center (23 cm×23 cm) were quantified using video tracking software (CleverSys).

Rotarod

Mice were placed on an accelerating rotarod (MedAssociates) that accelerated from 4.0-40 rpm over 5 minutes. Infrared beams were used to quantify the latency of a mouse to fall of the rod. Mice were given 6 trials with a 4-hour break between trial 3 and 4.

Three-Chamber Sociability Assay

The three-chamber sociability test was conducted as previously described[31]. Briefly, mice were transported to the testing room and habituated for at least one hour. The room was maintained in dim light and a white noise generator used to mitigate any unforeseen noises. Test boxes were fabricated, in-house, by a machine shop. Test mice were placed in the center chamber with the two outer chambers containing empty wire cages (Spectrum Diversified Designs) and allowed to explore for ten minutes (habituation phase). After the habituation phase, mice were return to the center chamber. A novel mouse (an 8-10 week old male C57BL/6J~18-22 g) was placed under one cup and an object placed under the other. Prior to testing, the novel mouse was habituated to the cup by being placed under the cup for 10 minutes, 3 times a day for 5 days. Mice were allowed to explore for an additional ten minutes (social phase). A video tracking system (CleverSys) was used to quantify the time spent around each target. For 3-chamber experiments comparing social behavior between wild-type and SCID mice, data collected using males and females were combined because no significant effects were found between genders. When females were tested, juvenile C57BL/6J male (approximately 4 weeks old) mice were used as novel demonstrators.

Novel/Social Environment

Mice were single housed and maintained un-manipulated for 5 days, then placed in a novel/social environment with a mouse (opposite sex and identical scid genotype) under video surveillance as previously described[31]. After 2 hours, mice were sacrificed and prepared for immunohistochemistry as described below. The time spent interacting was measured by a blinded observer for 5 minutes at the 30, 60, and 90 minute postintroduction time points.

Example 3. Resting-State fMRI

The protocol for rsfMRI was adapted from Zhan et al.[32]. Mice were maintained under light anesthesia with (1-1.25%) isoflurane and images were acquired on a 7.0 Tesla MRI Clinscan system (Bruker, Etlingen, Germany) using a 30-mm inner-diameter mouse whole-body radiofrequency coil. High-resolution structural images were acquired by collecting 16×0.7 mm thick coronal slices using TR/TE 5,500/65 ms and an 1800 flip angle. A BOLD rsfMRI time series of 16×0.7 mm thick coronal slices were collected using TR/TE 4,000/17 ms and a 60o flip angle. For analysis, a structural template[33] was custom labeled using "The Mouse Brain" by Paxinos and Franklin as reference (FIGS. 6A-6C). The non-rigid transformation between the template and each individual mouse was estimated using the open source Advanced Normalization Tools (ANTs) package[34] that was then used to propagate the regional labels to each subject. Cleaning of the bold fMRI data was performed using tools available in ANTsR[35]—a statistical and visualization interface between ANTs and the R statistical project. fMRI preprocessing consisted of motion correction[36], band pass filtering (freq.=[0.002, 0.1]), and CompCor estimation[37]. The correlation matrix was determined from the clean fMRI data using the regions labels. To determine if the functional connectivity between sample groups was significantly different, we tested for the equality of their corresponding correlation matrices. First, an aggregate correlation matrix was constructed for each group by calculating the median value for each connection, and then the aggregate matrices were compared using the Jennrich test[38], as implemented in the cortest.jennrich function in the R psych package. To create a functional connectivity network for a sample group, a correlation threshold was applied to the connections between regions of interest. If a connection strength was above the threshold, it was kept as an edge in the network, otherwise it was discarded. When comparing networks from multiple sample groups, the threshold was determined by calculating the maximum threshold that leaves one of the networks connected (i.e., it is possible to reach any node in the network from any other node).

Example 4. Immunohistochemistry

Mice were sacrificed under Euthasol then transcardially perfused with PBS with heparin. Brains were removed and drop fixed in 4% PFA for 48 hours. After fixation, brains were washed with PBS, cryoprotected with 30% sucrose, then frozen in O.C.T. compound (Sakura Finetek) and sliced (40 μM) with a cryostat (Leica). Free-floating sections were maintained in PBS+Azide (0.02%) until further processing. Immunohistochemistry for c-fos (1:1000 dilution; Millipore) on free-floating sections was performed as previously described[39].

Example 5. Depletion of Meningeal T Cells

A rat monoclonal antibody to murine VLA4 (clone PS/2) was affinity purified from hybridoma supernatants and was used with the kind permission of Dr. Klaus Ley (La Jolla Institute of Allergy and Immunology, San Diego, Calif.). Mice were given two separate injections (i.p.; 0.2 mg in saline per mouse), four days apart, of either anti-VLA4 or rat anti-HRP for control (clone HRPN; BioXcell), then tested twenty-four hours post final injection.

Example 6. Dissection of Meninges and Flow Cytometry

Meninges were dissected as previously described[40]. Briefly, after sacrificing and perfusing, skulls caps were removed by making an incision along the parietal and squamosal bones. The meninges were removed from the internal side of the skull cap and gently pressed through a 70 µm nylon mesh cell strainer with sterile plastic plunger (BD Biosciences) to isolate a single cell suspension. Cells were then centrifuged at 300 g at 4° C. for 10 min, resuspended in cold FACS buffer (pH 7.4; 0.1 M PBS; 1 mM EDTA; 1% BSA), and stained for extracellular markers using the following antibodies at a 1:200 dilution: CD45 PerCP-Cyanine5.5 (eBioscience), TCR BV510 (BD Bioscience), CD4 FITC (eBioscience), LID Zombie NIR (BioLegend). To measure intracellular IFN-γ, single cell isolates from meninges were maintained in T cell isolation buffer (RPMI+2% FBS, 2 mM L-glutamine, 1 mM sodium pyruvate, 10 mM HEPES, 1× non-essential amino acids, and 1× Antibiotic-Antimycotic (Thermo Fisher) and stimulated with PMA/ionomycin (Cell Stimulation Cocktail-eBioscience)+10 µg/ml brefeldin A at 37° C. prior to extracellular staining as stated above. Cells were then permeabilized with Cytofix/Cytoperm (BD Biosciences) and stained with IFN-γ APC (eBioscience; clone XMG1.2).

To measure expression of IFN-γ receptors, brains were removed and placed in Neurobasal media containing 10% fetal bovine serum. The meninges were removed from the brain and the frontal cortex was micro-dissected under a dissection microscope. Using a 2 mL dounce homogenizer, brains were homogenized in Neurobasal media with 50 U/mL Dnase I. The homogenate was passed through a 70 µm nylon filter and washed with cold FACS buffer. IFNGR were labeled with anti-IFNGR I Biotin (BD Pharmingen; GR20) or rabbit anti-IFNGR2 (Santa Cruz; M-20). Cells were washed with FACS buffer and incubated with FITC conjugated streptavidin or 488 conjugated chicken anti-rabbit. Next, cells were washed again then incubated with CD11B PE-Cyanine7 (eBioscience), LID Zombie NIR (BioLegend), and Hoechst for 45 minutes. Cells were washed, then permeabilized and fixed with Cytofix/Cytoperm (BD Biosciences). After another wash with permeabilization wash buffer (PBS with 10% fetal bovine serum, 1% sodium azide, and 1% saponin; pH 7.4), cells were incubated overnight with NeuN PE (Millipore). Cells underwent a final wash and again passed through a 70 µm nylon filter. Samples were run on a flow cytometer Gallios (Beckman Coulter) then analyzed using FlowJo software (Treestar).

Example 7. SCID Repopulation

SCID mice were repopulated with cells from spleen and lymph nodes (axillary, brachial, cervical, inguinal, and lumbar). Spleen and lymph nodes were collected from a 3-4 week old donor and passed through a 70 µm nylon mesh cell strainer with a sterile plastic plunger. ACK buffer was used to lyse red blood cells prior to washing with saline. Cells were counted on an automated cell counter (Nexcelom) and injected (i.v.) at 5×106 cells in 250 µL of saline (control mice were injected with 250 µL of saline only). For injections, the animal technician was blinded to the genotype of the mice and the content of the injection. Thus, all groups were handled identically. Mice aged 3-4 weeks were carefully placed into a tail vein injection platform. Their tails were briefly warmed using a heating pad and saline with cells or saline alone was slowly injected into the tail vein using a 28 G needle. After the injection, mice were returned to their home cage.

Example 8. IFN-γ Injections

Mice were anaesthetized with a ketamine/xylazine [ketamine (100 mg/kg) and xylazine (10 mg/kg)] injection (i.p.) or isoflurane (2%), then placed into a stereotaxic frame with the head at an approximately 45° angle. The skin above cisterna magna was cleaned and sanitize before a 1 cm incision was made. The underlying muscles were separated with forceps, retracted, and a small Hamilton syringe (33 G) was used to slowly inject 1 uL of saline or IFN-γ (20 ng; eBioscience) into the cisterna magna (i.c.m.). After injection the syringe was held in place for 5 minutes to avoid back-flow of CSF. After the syringe was removed, muscles were put back in place and skin was sutured. Mice were placed on a heating pad and given ketoprofen and baytril for recovery.

Example 9. Induced Seizures

IFN-γ was injected (i.c.m.) into the CSF through the cisterna magna (i.c.m.), as described above, 24 hours prior to inducing seizures. Control mice were injected with the same volume of saline. To induce seizures, mice were injected with PTZ (40 mg/kg; i.p.). After injection, mice were placed into an empty housing cage and recorded for video analysis. Seizures were analyzed by a blinded observer using a behavior scoring system previously published[41].

Example 10. Diazepam Treatment

Diazepam (1.25 mg/kg) was delivered i.p. for 30 minutes prior to testing for social behavior.

Example 11. Fluorescent In Situ Hybridization

Mice were euthanized then transcardially perused with PBS with heparin followed by 4% PFA. Brains were then removed and drop fixed in 4% PFA for 24 hours, frozen in OCT, and 12 µM sections were cut on a cryostat. Fluorescent in situ hybridization was performed using RNA ISH tissue assay kits (Affymetrix) following the manufacture's protocol. Tissues were treated with protease for 20 minutes at 40° C. 63× Images were acquired on a Leica TCS SP8 confocal system (Leica Microsystems) using the LAS AF Software.

Example 12. AAV Delivery

AAV1.hSyn.HI.eGFP-Cre.WPRE.SV40 and AAV1.hSyn.eGFP.WPRE.bGH were purchased from Penn Vector Core. IFNGR lfl/fl mice were purchased from the Jackson lab. After 1 week of habituation, mice were anesthetized with 2% isoflurane and injected bilaterally with 2×1010 genome copies of AAV virus in 1 µL at stereotaxic coordinates: +2.5 µM bregma A/P, 0.25 µM lateral, 1.25 µM deep.

Example 13. Measuring Inhibitory Currents

Visualized whole-cell patch-clamp recordings were performed on layer 2/3 prefrontal cortical neurons prepared from acute brain slices (adult) using the protective recovery method[42]. Recordings were performed in 34° C. artificial cerebrospinal fluid (ACSF) containing (in mM) 131.5 NaCl, 25 NaHCO$_3$, 12 D-glucose, 2.5 KCl, 1.25 NaH2PO4, 2 CaCl2, and 1 MgCl2. ACSF also contained 3 mM kynurenic acid to block synaptic excitation and 2.5 mM NO-711 to enhance tonic inhibition[43]. Slices were incubated in this ACSF for 5-10 minutes prior to placement in the recording chamber. The patch pipette solution with elevated chloride contained (in mM) 140 CsCl, 4 NaCl, 1 MgCl2, 10 HEPES, 0.05 EGTA, 2 Mg-ATP, and 0.4 Mg-GTP[43]. Once recordings equilibrated, baseline holding current in ACSF was measured for 3.5 minutes, after which ACSF containing IFN-γ (20 pg/mL) was applied for 8.5 minutes and then washed. Data presented show the mean holding current during the last minute of control (ACSF) and drug (ACSF+IFN-γ) conditions.

Example 14. Transcriptome Analysis Studies

RNA Isolation and Sequencing 8 week old, male mice were purchased from The Jackson Lab and housed in standard housing boxes either 4 mice per cage or isolated for 6 days. Mice were euthanized as described above and the PFC was microdissected under a dissection microscope. RNA was isolated using RNAeasy mini kit (Qiagen) and a cDNA library was generated with a TruSeq Stranded mRNA Library Prep Kit (Illumina) with Agencourt AMPure XP beads for PCR cleanup. Samples were loaded onto a NextSeq 500 High-output 75 cycle cartridge and sequenced on a NextSeq 500 (Illumina).

Transcriptome Analysis

Raw FASTQ sequencing reads were chastity filtered to remove clusters having outlying intensity corresponding to bases other than the called base. Filtered reads were assessed for quality using FastQC[44]. Reads were splice-aware aligned to the UCSC mm9 genome using STAR[45], and reads overlapping UCSC mm9 gene regions were counted using featureCounts[46]. The DESeq2 Bioconductor package[47] in the R statistical computing environment[48] was used for normalizing count data, performing exploratory data analysis, estimating dispersion, and fitting a negative binomial model for each gene comparing the expression from the PFC of mice in a social environment versus isolation. After obtaining a list of differentially expressed genes, log fold changes, and P-values, Benjamini-Hochberg False Discovery Rate procedure was used to correct P-values for multiple testing. A Gene Set Enrichment Analysis (GSEA) algorithm[49] was applied to identify the enrichment of transcriptional signatures and molecular pathways in PFC transcriptomes of mice exposed to group and isolation housing conditions. 4726 publicly available transcriptional signatures were obtained from the molecular Signature Database C2 version 4.0 and GSEA was used to examine the distribution of these curated gene sets in lists of genes ordered according to differential expression between group and isolation housing conditions. The statistical analysis was performed by evaluation of nominal Pvalue and normalized enrichment score (NES) based on 1,000 random sample permutations.

Meta-Data Analysis

The custom-made IFN-γ and pathogen-induced transcriptional signatures (Supplementary Table 2) were generated by retrieving genes upregulated ≥2 fold following IFN-γ stimulation or pathogen infection. All custom signatures were derived from publicly available transcriptomes downloaded from Gene Expression Omnibus (GEO). Specifically, mammalian IFN-γ transcriptional signatures were derived from transcriptomes: GSE33057, GSE19182, GSE36287, GSE9659, GSE1432 and GSE6353. Zebrafish IFN-γ transcriptional signature was used as described[50]. Drosophila pathogen induced JAK/STAT-dependent transcriptional signatures were derived from transcriptomes: GSE54833 and GSE2828. A GSEA algorithm was applied to identify the enrichment of custom-made mammalian IFN-γ transcriptional signatures in the publicly available brain cortex transcriptomes of mice and rats exposed to: social aggregation, sleep deprivation, stress, psychostimulants (DOI, cocaine, amphetamine, methamphetamine, methylphenidate, caffeine, nicotine and modafinil), antipsychotics (olanzapine, haloperidol and risperidone), anticonvulsants (levetiracetam, phenytoin, ethosuximide and oxcarbazepine), and antidepressants (iproniazid, moclobemide, paroxetine and phenelzine). In total, 41 transcriptomes were analyzed as indicated in Supplementary Table 2. The statistical analysis was performed by evaluation of nominal P-value and NES based on 1,000 random sample permutations. Zebrafish are social fish that aggregate into shoals[51-54]. Various Zebrafish strains differ in their preference for social interaction and novelty, resembling the phenotypic variation of inbred mouse strains[55, 56]. Notably, domesticated zebrafish strains demonstrate higher social interaction and social novelty preference[51-59] compared to wild zebrafish strains. Therefore, a GSEA algorithm was used to identify the enrichment of Zebrafish IFN-γ transcriptional signature in the publicly available whole-brain transcriptomic profiles of behaviorally distinct strains of domesticated and wild zebrafish (Supplementary Table 7). The brain transcriptomic profiles of domesticated (Scientific Hatcheries (SH) and Transgenic Mosaic 1 (TM1)) and wild (Nadia, Gaighata) zebrafish strains were derived from publicly available transcriptome data set: GSE38729. The statistical analysis was performed by evaluation of nominal P-value and NES based on 1,000 random gene set permutations. Social interactions in Drosophila melanogaster flies play an important role in courtship, mating, egg-laying, circadian timing, food search and even lifespan determination[60-65]. Notably, a number of studies have demonstrated that social isolation leads to an aggressive behavior in Drosophila flies, whereas group housing suppresses the aggressiveness[66-68]. Therefore, we employed a GSEA algorithm to identify the enrichment of JAK/STAT-dependent transcriptional signatures in the publicly available brain transcriptomes of Drosophila populations that were socially-induced or genetically selected for low-aggressive (i.e. social) behavior (Supplementary Table 7). The transcriptomic profiles were derived from publicly available transcriptome data sets: GSE5404 and GSE6994. The statistical analysis was performed by evaluation of nominal P-value and NES based on 1,000 random gene set permutations.

Promoter Motif Analysis

A GSEA algorithm was used to identify genes that are differentially expressed in brain transcriptomes of mice and rats exposed to social aggregation, domesticated Zebrafish strains and low-aggressive Drosophila melanogaster populations, compared to their control counterparts. High-scoring differentially expressed "leading-edge" social genes were selected based on their presence in the IFN-γ and pathogen-induced transcriptional signatures. Specifically, as shown in FIGS. 3A-3L, 31, 48, 14, 53 leading edge genes were identified in brain transcriptomes of mice and rats exposed to social aggregation, domesticated Zebrafish strain, and low-aggressive Drosophila melanogaster population, respectively. Next, promoter sequences of 200 bp up-stream of TSS of these "leading edge" genes were extracted using UCSC Genome Browser (genome.ucsc.edu). The MEME suite was then used to discover overrepresented transcription factor binding motifs, as described[69]. MEME parameters used were any number of motif repetitions per sequence, with a minimum motif width of 5 bases and maximum motif width of 15 bases. The discovered MEME motifs were compared using Tomtom analysis. In this case, the Tomtom motif similarity analysis ranks the MEME motif most similar to the Vertebrates in vivo and in silica, canonical motif for STAT. The statistics was determined using Euclidean distance.

Circos Plot

A GSEA algorithm was applied to identify the enrichment of IFN-γ, IL-4/IL-13, IL-17, and IL-10/TGF-β signaling pathways in the brain transcriptomes of rodent animals exposed to: social aggregation, stress, psychostimulants, antipsychotics, and antidepressants. All custom signatures were derived from publically available rodent transcriptomes downloaded from Gene Expression Omnibus. Statistical significance of GSEA results was assessed using 1,000 sample permutations. A NES greater than 1.5 and nominal P-value less than 0.05 was used to determined pairwise transcriptome connectivity. Circos graph was generated using circus package 0.68.12[70].

Example 15. Statistics

Data were analyzed using the statistical methods stated in each figure legend. For the 3-chamber assay, a 2-way ANOVA was performed using genotype/treatment and sociability as main effects, followed by applying a Sidak's post-hoc comparison to assess if the group had a significant social preference. Prior to running an ANOVA, an equality of variance was determined by using a Brown-Forsythe test. Bars display the means, and error bars represent ranges of the standard error of the mean. For rsfMRI, data were analyzed using a 1-way ANOVA followed by a post-hoc Tukey's test. The box and whisker plots extend to the 25th and 75th percentiles and the center line indicates the mean. The whiskers represent the min and max data points. Data for seizure latency was analyzed using a 2-way ANOVA with repeated measures followed by a post-hoc Sidak test. Additional details of statistical analysis are supplied in Supplementary Table 8.

REFERENCES

1. Derecki, N. C. et al. Regulation of learning and memory by meningeal immunity: a key role for IL-4. J Exp Med 207, 1067-1080, doi:10.1084/jem.20091419 (2010).
2. Bourke, A. F. Hamilton's rule and the causes of social evolution. Philosophical Transactions of the Royal Society of London. Series B, Biological sciences 369, 20130362, doi:10.1098/rstb.2013.0362 (2014).
3. Cacioppo, S., Capitanio, J. P. & Cacioppo, J. T. Toward a neurology of loneliness. Psychol Bull 140, 1464-1504, doi:10.1037/a0037618 (2014).
4. Kennedy, D. P. & Adolphs, R. The social brain in psychiatric and neurological disorders. Trends Cogn Sci 16, 559-572, doi:10.1016/j.tics.2012.09.006 (2012).
5. Ashwood, P. et al. Altered T cell responses in children with autism. Brain Behav Immun 25, 840-849, doi:10.1016/j.bbi.2010.09.002 (2011).
6. Gupta, S., Aggarwal, S., Rashanravan, B. & Lee, T. Th1- and Th2-like cytokines in CD4+ and CDS+ T cells in autism. J Neuroimmunol 85, 106-109 (1998).
7. Waisman, A., Liblau, R. S. & Becher, B. Innate and adaptive immune responses in the CNS. Lancet Neurol 14, 945-955, doi:10.1016/S1474-4422(15)00141-6 (2015).
8. Moy, S. S. et al. Sociability and preference for social novelty in five inbred strains: an approach to assess autistic-like behavior in mice. Genes Brain Behav 3, 287-302, doi: 10.1111/j.1601-1848.2004.00076.x (2004).
9. Silverman, J. L., Yang, M., Lord, C. & Crawley, J. N. Behavioural phenotyping assays for mouse models of autism. Nat Rev Neurosci 11, 490-502, doi:10.1038/nrn2851 (2010).
10. Nelson, S. B. & Valakh, V. Excitatory/Inhibitory Balance and Circuit Homeostasis in Autism Spectrum Disorders. Neuron 87, 684-698, doi:10.1016/j.neuron.2015.07.033 (2015).
11. Supekar, K. et al. Brain hyperconnectivity in children with autism and its links to social deficits. Cell Rep 5, 738-747, doi:10.1016/j.celrep.2013.10.001 (2013).
12. Zhan, Y. et al. Deficient neuron-microglia signaling results in impaired functional brain connectivity and social behavior. Nat Neurosci 17, 400-406, doi:10.1038/nn.3641 (2014).
13. Shen, H. H. Core Concept: Resting-state connectivity. Proc Natl Acad Sci USA 112, 14115-14116, doi:10.1073/pnas.1518785112 (2015).
14. Brynskikh, A., Warren, T., Zhu, J. & Kipnis, J. Adaptive immunity affects learning behavior in mice. Brain Behav Immun 22, 861-869, doi:10.1016/j.bbi.2007.12.008 (2008).
15. Yednock, T. A. et al. Prevention of experimental autoimmune encephalomyelitis by antibodies against alpha 4 beta 1 integrin. Nature 356, 63-66, doi: 10.1038/356063a0 (1992).
16. Kunis, G. et al. IFN-gamma-dependent activation of the brain's choroid plexus for CNS immune surveillance and repair. Brain 136, 3427-3440, doi:10.1093/brain/awt259 (2013).
17. Tsuda, M. et al. IFN-gamma receptor signaling mediates spinal microglia activation driving neuropathic pain. Proc Natl Acad Sci USA 106, 8032-8037, doi:10.1073/pnas.0810420106 (2009).
18. Prieto, J. J., Peterson, B. A. & Winer, J. A. Morphology and spatial distribution of GABAergic neurons in cat primary auditory cortex (AI). J Comp Neurol 344, 349-382, doi:10.1002/cne.903440304 (1994).
19. Olah, S. et al. Regulation of cortical microcircuits by unitary GABA-mediated volume transmission. Nature 461, 1278-1281, doi:10.1038/nature08503 (2009).
20. Han, S., Tai, C., Jones, C. J., Scheuer, T. & Catterall, W. A. Enhancement of inhibitory neurotransmission by GABAA receptors having alpha2,3-subunits ameliorates behavioral deficits in a mouse model of autism. Neuron 81, 1282-1289, doi: 10.1016/j.neuron.2014.01.016 (2014).
21. Wang, L., Dankert, H., Perona, P. & Anderson, D. J. A common genetic target for environmental and heritable influences on aggressiveness in *Drosophila*. Proc Natl Acad Sci USA 105, 5657-5663, doi:10.1073/pnas.0801327105 (2008).
22. Datwani, A. et al. Classical MHCI molecules regulate retinogeniculate refinement and limit ocular dominance plasticity. Neuron 64, 463-470, doi:10.1016/j.neuron.2009.10.015 (2009).
23. Djurisic, M. et al. PirB regulates a structural substrate for cortical plasticity. Proc Natl Acad Sci USA 110, 20771-20776, doi:10.1073/pnas.1321092110 (2013).
24. Steinman, L. Inflammatory cytokines at the summits of pathological signal cascades in brain diseases. Sci Signal 6, pe3, doi:10.1126/scisignal.2003898 (2013).
25. Smith, L. K. et al. beta2-microglobulin is a systemic pro-aging factor that impairs cognitive function and neurogenesis. Nat Med 21, 932-937, doi:10.1038/nm.3898 (2015).

26 Villeda, S. A. et al. The ageing systemic milieu negatively regulates neurogenesis and cognitive function. Nature 477, 90-94, doi:10.1038/nature10357 (2011).

27 McCusker, R. H. & Kelley, K. W. Immune-neural connections: how the immune system's response to infectious agents influences behavior. J Exp Biol 216, 84-98, doi: 10.1242/jeb.0734 ll (2013).

28 Scholz, J. & Woolf, C. J. The neuropathic pain triad: neurons, immune cells and glia. Nat Neurosci 10, 1361-1368, doi:10.1038/nn1992 (2007).

29 Bhat, R. et al. Inhibitory role for GABA in autoimmune inflammation. Proc Natl Acad Sci USA 107, 2580-2585, doi:10.1073/pnas.0915139107 (2010).

30 Lopez-Munoz, A. et al. Evolutionary conserved pro-inflammatory and antigen presentation functions of zebrafish IFN gamma revealed by transcriptomic and functional analysis. Mal Immunol 48, 1073-1083, doi: 10.1016/j.molimm.2011.01.015 (2011).

31 Filiano, A. J. et al. Dissociation of frontotemporal dementia-related deficits and neuroinflammation in progranulin haploinsufficient mice. J Neurosci 33, 5352-5361, doi: 10.1523/JNEUROSCI.6103-11.2013 (2013).

32 Zhan, Y. et al. Deficient neuron-microglia signaling results in impaired functional brain connectivity and social behavior. Nat Neurosci 17, 400-406, doi:10.1038/nn.3641 (2014).

33 Johnson, G. A. et al. Waxholm space: an image-based reference for coordinating mouse brain research. Neuroimage 53, 365-372, doi:10.1016/j.neuroimage.2010.06.067 (2010).

34 A van ts, B. B. et al. A reproducible evaluation of ANTs similarity metric performance in brain image registration. Neuroimage 54, 2033-2044, doi: 10.1016/j.neuroimage.2010.09.025 (2011).

35 Avants, B. B. et al. The pediatric template of brain perfusion. Sci Data 2, 150003, doi:10.1038/sdata.2015.3 (2015).

36 Power, J. D., Barnes, K. A., Snyder, A. Z., Schlaggar, B. L. & Petersen, S. E. Spurious but systematic correlations in functional connectivity MRI networks arise from subject motion. Neuroimage 59, 2142-2154, doi:10.1016/j.neuroimage.2011.10.018 (2012).

37 Behzadi, Y., Restom, K., Liau, J. & Liu, T. T. A component based noise correction method (CompCor) for BOLD and perfusion based fMRI. Neuroimage 37, 90-101, doi: 10.1016/j.neuroimage.2007.04.042 (2007).

38 Jennrich, R. I. An Asymptotic x2 Test for the Equality of Two Correlation Matrices. Journal of the American Statistical Association 65, 904-912 (1970).

39 Palop, J. J., Mucke, L. & Roberson, E. D. Quantifying biomarkers of cognitive dysfunction and neuronal network hyperexcitability in mouse models of Alzheimer's disease: depletion of calcium-dependent proteins and inhibitory hippocampal remodeling. Methods Mal Biol 670, 245-262, doi:10.1007/978-1-60761-744-O_17 (2011).

40 Derecki, N. C. et al. Regulation of learning and memory by meningeal immunity: a key role for IL-4. J Exp Med 207, 1067-1080, doi:10.1084/jem.20091419 (2010).

41 Li, Z., Hall, A. M., Kelinske, M. & Roberson, E. D. Seizure resistance without parkinsonism in aged mice after tau reduction. Neurobiol Aging 35, 2617-2624, doi: 10.1016/j.neurobiolaging.2014.05.001 (2014).

42 Ting, J. T., Daigle, T. L., Chen, Q. & Feng, G. Acute brain slice methods for adult and aging animals: application of targeted patch clamp analysis and optogenetics. Methods Mal Biol 1183, 221-242, doi:10.1007/978-1-4939-1096-0_14 (2014).

43 Nusser, Z. & Mody, I. Selective modulation of tonic and phasic inhibitions in dentate gyrus granule cells. J Neurophysiol 87, 2624-2628 (2002).

44 S, A. FastQC: A Quality Control Tool for High Throughput Sequence Data. (2010).

45 Dobin, A. et al. STAR: ultrafast universal RNA-seq aligner. Bioinformatics 29, 15-21, doi: 10.1093/bioinformatics/bts635 (2013). 46 Liao, Y., Smyth, G. K. & Shi, W. featureCounts: an efficient general purpose program for assigning sequence reads to genomic features. Bioinformatics 30, 923-930, doi: 10.1093/bioinformatics/btt656 (2014).

47 Love, M. I., Huber, W. & Anders, S. Moderated estimation of fold change and dispersion for RNA-seq data with DESeq2. Genome Biol 15, 550, doi:10.1186/s13059-014-0550-8 (2014).

48 Team, R. C. D. R: A Language and Environment for Statistical Computing. ISBN 3-900051-07-0, URL www.R-project.org. Vienna, Austria (2010).

49 Subramanian, A. et al. Gene set enrichment analysis: a knowledge-based approach for interpreting genome-wide expression profiles. Proc Natl Acad Sci USA 102, 15545-15550, doi:10.1073/pnas.0506580102 (2005).

50 Lopez-Munoz, A., Roca, F. J., Meseguer, J. & Mulero, V. New insights into the evolution of IFN s: zebrafish group II IFN s induce a rapid and transient expression of IFNdependent genes and display powerful antiviral activities. J Immunol 182, 3440-3449, doi: 10.4049/jimmunol.0802528 (2009).

51 Engeszer, R. E., Patterson, L. B., Rao, A. A. & Parichy, D. M. Zebrafish in the wild: a review of natural history and new notes from the field. Zebrafish 4, 21-40, doi: 10.1089/zeb.2006.9997 (2007).

52 Krause, J., Butlin, R. K., Peuhkuri, N. & Pritchard, V. L. The social organization of fish shoals: a test of the predictive power of laboratory experiments for the field. Biol Rev Camb Philos Soc 75, 477-501 (2000).

53 Miller, N. & Gerlai, R. Quantification of shoaling behaviour in zebrafish (Dania rerio). Behav Brain Res 184, 157-166, doi:10.1016/j.bbr.2007.07.007 (2007).

54 Saverino, C. & Gerlai, R. The social zebrafish: behavioral responses to conspecific, heterospecific, and computer animated fish. Behav Brain Res 191, 77-87, doi: 10.1016/j.bbr.2008.03.013 (2008).

55 Barba-Escobedo, P. A. & Gould, G. G. Visual social preferences of lone zebrafish in a novel environment: strain and anxiolytic effects. Genes Brain Behav 11, 366-373, doi: 10.ll ll/j.1601-183X.2012.00770.x (2012).

56 Moy, S. S. et al. Sociability and preference for social novelty in five inbred strains: an approach to assess autistic-like behavior in mice. Genes Brain Behav 3, 287-302, doi: 10.ll ll/j.1601-1848.2004.00076.x (2004).

57 Moretz, J. A., Martins, E. P. & Robison, B. D. Behavioral syndromes and the evolution of correlated behavior in zebrafish. Behavioral Ecology 18, 556-562, doi: 10.1093/beheco/armO 11 (2007).

58 Wright, D., Butlin, R. K. & Carlborg, O. Epistatic regulation of behavioural and morphological traits in the zebrafish (Dania rerio). Behav Genet 36, 914-922, doi: 10.1007/s10519-006-9080-9 (2006).

59 Zala, S. M., Miiiittiinen, I. & Penn, D. J. Different social-learning strategies in wild and domesticated zebrafish, Dania rerio. Animal Behaviour 83, 1519-1525, doi:dx.doi.org/10.1016/j.anbehav 0.2012.03.029 (2012).

60 Levine, J. D., Funes, P., Dowse, H. B. & Hall, J. C. Resetting the circadian clock by social experience in *Drosophila melanogaster*. Science 298, 2010-2012, doi: 10.1126/science.1076008 (2002).
61 Mery, F. et al. Public versus personal information for mate copying in an invertebrate. Curr Biol 19, 730-734, doi:10.1016/j.cub.2009.02.064 (2009).
62 Ruan, H. & Wu, C. F. Social interaction-mediated lifespan extension of *Drosophila Cu/Zn superoxide dismutase mutants*. Proc NatlAcad Sci USA 105, 7506-7510, doi: 10.1073/pnas.0711127105 (2008).
63 Sarin, S. & Dukas, R. Social learning about egg-laying substrates in fruit flies. Proc Biol Sci 276, 4323-4328, doi:10.1098/rspb.2009.1294 (2009).
64 Sokolowski, M. B. Social interactions in "simple" model systems. Neuron 65, 780-794, doi: 10.1016/j.neuron.2010.03.007 (2010). 65 Wertheim, B., van Baalen, E. J., Dicke, M. & Vet, L. E. Pheromone-mediated aggregation in nonsocial arthropods: an evolutionary ecological perspective. Annu Rev Entomol 50, 321-346, doi: 10.1146/annurev.ento.49.061802.123329 (2005).
66 Hoffmann, A. A. A laboratory study of male territoriality in the sibling species *Drosophila melanogaster* and *D. simulans*. Animal Behaviour 35, 807-818, doi:dx.doi.org/10.1016/S0003-3472(87)80117-3 (1987).
67 Kamyshev, N. G. et al. Plasticity of social behavior in *Drosophila*. Neurosci Behav Physiol 32, 401-408 (2002).
68 Wang, L., Dankert, H., Perona, P. & Anderson, D. J. A common genetic target for environmental and heritable influences on aggressiveness in *Drosophila*. Proc Natl Acad Sci USA 105, 5657-5663, doi:10.1073/pnas.0801327105 (2008).
69 Bailey, T. L. et al. MEME SUITE: tools for motif discovery and searching. Nucleic Acids Res 37, W202-208, doi: 10.1093/nar/gkp335 (2009).
70 Krzywinski, M. et al. Circos: an information aesthetic for comparative genomics. Genome Res 19, 1639-1645, doi: 10.1101/gr.092759.109 (2009).

What is claimed is:

1. A method of improving the sociability of an animal subject, comprising:
   administering to the subject a therapeutically effective amount of a compound that increases STAT1 activity, wherein the compound is IFN-γ,
   wherein the compound is administered into the cerebrospinal fluid (CSF) of the subject, and
   wherein the subject is a knockout animal deficient in IFN-γ (IFN-γ KO).

2. The method of claim 1, wherein the compound increases STAT1 activity in GABAergic inhibitory neurons.

3. The method of claim 1, wherein the compound increases GABAergic transmission.

* * * * *